United States Patent
Leonard et al.

(10) Patent No.: US 9,346,782 B2
(45) Date of Patent: *May 24, 2016

(54) ALKYL LINKED QUINOLINYL MODULATORS OF RORγT

(71) Applicant: Janssen Pharmaceutica NV, Beerse (BE)

(72) Inventors: Kristi A. Leonard, Lansdale, PA (US); Kent Barbay, Flourtown, PA (US); James P. Edwards, San Diego, CA (US); Kevin D. Kreutter, Plainsboro, NJ (US); David A. Kummer, San Diego, CA (US); Umar Maharoof, North Wales, PA (US); Rachel Nishimura, San Diego, CA (US); Maud Urbanski, Flemington, NJ (US); Hariharan Venkatesan, San Diego, CA (US); Aihua Wang, Jamison, PA (US); Ronald L. Wolin, San Diego, CA (US); Craig R. Woods, San Diego, CA (US); Maxwell D. Cummings, Ambler, PA (US)

(73) Assignee: Janssen Pharmaceutica NV (BE)

(*) Notice: Subject to any disclaimer, the term of this patent is extended or adjusted under 35 U.S.C. 154(b) by 0 days.

This patent is subject to a terminal disclaimer.

(21) Appl. No.: 14/513,455

(22) Filed: Oct. 14, 2014

(65) Prior Publication Data

US 2015/0105369 A1    Apr. 16, 2015

Related U.S. Application Data

(60) Provisional application No. 61/890,890, filed on Oct. 15, 2013.

(51) Int. Cl.
  C07D 401/06  (2006.01)
  C07D 417/06  (2006.01)
  C07D 413/06  (2006.01)

(52) U.S. Cl.
  CPC ............ *C07D 401/06* (2013.01); *C07D 413/06* (2013.01); *C07D 417/06* (2013.01)

(58) Field of Classification Search
  CPC ... C07D 401/06; C07D 417/06; C07D 413/06
  USPC ........ 514/210.18, 210.21, 312, 314; 546/173, 546/157, 172
  See application file for complete search history.

(56) References Cited

U.S. PATENT DOCUMENTS

| | | | |
|---|---|---|---|
| 3,472,859 A | 10/1969 | Lesher | |
| 4,656,283 A | 4/1987 | Doehner, Jr. | |
| 4,710,507 A | 12/1987 | Campbell et al. | |
| 4,910,327 A | 3/1990 | Doehner, Jr. | |
| 4,927,926 A | 5/1990 | Corominas et al. | |
| 5,409,930 A | 4/1995 | Spada et al. | |
| 5,780,634 A | 7/1998 | Inoue et al. | |
| 6,248,739 B1 | 6/2001 | Turner et al. | |
| 6,451,812 B1 | 9/2002 | End et al. | |
| 6,624,159 B2 | 9/2003 | Anderson et al. | |
| 6,686,356 B2 | 2/2004 | Strohbach et al. | |
| 6,743,805 B2 | 6/2004 | End et al. | |
| 7,053,105 B2 | 5/2006 | Angibaud et al. | |
| 7,652,014 B2 | 1/2010 | Mabire et al. | |
| 7,902,225 B2 | 3/2011 | Guillemont et al. | |
| 8,017,606 B2 | 9/2011 | Andries et al. | |
| 8,389,739 B1 | 3/2013 | Thacher et al. | |
| 2003/0166675 A1 | 9/2003 | Yang | |

(Continued)

FOREIGN PATENT DOCUMENTS

| | | |
|---|---|---|
| CN | 101143845 | 3/2008 |
| CN | 101899011 | 12/2010 |

(Continued)

OTHER PUBLICATIONS

Bink A, (A fungicidal piperazine-1-carboxamidine induces mitochondrial fission-dependent apoptosis in yeast), FEMS Yeast Research (2010), 10(7), 812-818.

Nieman J, (Modifications of C-2 on the pyrroloquinoline template aimed at the development of potent herpes virus antivirals with improved aqueous solubility), Bioorganic & Medicinal Chemistry Letters (2010), 20(10), 3039-3042.

Tanis S, (The design and development of 2-aryl-2-hydroxy ethylamine substituted 1H,7H-pyrido[1,2,3-de]quinoxaline-6-carboxamides as inhibitors of human cytomegalovirus polymerase), Bioorganic & Medicinal Chemistry Letters (2010), 20(6), 1994-2000.

(Continued)

*Primary Examiner* — Janet L Andres
*Assistant Examiner* — Daniel Carcanague
(74) *Attorney, Agent, or Firm* — Yuriy P. Stercho

(57) ABSTRACT

The present invention comprises compounds of Formula I.

Formula I wherein:
$R^1$, $R^2$, $R^3$, $R^4$, $R^5$, $R^6$, $R^7$, $R^8$, and $R^9$ are defined in the specification.

The invention also comprises a method of treating or ameliorating a syndrome, disorder or disease, wherein said syndrome, disorder or disease is rheumatoid arthritis or psoriasis. The invention also comprises a method of modulating RORγt activity in a mammal by administration of a therapeutically effective amount of at least one compound of claim 1.

6 Claims, No Drawings

(56) References Cited

U.S. PATENT DOCUMENTS

| | | |
|---|---|---|
| 2005/0131014 A1 | 6/2005 | Collini et al. |
| 2007/0072844 A1 | 3/2007 | Jones et al. |
| 2008/0188521 A1 | 8/2008 | Grimm et al. |
| 2009/0197859 A1 | 8/2009 | Collantes et al. |
| 2009/0286829 A1 | 11/2009 | Heidelbaugh et al. |
| 2010/0311760 A1 | 12/2010 | de Vicente Fidalgo et al. |
| 2011/0124870 A1 | 5/2011 | Guillemont et al. |
| 2012/0322837 A1 | 12/2012 | Maeba et al. |
| 2014/0107094 A1 | 4/2014 | Leonard et al. |
| 2014/0107096 A1* | 4/2014 | Leonard et al. ........... 514/210.21 |
| 2014/0107097 A1* | 4/2014 | Leonard et al. ........... 514/210.21 |
| 2015/0105365 A1* | 4/2015 | Leonard et al. ........... 514/210.02 |
| 2015/0105366 A1* | 4/2015 | Leonard et al. ........... 514/210.18 |
| 2015/0105372 A1* | 4/2015 | Leonard et al. ........... 514/210.21 |
| 2015/0105404 A1* | 4/2015 | Leonard et al. ............... 514/256 |
| 2015/0111870 A1* | 4/2015 | Leonard et al. ........... 514/210.18 |

FOREIGN PATENT DOCUMENTS

| | | |
|---|---|---|
| EP | 371564 A2 | 6/1990 |
| EP | 709377 A1 | 5/1996 |
| EP | 1106612 A1 | 6/2001 |
| EP | 2368886 A1 | 9/2011 |
| GB | 2095668 A | 10/1982 |
| JP | 48026772 | 4/1973 |
| JP | 2000169451 A | 6/2000 |
| WO | WO 9718208 A1 | 5/1997 |
| WO | WO 9721701 A1 | 6/1997 |
| WO | WO 9744339 A1 | 11/1997 |
| WO | WO 9855124 A1 | 12/1998 |
| WO | WO 9932450 A1 | 7/1999 |
| WO | WO 9950660 A1 | 10/1999 |
| WO | WO 0001386 A1 | 1/2000 |
| WO | WO 0001411 A1 | 1/2000 |
| WO | WO 0001714 A1 | 1/2000 |
| WO | WO 0039082 A2 | 7/2000 |
| WO | WO 0040561 A1 | 7/2000 |
| WO | WO 0040563 A1 | 7/2000 |
| WO | WO 0047574 A1 | 8/2000 |
| WO | WO 0156552 A2 | 8/2001 |
| WO | WO 0162234 A2 | 8/2001 |
| WO | WO 0164194 A2 | 9/2001 |
| WO | WO 0164195 A2 | 9/2001 |
| WO | WO 0164196 A2 | 9/2001 |
| WO | WO 0164197 A2 | 9/2001 |
| WO | WO 0164198 A2 | 9/2001 |
| WO | WO 0164199 A2 | 9/2001 |
| WO | WO 0164217 A2 | 9/2001 |
| WO | WO 0164218 A2 | 9/2001 |
| WO | WO 0164226 A2 | 9/2001 |
| WO | WO 0164246 A2 | 9/2001 |
| WO | WO 0164252 A2 | 9/2001 |
| WO | WO 0202558 A1 | 1/2002 |
| WO | WO 0204445 A1 | 1/2002 |
| WO | WO 0204462 A1 | 1/2002 |
| WO | WO 0224682 A1 | 3/2002 |
| WO | WO 0224686 A2 | 3/2002 |
| WO | WO 02024687 A1 | 3/2002 |
| WO | WO 0228837 A1 | 4/2002 |
| WO | WO 0243733 A1 | 6/2002 |
| WO | WO 02051835 A1 | 7/2002 |
| WO | WO 02064142 A1 | 8/2002 |
| WO | WO 02070487 A1 | 9/2002 |
| WO | WO 02085364 A1 | 10/2002 |
| WO | WO 03/000705 | 1/2003 |
| WO | WO 03053971 A1 | 7/2003 |
| WO | WO 03053972 A1 | 7/2003 |
| WO | WO 03082350 A2 | 10/2003 |
| WO | WO 2004019932 A1 | 3/2004 |
| WO | WO 2004024693 A1 | 3/2004 |
| WO | WO 2004037792 A2 | 5/2004 |
| WO | WO 2005054201 A1 | 6/2005 |
| WO | WO 2005054210 A1 | 6/2005 |
| WO | WO 2005058843 A1 | 6/2005 |
| WO | WO 2005070430 A1 | 8/2005 |
| WO | WO 2005075428 A1 | 8/2005 |
| WO | WO 2006003146 A1 | 1/2006 |
| WO | WO 2006013896 A1 | 2/2006 |
| WO | WO 2006025683 | 3/2006 |
| WO | WO 2006052718 A2 | 5/2006 |
| WO | WO 2007014940 A2 | 2/2007 |
| WO | WO 2007014941 A2 | 2/2007 |
| WO | WO 2007088978 A1 | 8/2007 |
| WO | WO 2008051805 A2 | 5/2008 |
| WO | WO 2008068267 A1 | 6/2008 |
| WO | WO 2008098104 A8 | 8/2008 |
| WO | WO 2008112525 A2 | 9/2008 |
| WO | WO 2008144767 A1 | 11/2008 |
| WO | WO 2009091735 A1 | 7/2009 |
| WO | WO 2009140138 A1 | 11/2009 |
| WO | WO 2010068296 A1 | 6/2010 |
| WO | WO 2010127208 A1 | 11/2010 |
| WO | WO 2010151740 A4 | 12/2010 |
| WO | WO 2011020861 A1 | 2/2011 |
| WO | WO 2011112264 A1 | 9/2011 |
| WO | WO 2011130707 A2 | 10/2011 |
| WO | WO 2012064744 A2 | 5/2012 |
| WO | WO 2012116137 A2 | 8/2012 |
| WO | WO 2012158784 A2 | 11/2012 |
| WO | WO 2013/061074 * | 5/2013 |
| WO | WO 2013061074 A1 | 5/2013 |
| WO | WO 2013064231 A1 | 5/2013 |
| WO | WO 2013079223 A1 | 6/2013 |

OTHER PUBLICATIONS

Mao D, (Synthesis and Na+/H+ Exchanger-1 Inhibitory Activity of Substituted (Quinolinecarbonyl)guanidine Derivatives), Chemistry & Biodiversity (2009), 6(10), 1727-1736.

Sato M, (Quinolone Carboxylic Acids as a Novel Monoketo Acid Class of Human Immunodeficiency Virus Type 1 Integrase Inhibitors), Journal of Medicinal Chemistry (2009), 52(15), 4869-4882.

Aghera V, (Synthesis, spectral and microbial studies of some novel quinoline derivatives via Vilsmeier-Haack reagent) Journal; (online computer file URL: http://www.arkat-usa.org/get-file/25177/; ARKIVOC 2008 (12) 195-204.

Inada T, (One-step synthesis of ethyl quinaldates by Lewis acid-catalyzed three-component coupling reaction of aromatic amines, aliphatic aldehydes, and ethyl glyoxylate), Heterocycles (2005), 66, 611-619.

Zelenin A, (Reaction of polyfluoro carbonyl compounds with 1,2,3,4-tetrahydroquinoline), Izvestiya Akademii Nauk SSSR, Seriya Khimicheskaya (1986), (9), 2074-80 Abstract Only.

Hirao I, (Studies on the synthesis of quinoline compounds. I. Syntheses of 3,3'-dicarboxy-1,1'-diethyl-4,4'-dioxo-1,1',4,4'-tetrahydrobiquinolines), Memoirs of the Kyushu Insitute of Technology, Engineering (1984), 14,13-16.

Abdul-Ahad P, (Trends in dehydrogenase inhibitory potencies of some quinolones, using quantum chemical indices), European Journal of Medicinal Chemistry (1982), 17(4), 301-6.

Baker B, (Irreversible enzyme inhibitors. 191. Hydrophobic bonding to some dehydrogenases by 6-, 7-, or 8-substituted-4-hydroxyquinoline-3-carboxylic acids), Journal of Medicinal Chemistry (1972), 15(3), 235-7.

Ramachary D, (A novel and green protocol for two-carbon homologation: a direct amino acid/K2CO3-catalyzed four-component reaction of aldehydes, active methylenes, Hantzsch esters and alkyl halides), Tetrahedron Letters (2006) 47, 651-656.

Dong C, (Diversification of T-helper-cell lineages: finding the family root of IL-17-producing cells), Nat Rev Immunol (2006), 6(4), 329-333.

McKenzie B, (Understanding the IL-23-IL-17 immune pathway), Trends Immunol (2006), 27(1), 17-23.

Ivanov II B, (the orphan nuclear receptor RORgammat directs the differentiation program of proinflammatory IL-17+ T helper cells), Cell (2006), 126(6), 1121-33.

Cua, D (Interleukin-23 rather than interleukin-12 is the critical cytokine for autoimmune inflammation of the brain), Nature (2003), 421(6924), 744-748.

(56) References Cited

OTHER PUBLICATIONS

Langrish C, (IL-23 drives a pathogenic T cell population that induces autoimmune inflammation), J Exp Med (2005), 201(2), 233-240.
Tonel G, (Cutting edge: A critical functional role for IL-23 in psoriasis), J Immunol (2010), 185(10), 5688-5691.
Barczyk A, (Interleukin-17 in sputum correlates with airway hyper-responsiveness to methacholine), Respir Med (2003), 97(6), 726-733.
Lock C, (Gene-microarray analysis of multiple sclerosis lesions yields new targets validated in autoimmune encephalomyelitis) Nat Med (2002), 8(5), 500-8.
Papp K, (Brodalumab, an anti-interleukin-17-receptor antibody for psoriasis), N Engl J Med (2012), 366(13), 1181-1189.
Leonardi C, (Anti-interleukin-17 monoclonal antibody ixekizumab in chronic plaque psoriasis), N Engl J Med (2012), 366(13), 1190-1199.
Hueber W, (Effects of AIN457, a fully human antibody to interleukin-17A, on psoriasis, rheumatoid arthritis, and uveitis), Sci Transl Med (2010), 2, 5272.
Gao W, (Clean and Convienient One-Pot Synthesis of 4-Hydroxycoumarin and 4-Hydroxy-2-Quinolone Derivatives), Synthetic Communications (2010) 40, 732-738.
Moriarty R, Organic Reactions (2001), 57, 327-415.
Pongratz E, et al., (Ylide von Heterocyclen, VIII Reaktionen von Iodonium-Yliden mit Säuren), Monatshefte fur Chemie (1984) 115(2), 231-242.
Osborne A, (Regioselective Al koxydehalogenation of 2,4- Di halogenoquinolines and a Reinvestigation of the Bromination of 2-Methoxyquinoline), J Chem Soc Perkin Trans 1 (1993), 181-184.
Osborne A, (Further studies of regioselective alkoxydehalogenation of 2,4-dichloroquinolines, 2,6-dichloropyridine and 2,4-dichloronitrobenzene), J Chem Research (S) (2002), 4.
Ramachary D, (Development of Pharmaceutical Drugs, Drug Intermediates and Ingredients by Using Direct Organo-Click Reactions), Eur. J. Org. Chem. (2008), 975-993.
Korn T, (IL-17 and Th17 Cells), Annual Reviews of Immunology (2009), 27, 485-517.
Kolls J, (Interleukin-17 family members and inflammation), Immunity (2004), 21(4), 467-476.
Stamp L, (Interleukin-17: the missing link between T-cell accumulation and effector cell actions in rheumatoid arthritis), Immunol Cell Biol (2004), 82(1), 1-9.
Kamenecka T, (Synthetic modulators of the retinoic acid receptor-related orphan receptors), Med Chem Commun (2013), 4, 764-776.
Yen D, (IL-23 is essential for T cell-mediated colitis and promotes inflammation via IL-17 and IL-6), J Clin Invest (2006), 116(5), 1310-1316.
Fujino S, (Increased expression of interleukin 17 in inflammatory bowel disease) Gut (2003), 52(1), 65-70.
Krueger J, (IL-17A is essential for cell activation and inflammatory gene circuits in subjects with psoriasis) J Allergy Clin Immunol (2012), 130(1), 145-154.
Nunez C, (IL23R: a susceptibility locus for celiac disease and multiple sclerosis?) Genes Immun (2008), 9(4), 289-93.
Bowes J, (The genetics of psoriatic arthritis: lessons from genome-wide association studies), Discov Med (2010), 10(52), 177-83.
Kochi Y, (A regulatory variant in CCR6 is associated with rheumatoid arthritis susceptibility), Nat Genet (2010), 42(6), 515-9.
Garber K, (Psoriasis: from bed to bench and back), Nat Biotech (2011), 29, 563-566.
Madrid P, et al. (Synthesis of ring-substituted 4-aminoquinolines and evaluation of their antimalarial activities), Bioorganic & Medicinal Chemistry Letters (2005), 15, 1015-1018.
Gore T, (Synthesis of substituted 6,6'-biquinolines from ethyl ethoxymethyleneacetoacetate), Indian Journal of Chemistry (1965), 3(2), 90-1.
Gazouli, M, (NOD2/CARD15, ATG16L1 and IL23R gene polymorphisms and childhood-onset of Crohn's disease) World J. Gastroenterol (2010) 16(14), 1753-8.
Knochel P, (Preparation of Polyfunctional Ketones by a Cobalt(II) Mediated Carbonylation of Organozinc Reagents), Tetrahedron Letters (1995), 36(46), 8411-8414.
Codarri, "RORγt Drives Production of the Cytokine GM-CSF in helper T cells, which is essential for the effector phase of Autoimmune Neuroinflammation", Nature Innumology, Jun. 2011, vol. 12(6), p. 560-568.
U.S. Appl. No. 14/053,682.
U.S. Appl. No. 14/053,736.
U.S. Appl. No. 14/053,773.
U.S. Appl. No. 14/053,906.
U.S. Appl. No. 14/053,653.
U.S. Appl. No. 14/053,707.
U.S. Appl. No. 14/513,426.
U.S. Appl. No. 14/513,455.
U.S. Appl. No. 14/053,797.
International Search Report—PCT/US2013/065007, Jan. 7, 2014.
International Search Report—PCT/US2013/065013, Dec. 16, 2013.
International Search Report—PCT/US2013/065031, Dec. 13, 2013.
International Search Report—PCT/US2013/065040, Dec. 16, 2013.
International Search Report—PCT/US2013/065048, Dec. 3, 2013.
International Search Report—PCT/US2013/065053, Jan. 7, 2014.
International Search Report—PCT/US2013/065026, Feb. 21, 2014.
International Search Report—PCT/US2014/60372, Mar. 27, 2015.
International Search Report—PCT/US2014/60375, Mar. 26, 2015.
U.S. Appl. No. 14/053,653, Office Action dated Sep. 15, 2014.
U.S. Appl. No. 14/053,653, Notice of Allowance dated Mar. 30, 2015.
U.S. Appl. No. 14/053,682, Office Action dated Sep. 12, 2014.
U.S. Appl. No. 14/053,682, Notice of Allowance dated Sep. 12, 2014.
U.S. Appl. No. 14/053,707, Office Action dated Sep. 11, 2014.
U.S. Appl. No. 14/053,707, Notice of Allowance dated Sep. 11, 2014.
U.S. Appl. No. 12/053,736, Office action dated Mar. 26, 2015.
U.S. Appl. No. 14/053,736, Office Action dated Oct. 3, 2014.
U.S. Appl. No. 14/053,773, Office Action dated Apr. 6, 2015.
U.S. Appl. No. 14/053,773, Office Action dated Jan. 9, 2015.
U.S. Appl. No. 14/053,797, Office Action dated Sep. 12, 2014.
U.S. Appl. No. 14/053,797, Notice of Allowance Apr. 7, 2015.
U.S. Appl. No. 14/513,426, Office Action dated Apr. 16, 2015.
U.S. Appl. No. 14/513,455, Office Action dated Apr. 28, 2015.
U.S. Appl. No. 14/053,906, Office Action dated 09/12/204.
U.S. Appl. No. 14/053,906, Notice of Allowance dated Mar. 23, 2015.
Dorwald F. A. "Slide Reactions in Organic Synthesis", 2005, Wiley: VCH, Weinheim p. IX of Preface p. 1-15.
Venkatesh, et al. "Role of the Development Scientist in Compound Lead Selection and Optimization", J. Pharm. Sci. vol. 89, No. 2, pp. 145-154 2000.
Hiro, STN Document No. 102: 149081 Abstract of Memoirs of the Kyushu Institute of Technology, Engineering (1984), vol. 14, pp. 13-16.
STN Search Report Mar. 12, 2015, RN 1347913-41-0.

* cited by examiner

SEQUENCE LISTING

<160> NUMBER OF SEQ ID NOS: 9

<210> SEQ ID NO 1
<211> LENGTH: 3054
<212> TYPE: DNA
<213> ORGANISM: Homo sapiens

<400> SEQUENCE: 1

-continued

```
agagagctag gtgcagagct tcaggctgag gcgctgctga gagggcctcg ccccgcctct    60
gccgccagct gcaccccact cctgaccac ccctgctga aaggacagg gagccaaggc      120
cggcagagcc aaggctcagt catgagaaca caaattgaag tgatcccttg caaaatctgt   180
ggggacaagt cgtctgggat ccactacggg gttatcacct gtgaggggtg caagggcttc   240
ttccgccgga gccagcgctg taacgcggcc tactcctgca cccgtcagca gaactgcccc   300
atcgaccgca ccagccgaaa ccgatgccag cactgccgcc tgcagaaatg cctggcgctg   360
ggcatgtccc gagatgctgt caagttcggc cgcatgtcca agaagcagag ggacagcctg   420
catgcagaag tgcagaaaca gctgcagcag cggcaacagc agcaacagga accagtggtc   480
aagacccctc cagcaggggc ccaaggagca gatacctca cctacacctt ggggctccca   540
gacgggcagc tgcccctggg ctcctcgcct gacctgcctg aggcttctgc ctgtccccct   600
ggcctcctga aagcctcagg ctctgggccc tcatattcca acaacttggc caaggcaggg   660
ctcaatgggg cctcatgcca ccttgaatac agccctgagc ggggcaaggc tgagggcaga   720
gagagcttct atagcacagg cagccagctg acccctgacc gatgtggact tcgttttgag   780
gaacacagg atcctgggct tggggaactg ggacagggcc cagacagcta cggcagcccc   840
agtttccgca gcacaccgga ggcaccctat gcctccctga cagagataga gcacctggtg   900
cagagcgtct gcaagtccta cagggagaca tgccagctgc ggctggagga cctgctgcgg   960
cagcgctcca acatcttctc ccgggaggaa gtgactggct accagaggaa gtccatgtgg  1020
gagatgtggg aacggtgtgc ccaccacctc accgaggcca ttcagtacgt ggtggagttc  1080
gccaagaggc tctcaggctt tatggagctc tgccagaatg accagattgt gcttctcaaa  1140
gcaggagcaa tggaagtggt gctggttagg atgtgccggg cctacaatgc tgacaaccgc  1200
acggtctttt ttgaaggcaa atacggtggc atggagctgt tccgagcctt gggctgcagc  1260
gagctcatca gctccatctt tgacttctcc cactccctaa gtgccttgca cttttccgag  1320
gatgagattg ccctctacac agcccttgtt ctcatcaatg cccatcggcc agggctccaa  1380
gagaaaagga agtagaaca gctgcagtac aatctggagc tggcctttca tcatcatctc  1440
tgcaagactc atcgccaaag catcctggca agctgccac ccaaggggaa gcttcggagc  1500
ctgtgtagcc agcatgtgga aaggctgcag atcttccagc acctccaccc catcgtggtc  1560
caagccgctt tccctccact ctacaaggag ctcttcagca ctgaaaccga gtcacctgtg  1620
gggctgtcca agtgacctgg aagagggact ccttgcctct ccctatggcc tgctggccca  1680
cctcccctgga ccccgttcca ccctcaccct tttcctttcc catgaaccct ggagggtggt  1740
ccccaccagc tctttggaag tgagcagatg ctgcggctgg ctttctgtca gcaggccggc  1800
ctggcagtgg gacaatcgcc agagggtggg gctggcagaa caccatctcc agcctcagct  1860
ttgacctgtc tcatttccca tattccttca cacccagctt ctggaaggca tggggtggct  1920
gggatttaag gacttctggg ggaccaagac atcctcaaga aaacagggc atccagggct  1980
ccctggatga atagaatgca attcattcag aagctcagaa gctaagaata agcctttgaa  2040
atacctcatt gcatttccct ttgggcttcg gcttggggag atggatcaag ctcagagact  2100
ggcagtgaga gcccagaagg acctgtataa aatgaatctg gagctttaca ttttctgcct  2160
ctgccttcct cccagctcag caaggaagta tttgggcacc ctaccctta cctggggtct  2220
aaccaaaaat ggatgggatg aggatgagag gctggagata attgttttat gggatttggg  2280
tgtgggacta gggtacaatg aaggccaaga gcatctcaga catagagtta aaactcaaac  2340
```

```
ctcttatgtg cactttaaag atagacttta ggggctggca caaatctgat cagagacaca   2400
tatccataca caggtgaaac acatacagac tcaacagcaa tcatgcagtt ccagagacac   2460
atgaacctga cacaatctct cttatccttg aggccacagc ttggaggagc ctagaggcct   2520
caggggaaag tcccaatcct gagggaccct cccaaacatt tccatggtgc tccagtccac   2580
tgatcttggg tctggggtga tccaaatacc accccagctc agctgtgtct ctaccactag   2640
aagacccaag agaagcagaa gtcgctcgca ctggtcagtc ggaaggcaag atcagatcct   2700
ggaggacttt cctggcctgc ccgccagccc tgctcttgtt gtggagaagg aagcagatgt   2760
gatcacatca ccccgtcatt gggcaccgct gactccagca tggaggacac cagggagcag   2820
ggcctgggcc tgtttcccca gctgtgatct tgcccagaac ctctcttggc ttcataaaca   2880
gctgtgaacc ctcccctgag ggattaacag caatgatggg cagtcgtgga gttgggggg   2940 ttggggtgg gattgtgtcc tctaagggga cgggttcatc tgagtaaaca taaaccccaa   3000
cttgtgccat tctttataaa atgatttta aggcaaaaaa aaaaaaaaaa aaaa         3054
```

```
<210> SEQ ID NO 2
<211> LENGTH: 786
<212> TYPE: DNA
<213> ORGANISM: Homo sapiens

<400> SEQUENCE: 2
agcacaccgg aggcacccta tgcctccctg acagagatag agcacctggt gcagagcgtc     60
tgcaagtcct acaggagac atgccagctg cggctggagg acctgctgcg gcagcgctcc    120
aacatcttct cccgggagga agtgactggc taccagagga gtccatgtg ggagatgtgg    180 gaacggtgtg cccaccacct caccgaggcc attcagtacg tggtggagtt cgccaagagg    240
ctctcaggct ttatggagct ctgccagaat gaccagattg tgcttctcaa gcaggagca    300 atggaagtgg tgctggttag gatgtgccgg gcctacaatg ctgacaaccg cacggtcttt    360
tttgaaggca aatacggtgg catggagctg ttccgagcct tgggctgcag cgagctcatc    420
agctccatct ttgacttctc ccactcccta agtgccttgc acttttccga ggatgagatt    480
gccctctaca cagccctttgt tctcatcaat gcccatcggc cagggctcca agagaaaagg    540
aaagtagaac agctgcagta caatctggag ctggcctttc atcatcatct ctgcaagact    600
catcgccaaa gcatcctggc aaagctgcca cccaagggga agcttcggag cctgtgtagc    660
cagcatgtgg aaaggctgca gatcttccag cacctccacc ccatcgtggt ccaagccgct    720
ttccctccac tctacaagga gctcttcagc actgaaaccg agtcacctgt ggggctgtcc    780
aagtga                                                              786
```

```
<210> SEQ ID NO 3
<211> LENGTH: 7
<212> TYPE: PRT
<213> ORGANISM: Artificial Sequence
<220> FEATURE:
<223> OTHER INFORMATION: TurboTEV protease cleavage site

<400> SEQUENCE: 3

Glu Asn Leu Tyr Phe Gln Gly
1               5
```

```
<210> SEQ ID NO 4
<211> LENGTH: 283
<212> TYPE: PRT
<213> ORGANISM: Artificial Sequence
<220> FEATURE:
```

<223> OTHER INFORMATION: Construct used in the Thermofluor assay

<400> SEQUENCE: 4

```
Met Ala His His His His His Ala Gly Ala Glu Asn Leu Tyr
 1               5                  10                  15

Phe Gln Gly Ala Met Asp Ser Thr Pro Glu Ala Pro Tyr Ala Ser Leu
             20                  25                  30

Thr Glu Ile Glu His Leu Val Gln Ser Val Cys Lys Ser Tyr Arg Glu
         35                  40                  45

Thr Cys Gln Leu Arg Leu Glu Asp Leu Leu Arg Gln Arg Ser Asn Ile
     50                  55                  60

Phe Ser Arg Glu Glu Val Thr Gly Tyr Gln Arg Lys Ser Met Trp Glu
 65                  70                  75                  80

Met Trp Glu Arg Cys Ala His His Leu Thr Glu Ala Ile Gln Tyr Val
                 85                  90                  95

Val Glu Phe Ala Lys Arg Leu Ser Gly Phe Met Glu Leu Cys Gln Asn
             100                 105                 110

Asp Gln Ile Val Leu Leu Lys Ala Gly Ala Met Glu Val Val Leu Val
         115                 120                 125

Arg Met Cys Arg Ala Tyr Asn Ala Asp Asn Arg Thr Val Phe Phe Glu
     130                 135                 140

Gly Lys Tyr Gly Gly Met Glu Leu Phe Arg Ala Leu Gly Cys Ser Glu
145                 150                 155                 160

Leu Ile Ser Ser Ile Phe Asp Phe Ser His Ser Leu Ser Ala Leu His
                 165                 170                 175

Phe Ser Glu Asp Glu Ile Ala Leu Tyr Thr Ala Leu Val Leu Ile Asn
             180                 185                 190

Ala His Arg Pro Gly Leu Gln Glu Lys Arg Lys Val Glu Gln Leu Gln
         195                 200                 205

Tyr Asn Leu Glu Leu Ala Phe His His His Leu Cys Lys Thr His Arg
     210                 215                 220

Gln Ser Ile Leu Ala Lys Leu Pro Pro Lys Gly Lys Leu Arg Ser Leu
225                 230                 235                 240

Cys Ser Gln His Val Glu Arg Leu Gln Ile Phe Gln His Leu His Pro
                 245                 250                 255

Ile Val Val Gln Ala Ala Phe Pro Pro Leu Tyr Lys Glu Leu Phe Ser
             260                 265                 270

Thr Glu Thr Glu Ser Pro Val Gly Leu Ser Lys
         275                 280
```

<210> SEQ ID NO 5
<211> LENGTH: 6
<212> TYPE: PRT
<213> ORGANISM: Homo sapiens

<400> SEQUENCE: 5

```
Leu Tyr Lys Glu Leu Phe
 1               5
```

<210> SEQ ID NO 6
<211> LENGTH: 6
<212> TYPE: PRT
<213> ORGANISM: Artificial Sequence
<220> FEATURE:
<223> OTHER INFORMATION: mutated AF2 domain

<400> SEQUENCE: 6

```
Leu Phe Lys Glu Leu Phe
1               5
```

<210> SEQ ID NO 7
<211> LENGTH: 786
<212> TYPE: DNA
<213> ORGANISM: Artificial Sequence
<220> FEATURE:
<223> OTHER INFORMATION: LBD with mutated AF2 domain

<400> SEQUENCE: 7

```
agcacaccgg aggcacccta tgcctccctg acagagatag agcacctggt gcagagcgtc    60
tgcaagtcct acagggagac atgccagctg cggctggagg acctgctgcg gcagcgctcc   120
aacatcttct cccggggagga agtgactggc taccagagga gtccatgtg ggagatgtgg   180
gaacggtgtg cccaccacct caccgaggcc attcagtacg tggtggagtt cgccaagagg   240
ctctcaggct ttatggagct ctgccagaat gaccagattg tgcttctcaa agcaggagca   300
atggaagtgg tgctggttag gatgtgccgg gcctacaatg ctgacaaccg cacggtcttt   360
tttgaaggca atacggtgg catggagctg ttccgagcct gggctgcag cgagctcatc   420
agctccatct ttgacttctc ccactcccta agtgccttgc acttttccga ggatgagatt   480
gccctctaca cagcccttgt tctcatcaat gcccatcggc agggctcca agagaaaagg   540
aaagtagaac agctgcagta caatctggag ctggcctttc atcatcatct ctgcaagact   600
catcgccaaa gcatcctggc aaagctgcca cccaagggga agcttcggag cctgtgtagc   660
cagcatgtgg aaaggctgca gatcttccag cacctccacc ccatcgtggt ccaagccgct   720
ttccctccac tcttcaagga gctcttcagc actgaaaccg agtcacctgt ggggctgtcc   780
aagtga                                                              786
```

<210> SEQ ID NO 8
<211> LENGTH: 261
<212> TYPE: PRT
<213> ORGANISM: Homo sapiens

<400> SEQUENCE: 8

```
Ser Thr Pro Glu Ala Pro Tyr Ala Ser Leu Thr Glu Ile Glu His Leu
1               5                   10                  15

Val Gln Ser Val Cys Lys Ser Tyr Arg Glu Thr Cys Gln Leu Arg Leu
            20                  25                  30

Glu Asp Leu Leu Arg Gln Arg Ser Asn Ile Phe Ser Arg Glu Glu Val
        35                  40                  45

Thr Gly Tyr Gln Arg Lys Ser Met Trp Glu Met Trp Glu Arg Cys Ala
    50                  55                  60

His His Leu Thr Glu Ala Ile Gln Tyr Val Val Glu Phe Ala Lys Arg
65                  70                  75                  80

Leu Ser Gly Phe Met Glu Leu Cys Gln Asn Asp Gln Ile Val Leu Leu
                85                  90                  95

Lys Ala Gly Ala Met Glu Val Val Leu Val Arg Met Cys Arg Ala Tyr
            100                 105                 110

Asn Ala Asp Asn Arg Thr Val Phe Phe Glu Gly Lys Tyr Gly Gly Met
        115                 120                 125

Glu Leu Phe Arg Ala Leu Gly Cys Ser Glu Leu Ile Ser Ser Ile Phe
    130                 135                 140

Asp Phe Ser His Ser Leu Ser Ala Leu His Phe Ser Glu Asp Glu Ile
145                 150                 155                 160
```

```
Ala Leu Tyr Thr Ala Leu Val Leu Ile Asn Ala His Arg Pro Gly Leu
            165                 170                 175

Gln Glu Lys Arg Lys Val Glu Gln Leu Gln Tyr Asn Leu Glu Leu Ala
        180                 185                 190

Phe His His His Leu Cys Lys Thr His Arg Gln Ser Ile Leu Ala Lys
    195                 200                 205

Leu Pro Pro Lys Gly Lys Leu Arg Ser Leu Cys Ser Gln His Val Glu
210                 215                 220

Arg Leu Gln Ile Phe Gln His Leu His Pro Ile Val Val Gln Ala Ala
225                 230                 235                 240

Phe Pro Pro Leu Tyr Lys Glu Leu Phe Ser Thr Glu Thr Glu Ser Pro
                245                 250                 255

Val Gly Leu Ser Lys
                260

<210> SEQ ID NO 9
<211> LENGTH: 261
<212> TYPE: PRT
<213> ORGANISM: Artificial Sequence
<220> FEATURE:
<223> OTHER INFORMATION: LBD with mutated AF2 domain

<400> SEQUENCE: 9

Ser Thr Pro Glu Ala Pro Tyr Ala Ser Leu Thr Glu Ile Glu His Leu
1               5                   10                  15

Val Gln Ser Val Cys Lys Ser Tyr Arg Glu Thr Cys Gln Leu Arg Leu
            20                  25                  30

Glu Asp Leu Leu Arg Gln Arg Ser Asn Ile Phe Ser Arg Glu Glu Val
        35                  40                  45

Thr Gly Tyr Gln Arg Lys Ser Met Trp Glu Met Trp Glu Arg Cys Ala
    50                  55                  60

His His Leu Thr Glu Ala Ile Gln Tyr Val Val Glu Phe Ala Lys Arg
65                  70                  75                  80

Leu Ser Gly Phe Met Glu Leu Cys Gln Asn Asp Gln Ile Val Leu Leu
                85                  90                  95

Lys Ala Gly Ala Met Glu Val Val Leu Val Arg Met Cys Arg Ala Tyr
            100                 105                 110

Asn Ala Asp Asn Arg Thr Val Phe Phe Glu Gly Lys Tyr Gly Gly Met
        115                 120                 125

Glu Leu Phe Arg Ala Leu Gly Cys Ser Glu Leu Ile Ser Ser Ile Phe
    130                 135                 140

Asp Phe Ser His Ser Leu Ser Ala Leu His Phe Ser Glu Asp Glu Ile
145                 150                 155                 160

Ala Leu Tyr Thr Ala Leu Val Leu Ile Asn Ala His Arg Pro Gly Leu
                165                 170                 175

Gln Glu Lys Arg Lys Val Glu Gln Leu Gln Tyr Asn Leu Glu Leu Ala
            180                 185                 190

Phe His His His Leu Cys Lys Thr His Arg Gln Ser Ile Leu Ala Lys
        195                 200                 205

Leu Pro Pro Lys Gly Lys Leu Arg Ser Leu Cys Ser Gln His Val Glu
    210                 215                 220

Arg Leu Gln Ile Phe Gln His Leu His Pro Ile Val Val Gln Ala Ala
225                 230                 235                 240
```

```
Phe Pro Pro Leu Phe Lys Glu Leu Phe Ser Thr Glu Thr Glu Ser Pro
            245                 250                 255
Val Gly Leu Ser Lys
            260
```

ALKYL LINKED QUINOLINYL MODULATORS OF RORγT

CROSS-REFERENCE TO RELATED APPLICATIONS

This application claims priority from U.S. application Ser. No. 61/890,890, filed on Oct. 15, 2013, which is incorporated herein by reference.

FIELD OF THE INVENTION

The invention is directed to substituted quinoline compounds, which are modulators of the nuclear receptor RORγt, pharmaceutical compositions, and methods for use thereof. More particularly, the RORγt modulators are useful for preventing, treating or ameliorating an RORγt mediated inflammatory syndrome, disorder or disease.

BACKGROUND OF THE INVENTION

Retinoic acid-related nuclear receptor gamma t (RORγt) is a nuclear receptor, exclusively expressed in cells of the immune system, and a key transcription factor driving Th17 cell differentiation. Th17 cells are a subset of $CD4^+$ T cells, expressing CCR6 on their surface to mediate their migration to sites of inflammation, and dependent on IL-23 stimulation, through the IL-23 receptor, for their maintenance and expansion. Th17 cells produce several proinflammatory cytokines including IL-17A, IL-17F, IL-21, and IL-22 (Korn, T., E. Bettelli, et al. (2009). "IL-17 and Th17 Cells." Annu Rev Immunol 27: 485-517), which stimulate tissue cells to produce a panel of inflammatory chemokines, cytokines and metalloproteases, and promote recruitment of granulocytes (Kolls, J. K. and A. Linden (2004). "Interleukin-17 family members and inflammation." Immunity 21(4): 467-76; Stamp, L. K., M. J. James, et al. (2004). "Interleukin-17: the missing link between T-cell accumulation and effector cell actions in rheumatoid arthritis" Immunol Cell Biol 82(1): 1-9). Th17 cells have been shown to be the major pathogenic population in several models of autoimmune inflammation, including collagen-induced arthritis (CIA) and experimental autoimmune encephalomyelitis (EAE) (Dong, C. (2006). "Diversification of T-helper-cell lineages: finding the family root of IL-17-producing cells." Nat Rev Immunol 6(4): 329-33; McKenzie, B. S., R. A. Kastelein, et al. (2006). "Understanding the IL-23-IL-17 immune pathway." Trends Immunol 27(1): 17-23). RORγt-deficient mice are healthy and reproduce normally, but have shown impaired Th17 cell differentiation in vitro, a significantly reduced Th17 cell population in vivo, and decreased susceptibility to EAE (Ivanov, II, B. S. McKenzie, et al. (2006). "The orphan nuclear receptor RORgammat directs the differentiation program of proinflammatory IL-17+ T helper cells." Cell 126(6): 1121-33). Mice deficient for IL-23, a cytokine required for Th17 cell survival, fail to produce Th17 cells and are resistant to EAE, CIA, and inflammatory bowel disease (IBD) (Cua, D. J., J. Sherlock, et al. (2003). "Interleukin-23 rather than interleukin-12 is the critical cytokine for autoimmune inflammation of the brain." Nature 421(6924): 744-8; Langrish, C. L., Y. Chen, et al. (2005). "IL-23 drives a pathogenic T cell population that induces autoimmune inflammation." J Exp Med 201(2): 233-40; Yen, D., J. Cheung, et al. (2006). "IL-23 is essential for T cell-mediated colitis and promotes inflammation via IL-17 and IL-6." J Clin Invest 116(5): 1310-6). Consistent with these findings, an anti-IL23-specific monoclonal antibody blocks development of psoriasis-like inflammation in a murine disease model (Tonel, G., C. Conrad, et al. "Cutting edge: A critical functional role for IL-23 in psoriasis." J Immunol 185(10): 5688-91).

In humans, a number of observations support the role of the IL-23/Th17 pathway in the pathogenesis of inflammatory diseases. IL-17, the key cytokine produced by Th17 cells, is expressed at elevated levels in a variety of allergic and autoimmune diseases (Barczyk, A., W. Pierzchala, et al. (2003). "Interleukin-17 in sputum correlates with airway hyperresponsiveness to methacholine." Respir Med 97(6): 726-33; Fujino, S., A. Andoh, et al. (2003). "Increased expression of interleukin 17 in inflammatory bowel disease." Gut 52(1): 65-70; Lock, C., G. Hermans, et al. (2002). "Gene-microarray analysis of multiple sclerosis lesions yields new targets validated in autoimmune encephalomyelitis." Nat Med 8(5): 500-8; Krueger, J. G., S. Fretzin, et al. "IL-17A is essential for cell activation and inflammatory gene circuits in subjects with psoriasis." J Allergy Clin Immunol 130(1): 145-154 e9). Furthermore, human genetic studies have shown association of polymorphisms in the genes for Th17 cell-surface receptors, IL-23R and CCR6, with susceptibility to IBD, multiple sclerosis (MS), rheumatoid arthritis (RA) and psoriasis (Gazouli, M., I. Pachoula, et al. "NOD2/CARD15, ATG16L1 and IL23R gene polymorphisms and childhood-onset of Crohn's disease." World J Gastroenterol 16(14): 1753-8., Nunez, C., B. Dema, et al. (2008). "IL23R: a susceptibility locus for celiac disease and multiple sclerosis?" Genes Immun 9(4): 289-93; Bowes, J. and A. Barton "The genetics of psoriatic arthritis: lessons from genome-wide association studies." Discov Med 10(52): 177-83; Kochi, Y., Y. Okada, et al. "A regulatory variant in CCR6 is associated with rheumatoid arthritis susceptibility." Nat Genet 42(6): 515-9).

Ustekinumab (Stelara®), an anti-p40 monoclonal antibody blocking both IL-12 and IL-23, is approved for the treatment of adult patients (18 years or older), with moderate to severe plaque psoriasis, who are candidates for phototherapy or systemic therapy. Currently, monoclonal antibodies specifically targeting only IL-23, to more selectively inhibit the Th17 subset, are also in clinical development for psoriasis (Garber K. (2011). "Psoriasis: from bed to bench and back" Nat Biotech 29, 563-566), further implicating the important role of the IL-23- and RORγt-driven Th17 pathway in this disease. Results from recent phase II clinical studies strongly support this hypothesis, as anti-IL-17 receptor and anti-IL-17 therapeutic antibodies both demonstrated high levels of efficacy in patients with chronic psoriasis (Papp, K. A., "Brodalumab, an anti-interleukin-17-receptor antibody for psoriasis." N Engl J Med 2012 366(13): 1181-9; Leonardi, C., R. Matheson, et al. "Anti-interleukin-17 monoclonal antibody ixekizumab in chronic plaque psoriasis." N Engl J Med 366(13): 1190-9). Anti-IL-17 antibodies have also demonstrated clinically relevant responses in early trials in RA and uveitis (Hueber, W., Patel, D. D., Dryja, T., Wright, A. M., Koroleva, I., Bruin, G., Antoni, C., Draelos, Z., Gold, M. H., Durez, P., Tak, P. P., Gomez-Reino, J. J., Foster, C. S., Kim, R. Y., Samson, C. M., Falk, N. S., Chu, D. S., Callanan, D., Nguyen, Q. D., Rose, K., Haider, A., Di Padova, F. (2010) Effects of AIN457, a fully human antibody to interleukin-17A, on psoriasis, rheumatoid arthritis, and uveitis. Sci Transl Med 2, 5272).

All the above evidence supports inhibition of the Th17 pathway by modulating RORγt activity as an effective strategy for the treatment of immune-mediated inflammatory diseases.

SUMMARY OF THE INVENTION

The present invention comprises compounds of Formula I.

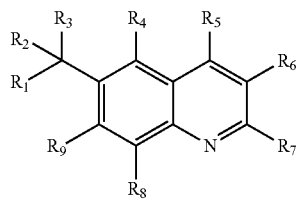

Formula I $R^1$ is azetidinyl, pyrrolyl, pyrazolyl, imidazolyl, triazolyl, thiazolyl, pyridyl, pyridyl N-oxide, pyrazinyl, pyrimidinyl, pyridazyl, piperidinyl, quinazolinyl, cinnolinyl, benzothiazolyl, indazolyl, tetrahydropyranyl, tetrahydrofuranyl, furanyl, phenyl, oxazolyl, isoxazolyl, thiophenyl, benzoxazolyl, benzimidazolyl, indolyl, thiadiazolyl, oxadiazolyl, or quinolinyl; wherein said piperidinyl, pyridyl, pyridyl N-oxide, pyrimidinyl, pyridazyl, pyrazinyl, quinazolinyl, cinnolinyl, benzothiazolyl, indazolyl, imidazolyl, phenyl, thiophenyl, benzoxazolyl, benzimidazolyl, indolyl, quinolinyl, and pyrazolyl are optionally substituted with $C(O)C_{(1-4)}$alkyl (including $C(O)CH_3$), $C(O)NH_2$, $C(O)NHC_{(1-2)}$alkyl, $C(O)N(C_{(1-2)}alkyl)_2$, $NHC(O)C_{(1-4)}$alkyl, $NHSO_2C_{(1-4)}$alkyl, $C_{(1-4)}$alkyl, $CF_3$, $CH_2CF_3$, Cl, F, —CN, $OC_{(1-4)}$alkyl (including $OCH_3$), $N(C_{(1-4)}alkyl)_2$ (including $N(CH_3)_2$, —$(CH_2)_3OCH_3$, $SC_{(1-4)}$alkyl, OH, $CO_2H$, $CO_2C_{(1-4)}$alkyl, $C(O)CF_3$, $SO_2CF_3$, $OCF_3$, $OCHF_2$, $SO_2CH_3$, $SO_2NH_2$, $SO_2NHC_{(1-2)}$alkyl, $SO_2N(C_{(1-2)}alkyl)_2$, $C(O)NHSO_2CH_3$, or $OCH_2OCH_3$; and optionally substituted with up to two additional substituents independently selected from the group consisting of Cl, $C_{(1-2)}$alkyl (including $CH_3$), $SCH_3$, $OC_{(1-2)}$alkyl (including $OCH_3$), $CF_3$, —CN, and F; and wherein said triazolyl, oxazolyl, isoxazolyl, pyrrolyl, and thiazolyl are optionally substituted with up to two substituents independently selected from the group consisting of $SO_2CH_3$, $SO_2NH_2$, $C(O)NH_2$, —CN, $OC_{(1-2)}$alkyl, $(CH_2)_{(2-3)}OCH_3$, $SCH_3$, $CF_3$, F, Cl, and $C_{(1-2)}$alkyl (including $CH_3$); and said thiadiazolyl and oxadiazolyl are optionally substituted with $C_{(1-2)}$alkyl; and said pyridyl, pyridyl-N-oxide, pyrimidinyl, pyridazyl, and pyrazinyl are optionally substituted with up to three additional substituents independently selected from the group consisting of $C(O)NHC_{(1-2)}$alkyl, $C(O)N(C_{(1-2)}alkyl)_2$, $NHC(O)C_{(1-4)}$alkyl, $NHSO_2C_{(1-4)}$alkyl, $C(O)CF_3$, $SO_2CF_3$, $SO_2NHC_{(1-2)}$alkyl, $SO_2N(C_{(1-2)}alkyl)_2$, $C(O)NHSO_2CH_3$, $SO_2CH_3$, $SO_2NH_2$, $C(O)NH_2$, —CN, $OC_{(1-4)}$alkyl, $(CH_2)_{(2-3)}OCH_3$, $SC_{(1-4)}$alkyl, $CF_3$, F, Cl, and $C_{(1-4)}$alkyl; and wherein said azetidinyl is optionally substituted with $C_{(1-3)}$alkyl, $C(O)C_{(1-2)}$alkylOH, $C(O)NH_2$, $CO_2C(CH_3)_3$, $SO_2CH_3$, or $C(O)CH_3$;

$R^2$ is $C_{(1-6)}$alkyl, $C_{(3-6)}$cycloalkyl (including cyclopropyl), or alkynyl; wherein said $C_{(1-6)}$alkyl or $C_{(3-6)}$cycloalkyl is optionally substituted with $NH_2$, $NHC_{(1-2)}$alkyl, $N(C_{(1-2)}alkyl)_2$, $SO_2C_{(1-2)}$alkyl, $SO_2NH_2$, $SO_2NHC_{(1-2)}$alkyl, $SO_2N(C_{(1-2)}alkyl)_2$, $CF_3$, COOH, $NHC(O)C_{(1-2)}$alkyl, $N(C_{(1-2)}alkyl)C(O)C_{(1-2)}$alkyl, $NHSO_2C_{(1-2)}$alkyl, $N(C_{(1-2)}alkyl)SO_2C_{(1-2)}$alkyl, $C(O)NHC_{(1-2)}$alkyl, $C(O)N(C_{(1-2)}alkyl)_2$, OH, —CN, $OCF_3$, $OCHF_2$, $C(O)NH_2$, $OC_{(1-4)}$alkyl, or up to three fluorine atoms; and wherein said alkynyl is optionally substituted with $C_{(1-3)}$alkyl;

$R^3$ is H, OH, $OCH_3$, or $NH_2$;

$R^4$ is H, or F;

$R^5$ is H, Cl, —CN, $CF_3$, $SC_{(1-4)}$alkyl, $OC_{(1-4)}$alkyl, OH, $C_{(1-4)}$alkyl (including $OCH_3$), $N(CH_3)OCH_3$, $NH(C_{(1-4)}$alkyl), $N(C_{(1-4)}alkyl)_2$ (including $N(CH_3)_2$), 4-hydroxypiperidinyl, azetidin-1-yl, or fur-2-yl; provided that $R^5$ may not be H if $R^7$ is $OCH_3$;

$R^6$ is pyridyl, pyrimidinyl, pyridazyl, pyrazinyl, thiazolyl, isothiazolyl, furanyl, thiophenyl, oxazolyl, isoxazolyl, imidazolyl, pyrazolyl, pyrrolyl, triazolyl, oxadiazolyl, thiadiazolyl, or phenyl, any of which is optionally substituted with up to two substituents independently selected from the group consisting of piperidinyl, pyrrolidinyl, azetidinyl, pyrazolyl, triazolyl, imidazolyl, —CN, $C_{(1-4)}$alkyl (including $CH_3$), $OC_{(1-4)}$alkyl, $C(O)C_{(1-4)}$alkyl, $CO_2H$, $CO_2C_{(1-4)}$alkyl, $NH_2$, $NHC_{(1-2)}$alkyl, $N(C_{(1-2)}alkyl)_2$, $SO_2NH_2$, $SONH_2$, $SO_2NHC_{(1-2)}$alkyl, $SON(CH_3)_2$, $SO_2N(C_{(1-2)}alkyl)_2$, $SCH_3$, $OCH_2CF_3$, $SO_2CH_3$, $CF_3$, Cl, F, OH, and $OCF_3$; or $R^6$ is —O-phenyl, —NHphenyl, —$N(C_{(1-3)}alkyl)$phenyl, —$N(CO_2C(CH_3)_3)$phenyl, $N(COCH_3)$phenyl, —O-pyridyl, —NHpyridyl, —$N(C_{(1-3)}alkyl)$pyridyl, $N(CO_2C(CH_3)_3)$pyridyl, $N(COCH_3)$pyridyl, —O-pyrimidinyl, —NHpyrimidinyl, —$N(C_{(1-3)}alkyl)$pyrimidinyl, $N(CO_2C(CH_3)_3)$pyrimidinyl, $N(COCH_3)$pyrimidinyl, —O-pyridazyl, —NHpyridazyl, —$N(C_{(1-3)}alkyl)$pyridazyl, $N(CO_2C(CH_3)_3)$pyridazyl, $N(COCH_3)$pyridazyl, —O-pyrazinyl, —NHpyrazinyl, —$N(C_{(1-3)}alkyl)$pyrazinyl, $N(CO_2C(CH_3)_3)$pyrazinyl, or $N(COCH_3)$pyrazinyl; wherein said pyrimidinyl portions thereof, pyridazyl portions thereof, or pyrazinyl portions thereof are optionally substituted with Cl, F, $CH_3$, $SCH_3$, $OC_{(1-4)}$alkyl, —CN, $CONH_2$, $SO_2NH_2$, or $SO_2CH_3$; and wherein said phenyl portions thereof or said pyridyl portions thereof are optionally substituted with up to two substituents independently selected from the group consisting of $OCF_3$, $SO_2C_{(1-4)}$alkyl, $CF_3$, $CHF_2$, pyrazolyl, triazolyl, imidazolyl, tetrazolyl, oxazolyl, thiazolyl, $C_{(1-4)}$alkyl, $C_{(3-4)}$cycloalkyl, $OC_{(1-4)}$alkyl, $N(CH_3)_2$, $SO_2NH_2$, $SO_2NHCH_3$, $SO_2N(CH_3)_2$, $CONH_2$, $CONHCH_3$, $CON(CH_3)_2$, Cl, F, —CN, $CO_2H$, OH, $CH_2OH$, $NHCOC_{(1-2)}$alkyl, $COC_{(1-2)}$alkyl, $SCH_3$, $CO_2C_{(1-4)}$alkyl, $NH_2$, $NHC_{(1-2)}$alkyl, and $OCH_2CF_3$; and wherein said pyrazolyl, triazolyl, imidazolyl, tetrazolyl, oxazolyl, and thiazolyl are optionally further substituted with $CH_3$; or $R^6$ is —$CH_2R^6$, wherein $R^6$ is pyridyl, phenyl, benzothiophenyl, thiophenyl, pyrimidinyl, pyridazyl, or pyrazinyl; wherein said pyrimidinyl, pyridazyl, or pyrazinyl are optionally substituted with Cl, F, $CH_3$, $SCH_3$, $OC_{(1-4)}$alkyl, —CN, $CONH_2$, $SO_2NH_2$, or $SO_2CH_3$; and wherein said pyridyl or phenyl is optionally substituted with up to two substituents independently selected from the group consisting of $OCF_3$, $SO_2C_{(1-4)}$alkyl, $CF_3$, $CHF_2$, pyrazolyl, triazolyl, imidazolyl, tetrazolyl, oxazolyl, thiazolyl, $C_{(1-4)}$alkyl, $C_{(3-4)}$cycloalkyl, $OC_{(1-4)}$alkyl (including $OCH_3$), $N(CH_3)_2$, $SO_2NH_2$, $SO_2NHCH_3$, $SO_2N(CH_3)_2$, $CONH_2$, $CONHCH_3$, $CON(CH_3)_2$, Cl, F, —CN, $CO_2H$, OH, $CH_2OH$, $NHCOC_{(1-2)}$alkyl, $COC_{(1-2)}$alkyl, $SCH_3$, $CO_2C_{(1-4)}$alkyl, $NH_2$, $NHC_{(1-2)}$alkyl, and $OCH_2CF_3$; and wherein said pyrazolyl, triazolyl, imidazolyl, tetrazolyl, oxazolyl, and thiazolyl are optionally further substituted with $CH_3$;

$R^7$ is H, Cl, —CN, $C_{(1-4)}$alkyl, $OC_{(1-4)}$alkyl$CF_3$, $OCF_3$, $OCHF_2$, $OCH_2CH_2OC_{(1-4)}$alkyl, $CF_3$, $SCH_3$, $C_{(1-4)}$alkyl$NA^1A^2$ (including $CH_2NA^1A^2$), $CH_2OC_{(2-3)}$alkyl$NA^1A^2$, $NA^1A^2$, $C(O)NA^1A^2$, $CH_2NHC_{(2-3)}$alkyl$NA^1A^2$, $CH_2N(CH_3)C_{(2-3)}$alkyl$NA^1A^2$, $NHC_{(2-3)}$ alkylNA$^1$A$^2$, N(CH$_3$)C$_{(2-4)}$alkylNA$^1$A$^2$, OC$_{(2-4)}$alkylNA$^1$A$^2$, OC$_{(1-4)}$alkyl (including OC$_{(1-2)}$alkyl), OCH$_2$-(1-methyl)-imidazol-2-yl, phenyl, thiophenyl, furyl, pyrazolyl, imidazolyl, pyridyl, pyridazyl, pyrazinyl, pyrimidinyl, indazolyl, phenyl, or wherein said phenyl, thiophenyl, furyl, pyrazolyl, imidazolyl, pyridyl, pyridazyl, pyrazinyl, pyrimidinyl, and indazolyl are optionally substituted with up to three substituents independently selected from the group consisting of F, Cl, CH$_3$, CF$_3$, and OCH$_3$;

A$^1$ is H or C$_{(1-4)}$alkyl (including OC$_{(1-2)}$alkyl);

A$^2$ is H, C$_{(1-4)}$alkyl (including OC$_{(1-2)}$alkyl), C$_{(1-4)}$alkylOC$_{(1-4)}$alkyl (including CH$_2$CH$_2$OCH$_3$), C$_{(1-4)}$alkylOH, C(O)C$_{(1-4)}$alkyl, or OC$_{(1-4)}$alkyl (including OCH$_3$); or A$^1$ and A$^2$ may be taken together with their attached nitrogen to form a ring selected from the group consisting of:

R$_a$ is H, OC$_{(1-4)}$alkyl, CH$_2$OH, NH(CH$_3$), N(CH$_3$)$_2$, NH$_2$, CH$_3$, F, CF$_3$, SO$_2$CH$_3$, or OH;

R$_b$ is H, CO$_2$C(CH$_3$)$_3$, C$_{(1-4)}$alkyl, C(O)C$_{(1-4)}$alkyl, SO$_2$C$_{(1-4)}$alkyl, CH$_2$CH$_2$CF$_3$, CH$_2$CF$_3$, CH$_2$-cyclopropyl, phenyl, CH$_2$-phenyl, or C$_{(3-6)}$cycloalkyl;

R$^8$ is H, C$_{(1-3)}$alkyl (including CH$_3$), OC$_{(1-3)}$alkyl (including OCH$_3$), CF$_3$, NH$_2$, NHCH$_3$, —CN, or F;

R$^9$ is H, or F;

and pharmaceutically acceptable salts thereof.

DETAILED DESCRIPTION OF THE INVENTION

The present invention comprises compounds of Formula I.

Formula I

R$^1$ is azetidinyl, pyrrolyl, pyrazolyl, imidazolyl, triazolyl, thiazolyl, pyridyl, pyridyl N-oxide, pyrazinyl, pyrimidinyl, pyridazyl, piperidinyl, quinazolinyl, cinnolinyl, benzothiazolyl, indazolyl, tetrahydropyranyl, tetrahydrofuranyl, furanyl, phenyl, oxazolyl, isoxazolyl, thiophenyl, benzoxazolyl, benzimidazolyl, indolyl, thiadiazolyl, oxadiazolyl, or quinolinyl; wherein said piperidinyl, pyridyl, pyridyl N-oxide, pyrimidinyl, pyridazyl, pyrazinyl, quinazolinyl, cinnolinyl, benzothiazolyl, indazolyl, imidazolyl, phenyl, thiophenyl, benzoxazolyl, benzimidazolyl, indolyl, quinolinyl, and pyrazolyl are optionally substituted with $C(O)C_{(1-4)}$ alkyl (including $C(O)CH_3$), $C(O)NH_2$, $C(O)NHC_{(1-2)}$ alkyl, $C(O)N(C_{(1-2)}alkyl)_2$, $NHC_{(1-4)}alkyl$, $NHSO_2C_{(1-4)}alkyl$, $C_{(1-4)}alkyl$, $CF_3$, $CH_2CF_3$, Cl, F, —CN, $OC_{(1-4)}alkyl$ (including $OCH_3$), $N(C_{(1-4)}alkyl)_2$ (including $N(CH_3)_2$, —$(CH_2)_3OCH_3$, $SC_{(1-4)}alkyl$, OH, $CO_2H$, $CO_2C_{(1-4)}alkyl$, $C(O)CF_3$, $SO_2CF_3$, $OCF_3$, $OCHF_2$, $SO_2CH_3$, $SO_2NH_2$, $SO_2NHC_{(1-2)}alkyl$, $SO_2N(C_{(1-2)}alkyl)_2$, $C(O)NHSO_2CH_3$, or $OCH_2OCH_3$; and optionally substituted with up to two additional substituents independently selected from the group consisting of Cl, $C_{(1-2)}alkyl$ (including $CH_3$), $SCH_3$, $OC_{(1-2)}alkyl$ (including $OCH_3$), $CF_3$, —CN, and F; and wherein said triazolyl, oxazolyl, isoxazolyl, pyrrolyl, and thiazolyl are optionally substituted with up to two substituents independently selected from the group consisting of $SO_2CH_3$, $SO_2NH_2$, $C(O)NH_2$, —CN, $OC_{(1-2)}alkyl$, $(CH_2)_{(2-3)}OCH_3$, $SCH_3$, $CF_3$, F, Cl, and $C_{(1-2)}alkyl$ (including $CH_3$); and said thiadiazolyl and oxadiazolyl are optionally substituted with $C_{(1-2)}alkyl$; and said pyridyl, pyridyl-N-oxide, pyrimidinyl, pyridazyl, and pyrazinyl are optionally substituted with up to three additional substituents independently selected from the group consisting of $C(O)NHC_{(1-2)}alkyl$, $C(O)N(C_{(1-2)}alkyl)_2$, $NHC(O)C_{(1-4)}alkyl$, $NHSO_2C_{(1-4)}alkyl$, $C(O)CF_3$, $SO_2CF_3$, $SO_2NHC_{(1-2)}alkyl$, $SO_2N(C_{(1-2)}alkyl)_2$, $C(O)NHSO_2CH_3$, $SO_2CH_3$, $SO_2NH_2$, $C(O)NH_2$, —CN, $OC_{(1-4)}alkyl$, $(CH_2)_{(2-3)}OCH_3$, $SC_{(1-4)}alkyl$, $CF_3$, F, Cl, and $C_{(1-4)}alkyl$; and wherein said azetidinyl is optionally substituted with $C_{(1-3)}alkyl$, $C(O)C_{(1-2)}alkylOH$, $C(O)NH_2$, $CO_2C(CH_3)_3$, $SO_2CH_3$, or $C(O)CH_3$;

$R^2$ is $C_{(1-6)}alkyl$, $C_{(3-5)}cycloalkyl$ (including cyclopropyl), or alkynyl; wherein said $C_{(1-6)}alkyl$ or $C_{(3-6)}cycloalkyl$ is optionally substituted with $NH_2$, $NHC_{(1-2)}alkyl$, $N(C_{(1-2)}alkyl)_2$, $SO_2C_{(1-2)}alkyl$, $SO_2NH_2$, $SO_2NHC_{(1-2)}alkyl$, $SO_2N(C_{(1-2)}alkyl)_2$, $CF_3$, COOH, $NHC(O)C_{(1-2)}alkyl$, $N(C_{(1-2)}alkyl)C(O)C_{(1-2)}alkyl$, $NHSO_2C_{(1-2)}alkyl$, $N(C_{(1-2)}alkyl)SO_2C_{(1-2)}alkyl$, $C(O)NHC_{(1-2)}alkyl$, $C(O)N(C_{(1-2)}alkyl)_2$, OH, —CN, $OCF_3$, $OCHF_2$, $C(O)NH_2$, $OC_{(1-4)}alkyl$, or up to three fluorine atoms; and wherein said alkynyl is optionally substituted with $C_{(1-3)}alkyl$;

$R^3$ is H, OH, $OCH_3$, or $NH_2$;

$R^4$ is H, or F;

$R^5$ is H, Cl, —CN, $CF_3$, $SC_{(1-4)}alkyl$, $OC_{(1-4)}alkyl$ (including $OCH_3$), OH, $C_{(1-4)}alkyl$, $N(CH_3)OCH_3$, $NH(C_{(1-4)}alkyl)$, $N(C_{(1-4)}alkyl)_2$ (including $N(CH_3)_2$), 4-hydroxypiperidinyl, azetidin-1-yl, or fur-2-yl; provided that $R^5$ may not be H if $R^7$ is $OCH_3$;

$R^6$ is pyridyl, pyrimidinyl, pyridazyl, pyrazinyl, thiazolyl, isothiazolyl, furanyl, thiophenyl, oxazolyl, isoxazolyl, imidazolyl, pyrazolyl, pyrrolyl, triazolyl, oxadiazolyl, thiadiazolyl, or phenyl, any of which is optionally substituted with up to two substituents independently selected from the group consisting of piperidinyl, pyrrolidinyl, azetidinyl, pyrazolyl, triazolyl, imidazolyl, —CN, $C_{(1-4)}alkyl$ (including $CH_3$), $OC_{(1-4)}alkyl$, $C(O)C_{(1-4)}alkyl$, $CO_2H$, $CO_2C_{(1-4)}alkyl$, $NH_2$, $NHC_{(1-2)}alkyl$, $N(C_{(1-2)}alkyl)_2$, $SO_2NH_2$, $SONH_2$, $SO_2NHC_{(1-2)}alkyl$, $SON(CH_3)_2$, $SO_2N(C_{(1-2)}alkyl)_2$, $SCH_3$, $OCH_2CF_3$, $SO_2CH_3$, $CF_3$, Cl, F, OH, and $OCF_3$; or $R^6$ is —O-phenyl, —NHphenyl, —$N(C_{(1-3)}alkyl)phenyl$, —$N(CO_2C(CH_3)_3)phenyl$, $N(COCH_3)phenyl$, —O-pyridyl, —NHpyridyl, —$N(C_{(1-3)}alkyl)pyridyl$, $N(CO_2C(CH_3)_3)pyridyl$, $N(COCH_3)pyridyl$, —O-pyrimidinyl, —NHpyrimidinyl, —$N(C_{(1-3)}alkyl)pyrimidinyl$, $N(CO_2C(CH_3)_3)pyrimidinyl$, $N(COCH_3)pyrimidinyl$, —O-pyridazyl, —NHpyridazyl, —$N(C_{(1-3)}alkyl)pyridazyl$, $N(CO_2C(CH_3)_3)pyridazyl$, $N(COCH_3)pyridazyl$, —O-pyrazinyl, —NHpyrazinyl, —$N(C_{(1-3)}alkyl)pyrazinyl$, $N(CO_2C(CH_3)_3)pyrazinyl$, or $N(COCH_3)pyrazinyl$; wherein said pyrimidinyl portions thereof, pyridazyl portions thereof, or pyrazinyl portions thereof are optionally substituted with Cl, F, $CH_3$, $SCH_3$, $OC_{(1-4)}alkyl$, —CN, $CONH_2$, $SO_2NH_2$, or $SO_2CH_3$; and wherein said phenyl portions thereof or said pyridyl portions thereof are optionally substituted with up to two substituents independently selected from the group consisting of $OCF_3$, $SO_2C_{(1-4)}alkyl$, $CF_3$, $CHF_2$, pyrazolyl, triazolyl, imidazolyl, tetrazolyl, oxazolyl, thiazolyl, $C_{(1-4)}alkyl$, $C_{(3-4)}cycloalkyl$, $OC_{(1-4)}alkyl$, $N(CH_3)_2$, $SO_2NH_2$, $SO_2NHCH_3$, $SO_2N(CH_3)_2$, $CONH_2$, $CONHCH_3$, $CON(CH_3)_2$, Cl, F, —CN, $CO_2H$, OH, $CH_2OH$, $NHCOC_{(1-2)}alkyl$, $COC_{(1-2)}alkyl$, $SCH_3$, $CO_2C_{(1-4)}alkyl$, $NH_2$, $NHC_{(1-2)}alkyl$, and $OCH_2CF_3$; and wherein said pyrazolyl, triazolyl, imidazolyl, tetrazolyl, oxazolyl, and thiazolyl are optionally further substituted with $CH_3$; or $R^6$ is —$CH_2R^6$, wherein $R^6$ is pyridyl, phenyl, benzothiophenyl, thiophenyl, pyrimidinyl, pyridazyl, or pyrazinyl; wherein said pyrimidinyl, pyridazyl, or pyrazinyl are optionally substituted with Cl, F, $CH_3$, $SCH_3$, $OC_{(1-4)}alkyl$, —CN, $CONH_2$, $SO_2NH_2$, or $SO_2CH_3$; and wherein said pyridyl or phenyl is optionally substituted with up to two substituents independently selected from the group consisting of $OCF_3$, $SO_2C_{(1-4)}alkyl$, $CF_3$, $CHF_2$, pyrazolyl, triazolyl, imidazolyl, tetrazolyl, oxazolyl, thiazolyl, $C_{(1-4)}alkyl$, $C_{(3-4)}cycloalkyl$, $OC_{(1-4)}alkyl$ (including $OCH_3$), $N(CH_3)_2$, $SO_2NH_2$, $SO_2NHCH_3$, $SO_2N(CH_3)_2$, $CONH_2$, $CONHCH_3$, $CON(CH_3)_2$, Cl, F, —CN, $CO_2H$, OH, $CH_2OH$, $NHCOC_{(1-2)}alkyl$, $COC_{(1-2)}alkyl$, $SCH_3$, $CO_2C_{(1-4)}alkyl$, $NH_2$, $NHC_{(1-2)}alkyl$, and $OCH_2CF_3$; and wherein said pyrazolyl, triazolyl, imidazolyl, tetrazolyl, oxazolyl, and thiazolyl are optionally further substituted with $CH_3$;

$R^7$ is H, Cl, —CN, $C_{(1-4)}alkyl$, $OC_{(1-4)}alkylCF_3$, $OCF_3$, $OCHF_2$, $OCH_2CH_2OC_{(1-4)}alkyl$, $CF_3$, $SCH_3$, $C_{(1-4)}alkylNA^1A^2$ (including $CH_2NA^1A^2$), $CH_2OC_{(2-3)}alkylNA^1A^2$, $NA^1A^2$, $C(O)NA^1A^2$, $CH_2NHC_{(2-3)}alkylNA^1A^2$, $CH_2N(CH_3)C_{(2-3)}alkylNA^1A^2$, $NHC_{(2-3)}alkylNA^1A^2$, $N(CH_3)C_{(2-4)}alkylNA^1A^2$, $OC_{(2-4)}alkylNA^1A^2$, $OC_{(1-4)}alkyl$ (including $OC_{(1-2)}alkyl$), $OCH_2$-(1-methyl)-imidazol-2-yl, phenyl, thiophenyl, furyl, pyrazolyl, imidazolyl, pyridyl, pyridazyl, pyrazinyl, pyrimidinyl, indazolyl, phenyl, or

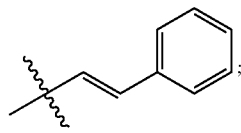 [SMILES: */C=C/c1ccccc1]

wherein said phenyl, thiophenyl, furyl, pyrazolyl, imidazolyl, pyridyl, pyridazyl, pyrazinyl, pyrimidinyl, and indazolyl are optionally substituted with up to three substituents independently selected from the group consisting of F, Cl, $CH_3$, $CF_3$, and $OCH_3$;

$A^1$ is H or $C_{(1-4)}alkyl$ (including $OC_{(1-2)}alkyl$);

$A^2$ is H, $C_{(1-4)}alkyl$ (including $OC_{(1-2)}alkyl$), $C_{(1-4)}alkylOC_{(1-4)}alkyl$ (including $CH_2CH_2OCH_3$), $C_{(1-4)}alkylOH, C(O)C$_{(1-4)}$alkyl, or OC$_{(1-4)}$alkyl (including OCH$_3$); or A$^1$ and A$^2$ may be taken together with their attached nitrogen to form a ring selected from the group consisting of:

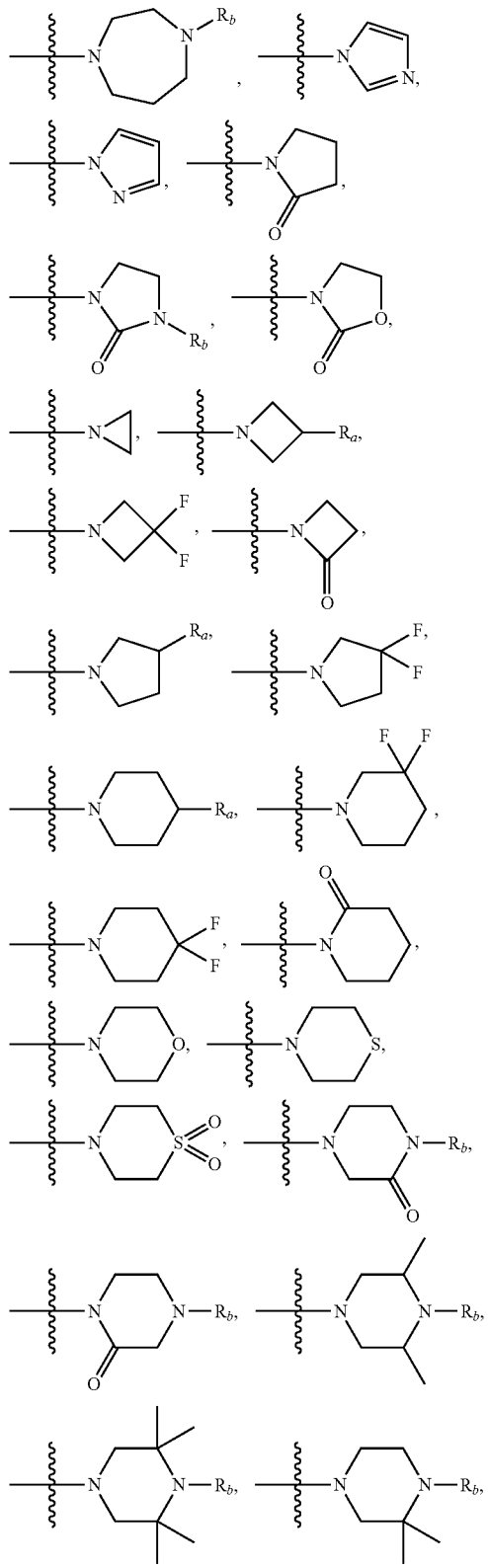

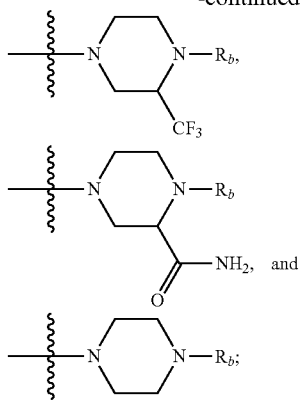

$R_a$ is H, OC$_{(1-4)}$alkyl, CH$_2$OH, NH(CH$_3$), N(CH$_3$)$_2$, NH$_2$, CH$_3$, F, CF$_3$, SO$_2$CH$_3$, or OH;

$R_b$ is H, CO$_2$C(CH$_3$)$_3$, C$_{(1-4)}$alkyl, C(O)C$_{(1-4)}$alkyl, SO$_2$C$_{(1-4)}$alkyl, CH$_2$CH$_2$CF$_3$, CH$_2$CF$_3$, CH$_2$-cyclopropyl, phenyl, CH$_2$-phenyl, or C$_{(3-6)}$cycloalkyl;

$R^8$ is H, C$_{(1-3)}$alkyl (including CH$_3$), OC$_{(1-3)}$alkyl (including OCH$_3$), CF$_3$, NH$_2$, NHCH$_3$, —CN, or F;

$R^9$ is H, or F;

and pharmaceutically acceptable salts thereof;

In another embodiment of the invention:

$R^1$ is azetidinyl, pyrrolyl, pyrazolyl, imidazolyl, triazolyl, thiazolyl, pyridyl, pyridyl N-oxide, pyrazinyl, pyrimidinyl, pyridazyl, piperidinyl, tetrahydropyranyl, phenyl, oxazolyl, isoxazolyl, thiophenyl, benzoxazolyl, or quinolinyl; wherein said piperidinyl, pyridyl, pyridyl N-oxide, imidazolyl, phenyl, thiophenyl, benzoxazolyl, and pyrazolyl are optionally substituted with SO$_2$CH$_3$, C(O)CH$_3$, C(O)NH$_2$, CH$_3$, CH$_2$CH$_3$, CF$_3$, Cl, F, —CN, OCH$_3$, N(CH$_3$)$_2$, —(CH$_2$)$_3$OCH$_3$, SCH$_3$, OH, CO$_2$H, CO$_2$C(CH$_3$)$_3$, or OCH$_2$OCH$_3$; and optionally substituted with up to two additional substituents independently selected from the group consisting of Cl, OCH$_3$, and CH$_3$; and wherein said triazolyl, oxazolyl, isoxazolyl, and thiazolyl are optionally substituted with one or two CH$_3$ groups; and wherein said azetidinyl is optionally substituted with CO$_2$C(CH$_3$)$_3$, SO$_2$CH$_3$, or C(O)CH$_3$;

$R^2$ is C$_{(1-6)}$alkyl (including CH$_3$, CH$_2$CH$_3$, CH(CH$_3$)$_2$, and CH$_2$CH$_2$CH$_2$CH$_3$), cyclopropyl, or alkynyl;

$R^3$ is H, OH, OCH$_3$, or NH$_2$;

$R^4$ is H, or F;

$R^5$ is H, Cl, —CN, CF$_3$, SCH$_3$, OC$_{(1-3)}$alkyl (including (OCH$_3$), OH, C$_{(1-4)}$alkyl (including CH$_3$), N(CH$_3$)OCH$_3$, NH(C$_{(1-2)}$alkyl), N(C$_{(1-2)}$alkyl)$_2$ (including N(CH$_3$)$_2$, 4-hydroxy-piperidinyl, azetidin-1-yl, or fur-2-yl; provided that R$^5$ may not be H if R$^7$ is OCH$_3$;

$R^6$ is pyridyl or phenyl, either of which is optionally substituted with Cl, F, CF$_3$, SO$_2$CH$_3$, —CN, or OCF$_3$; or R$^6$ is —O-phenyl, —NHphenyl, —N(C$_{(1-3)}$alkyl)phenyl, —N(CO$_2$C(CH$_3$)$_3$)phenyl, —O-pyridyl, —NHpyridyl, —N(C$_{(1-3)}$alkyl)pyridyl, or —N(CO$_2$C(CH$_3$)$_3$)pyridyl wherein said phenyl portions thereof or said pyridyl portions thereof are optionally substituted with OCF$_3$, SO$_2$CH$_3$, CF$_3$, CHF$_2$, imidazol-1-yl, pyrazol-1-yl, 1,2,4-triazol-1-yl, CH$_3$, OCH$_3$, Cl, F, or —CN; or R$^6$ is —CH$_2$R$^6$, wherein R$^6$ is pyridyl, phenyl, benzothiophenyl, or thiophenyl; wherein said pyridyl or phenyl is optionally substituted with OCF$_3$, SO$_2$CH$_3$, CF$_3$, CHF$_2$, imidazol-1-yl, pyrazol-1-yl, 1,2,4-triazol-1-yl, CH$_3$, OCH$_3$, Cl, F, or —CN;

R⁷ is H, Cl, —CN, C₍₁₋₄₎alkyl, OCH₂CF₃, OCH₂CH₂OCH₃, CF₃, SCH₃, NA¹A², C(O)NHCH₃, N(CH₃)CH₂CH₂NA¹A², OCH₂CH₂NA¹A², OC₍₁₋₃₎alkyl (including OC₍₁₋₂₎alkyl), OCH₂-(1-methyl)-imidazol-2-yl, imidazol-2-yl, fur-2-yl, pyrazol-4-yl, pyrid-3-yl, or pyrimidin-5-yl; thiophen-3-yl, 1-methyl-indazol-5-yl, 1-methyl-indazol-6-yl, phenyl, or

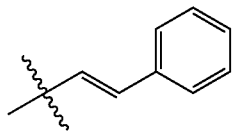 [SMILES: */C=C/c1ccccc1]

wherein said imidazolyl or pyrazolyl can be optionally substituted with a CH₃ group;

A¹ is H or C₍₁₋₄₎alkyl (including C₍₁₋₂₎alkyl);
A² is H, C₍₁₋₄₎alkyl (including C₍₁₋₂₎alkyl), C₍₁₋₄₎alkyl OC₍₁₋₄₎alkyl (including CH₂CH₂OCH₃), C₍₁₋₄₎alkylOH, C(O)C₍₁₋₂₎alkyl, or OCH₃; or A¹ and A² may be taken together with their attached nitrogen to form a ring selected from the group consisting of:

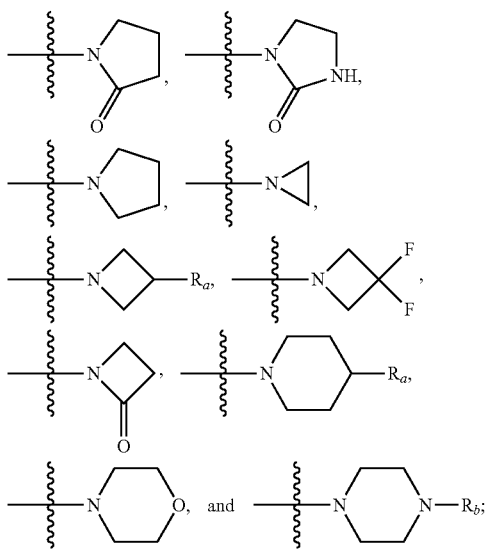

$R_a$ is H, F, OCH₃, or OH;
$R_b$ is CH₃, or phenyl;
R⁸ is H, CH₃, OCH₃, or F;
R⁹ is H, or F;
and pharmaceutically acceptable salts thereof;

In another embodiment of the invention
R¹ is azetidinyl, imidazolyl, pyrimidinyl, triazolyl, tetrahydropyranyl, thiazolyl, pyridyl, piperidinyl, phenyl, isoxazolyl, or oxazolyl; wherein said piperidinyl, pyridyl, imidazolyl, and phenyl are optionally substituted with SO₂CH₃, C(O)CH₃, CH₃, CF₃, Cl, F, —CN, OCH₃, or N(CH₃)₂; and optionally substituted with up to one additional group independently selected from Cl, OCH₃, and CH₃; and wherein said triazolyl, isoxazolyl, oxazolyl, and thiazolyl are optionally substituted with one or two CH₃ groups; and wherein said azetidinyl is optionally substituted with CO₂C(CH₃)₃, or C(O)CH₃;
R² is C₍₁₋₆₎alkyl (including CH₃, CH₂CH₃, CH(CH₃)₂, and CH₂CH₂CH₂CH₃), cyclopropyl, or alkynyl;

R³ is OH;
R⁴ is H;
R⁵ is Cl, —CN, CF₃, CH₃, OH, N(CH₃)OCH₃, N(CH₃)₂, azetidin-1-yl, or OCH₃;
R⁶ is pyridyl or phenyl, wherein said phenyl is optionally substituted with Cl, F, CF₃, SO₂CH₃, or OCF₃; or R⁶ is —O-phenyl, wherein said —O-phenyl is optionally substituted with Cl, F, or —CN; or R⁶ is —CH₂R⁶', wherein R⁶' is pyridyl, or phenyl, wherein said pyridyl or phenyl is optionally substituted with pyrazol-1-yl, 1,2,4-triazol-1-yl, CF₃, OCH₃, SO₂CH₃, Cl, F, or —CN;
R⁷ is Cl, —CN, C₍₁₋₄₎alkyl, OC₍₁₋₂₎alkyl (including OCH₃), or NA¹A²;
A¹ is C₍₁₋₂₎alkyl;
A² is C₍₁₋₂₎alkyl, CH₂CH₂OCH₃, or OCH₃; or A¹ and A² may be taken together with their attached nitrogen to form a ring selected from the group consisting of:

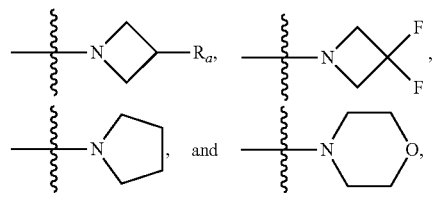

$R_a$ is OH, OCH₃, F;
R⁸ is H;
R⁹ is H;
and pharmaceutically acceptable salts thereof.

In another embodiment of the invention
R¹ is azetidin-3-yl, N-acetyl-azetidin-3-yl, N-Boc-azetidin-3-yl, 1-methyl-imidazol-5-yl, 1,2-dimethyl-imidazol-5-yl, 1-methyl-1,2,3-triazol-5-yl, 2,4-dimethyl-oxazol-5-yl, 3-methyl-isoxazol-5-yl, 2,4-dimethyl-thiazol-5-yl, 2,6-dimethyl-pyrid-3-yl;
R² is CH₃, CH₂CH₃, CH(CH₃)₂, CH₂CH₂CH₂CH₃, alkynyl, or cyclopropyl;
R³ is OH;
R⁴ is H;
R⁵ is Cl;
R⁶ is phenyl; or R⁶ is —CH₂R⁶, wherein R⁶ is phenyl; wherein said phenyl is optionally substituted with SO₂CH₃, or CF₃;
R⁷ is Cl, or OCH₃;
R⁸ is H;
R⁹ is H;
and pharmaceutically acceptable salts thereof.

Another embodiment of the invention is a compound selected from the group consisting of:

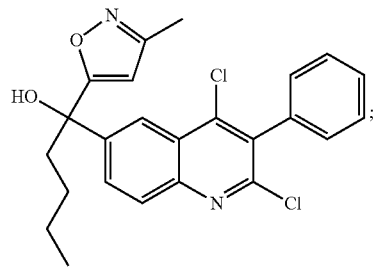

-continued
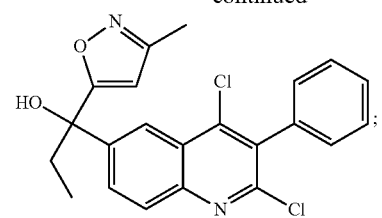
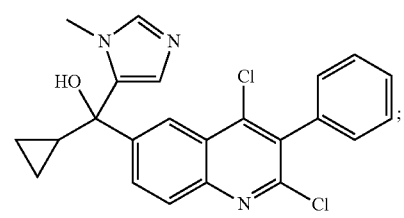
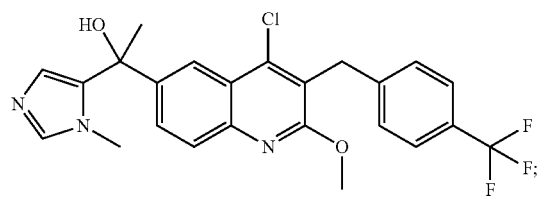
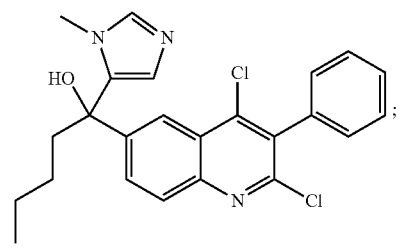
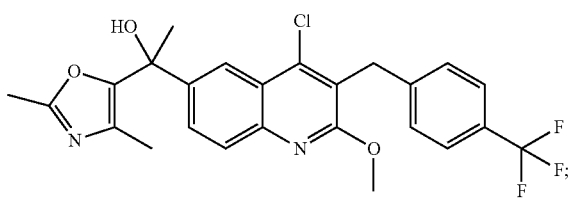
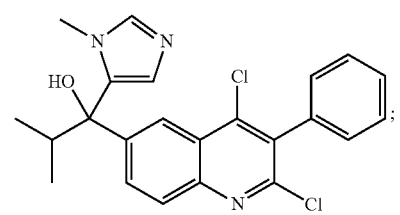
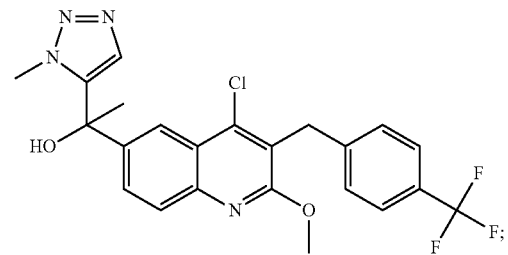
-continued
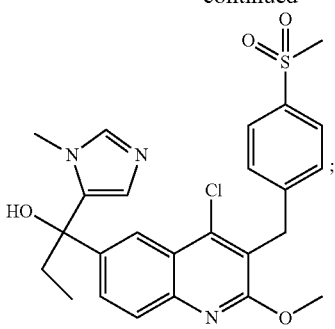
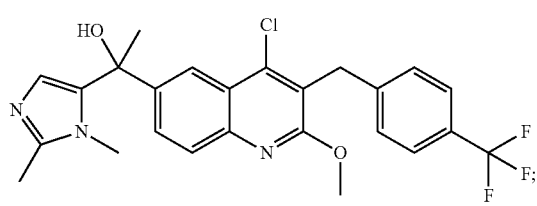
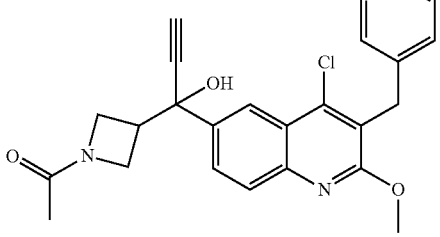
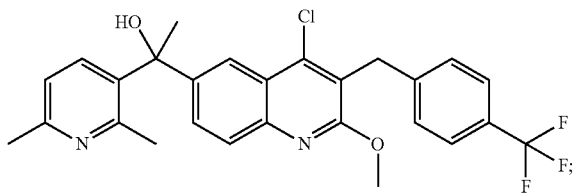
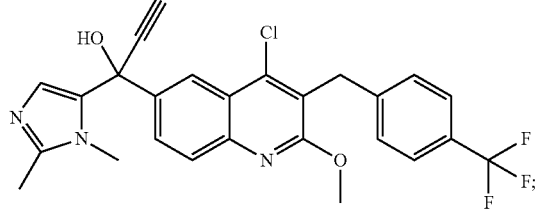
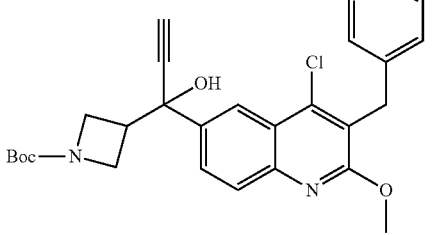

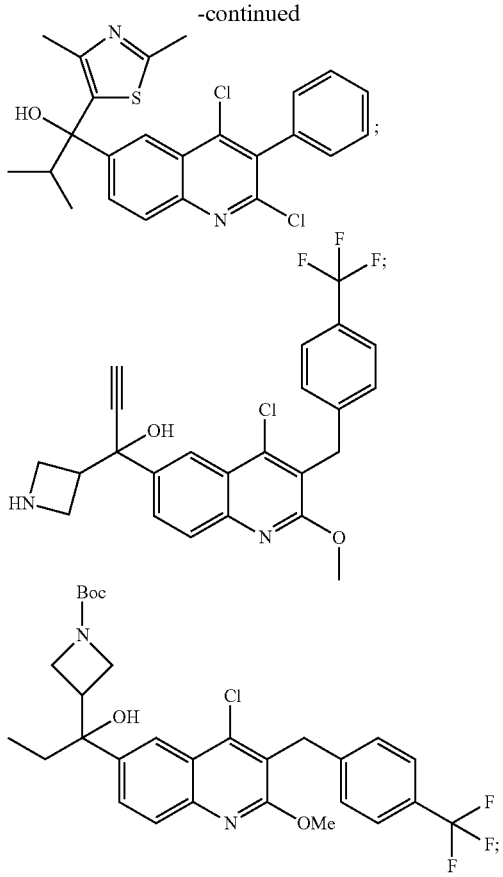

and pharmaceutically acceptable salts thereof.

Another embodiment of the invention comprises a compound of Formula I and a pharmaceutically acceptable carrier.

The present invention also provides a method for preventing, treating or ameliorating an RORγt mediated inflammatory syndrome, disorder or disease comprising administering to a subject in need thereof an effective amount of a compound of Formula I or a form, composition or medicament thereof.

The present invention provides a method of preventing, treating or ameliorating a syndrome, disorder or disease, wherein said syndrome, disorder or disease is selected from the group consisting of: ophthalmic disorders, uveitis, atherosclerosis, rheumatoid arthritis, psoriasis, psoriatic arthritis, atopic dermatitis, multiple sclerosis, Crohn's Disease, ulcerative colitis, ankylosing spondylitis, nephritis, organ allograft rejection, fibroid lung, systic fibrosis, renal insufficiency, diabetes and diabetic complications, diabetic nephropathy, diabetic retinopathy, diabetic retinitis, diabetic microangiopathy, tuberculosis, chronic obstructive pulmonary disease, sarcoidosis, invasive staphylococcia, inflammation after cataract surgery, allergic rhinitis, allergic conjunctivitis, chronic urticaria, systemic lupus erythematosus, asthma, allergic asthma, steroid resistant asthma, neutrophilic asthma, periodontal diseases, periodonitis, gingivitis, gum disease, diastolic cardiomyopathies, cardiac infarction, myocarditis, chronic heart failure, angiostenosis, restenosis, reperfusion disorders, glomerulonephritis, solid tumors and cancers, chronic lymphocytic leukemia, chronic myelocytic leukemia, multiple myeloma, malignant myeloma, Hodgkin's disease, and carcinomas of the bladder, breast, cervix, colon, lung, prostate, or stomach comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: rheumatoid arthritis, psoriasis, chronic obstructive pulmonary disorder, psoriatic arthritis, ankylosing spondylitis, Crohn's disease, and ulcerative colitis.

The present invention provides a method of treating or ameliorating a syndrome, disorder or disease, wherein said syndrome, disorder or disease is selected from the group consisting of: rheumatoid arthritis, psoriasis, chronic obstructive pulmonary disorder, psoriatic arthritis, ankylosing spondylitis, Crohn's disease, and ulcerative colitis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: inflammatory bowel diseases, rheumatoid arthritis, psoriasis, chronic obstructive pulmonary disorder, psoriatic arthritis, ankylosing spondylitis, neutrophilic asthma, steroid resistant asthma, multiple sclerosis, and systemic lupus erythematosus comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: rheumatoid arthritis, and psoriasis comprising administering to a subject in need thereof an effective amount of a compound of Formula I or a form, composition or medicament thereof.

The present invention provides a method of treating or ameliorating a syndrome, disorder or disease, in a subject in need thereof comprising administering to the subject an effective amount of the compound of Formula I or composition or medicament thereof in a combination therapy with one or more anti-inflammatory agents, or immunosuppressive agents, wherein said syndrome, disorder or disease is selected from the group consisting of: rheumatoid arthritis, and psoriasis.

The present invention provides a method of treating or ameliorating a syndrome, disorder or disease, wherein said syndrome, disorder or disease is rheumatoid arthritis, comprising administering to a subject in need thereof an effective amount of a compound of Formula I or a form, composition or medicament thereof.

The present invention provides a method of treating or ameliorating a syndrome, disorder or disease, wherein said syndrome, disorder or disease is psoriasis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is chronic obstructive pulmonary disorder comprising administering to a subject in need thereof an effective amount of a compound of Formula I or a form, composition or medicament thereof.

The present invention provides a method of treating or ameliorating a syndrome, disorder or disease, wherein said syndrome, disorder or disease is psoriatic arthritis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is ankylosing spondylitis comprising administering to a subject in need thereof an effective amount of a compound of Formula I or a form, composition or medicament thereof.

The present invention provides a method of treating or ameliorating an inflammatory bowel disease, wherein said inflammatory bowel disease is Crohn's disease comprising administering to a subject in need thereof an effective amount of a compound of Formula I or a form, composition or medicament thereof.

The present invention provides a method of treating or ameliorating an inflammatory bowel disease, wherein said inflammatory bowel disease is ulcerative colitis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is neutrophilic asthma comprising administering to a subject in need thereof an effective amount of a compound of Formula I or a form, composition or medicament thereof.

The present invention provides a method of treating or ameliorating a syndrome, disorder or disease, wherein said syndrome, disorder or disease is steroid resistant asthma comprising administering to a subject in need thereof an effective amount of a compound of Formula I or a form, composition or medicament thereof.

The present invention provides a method of treating or ameliorating a syndrome, disorder or disease, wherein said syndrome, disorder or disease is multiple sclerosis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is systemic lupus erythematosus comprising administering to a subject in need thereof an effective amount of a compound of Formula I or a form, composition or medicament thereof.

The invention also relates to methods of modulating RORγt activity in a mammal by administration of an effective amount of at least one compound of Formula I.

DEFINITIONS

The term "administering" with respect to the methods of the invention, means a method for therapeutically or prophylactically preventing, treating or ameliorating a syndrome, disorder or disease as described herein by using a compound of Formula I or a form, composition or medicament thereof. Such methods include administering an effective amount of said compound, compound form, composition or medicament at different times during the course of a therapy or concurrently in a combination form. The methods of the invention are to be understood as embracing all known therapeutic treatment regimens.

The term "subject" refers to a patient, which may be an animal, typically a mammal, typically a human, which has been the object of treatment, observation or experiment and is at risk of (or susceptible to) developing a syndrome, disorder or disease that is associated with aberrant RORγt expression or RORγt overexpression, or a patient with an inflammatory condition that accompanies syndromes, disorders or diseases associated with aberrant RORγt expression or RORγt overexpression.

The term "effective amount" means that amount of active compound or pharmaceutical agent that elicits the biological or medicinal response in a tissue system, animal or human, that is being sought by a researcher, veterinarian, medical doctor, or other clinician, which includes preventing, treating or ameliorating the symptoms of a syndrome, disorder or disease being treated.

As used herein, the term "composition" is intended to encompass a product comprising the specified ingredients in the specified amounts, as well as any product which results, directly or indirectly, from combinations of the specified ingredients in the specified amounts.

The term "alkyl" refers to both linear and branched chain radicals of up to 12 carbon atoms, preferably up to 6 carbon atoms, unless otherwise indicated, and includes, but is not limited to, methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl. Any alkyl group may be optionally substituted with one $OCH_3$, one OH, or up to two fluorine atoms.

The term "$C_{(a-b)}$" (where a and b are integers referring to a designated number of carbon atoms) refers to an alkyl, alkenyl, alkynyl, alkoxy or cycloalkyl radical or to the alkyl portion of a radical in which alkyl appears as the prefix root containing from a to b carbon atoms inclusive. For example, $C_{(1-4)}$denotes a radical containing 1, 2, 3 or 4 carbon atoms.

The term "cycloalkyl" refers to a saturated or partially unsaturated monocyclic or bicyclic hydrocarbon ring radical derived by the removal of one hydrogen atom from a single ring carbon atom. Typical cycloalkyl radicals include cyclopropyl, cyclobutyl, cyclopentyl, cyclopentenyl, cyclohexyl, cyclohexenyl, cycloheptyl and cyclooctyl. Additional examples include $C_{(3-6)}$cycloalkyl, $C_{(5-8)}$cycloalkyl, decahydronaphthalenyl, and 2,3,4,5,6,7-hexahydro-1H-indenyl. Any cycloalkyl group may be optionally substituted with one $OCH_3$, one OH, or up to two fluorine atoms.

As used herein, the term "thiophenyl" is intended to describe the radical formed by removing a hydrogen atom from the molecule with the structure:

Pharmaceutically Acceptable Salts

Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid. Pharmaceutically acceptable basic/cationic salts include, and are not limited to aluminum, 2-amino-2-hydroxymethyl-propane-1,3-diol (also known as tris(hydroxymethyl)aminomethane, tromethane or "TRIS"), ammonia, benzathine, t-butylamine, calcium, calcium gluconate, calcium hydroxide, chloroprocaine, choline, choline bicarbonate, choline chloride, cyclohexylamine, diethanolamine, ethylenediamine, lithium, LiOMe, L-lysine, magnesium, meglumine, $NH_3$, $NH_4OH$, N-methyl-D-glucamine, piperidine, potassium, potassium-t-butoxide, potassium hydroxide (aqueous), procaine, quinine, sodium, sodium carbonate, sodium-2-ethylhexanoate, sodium hydroxide, triethanolamine, or zinc.

Methods of Use

The present invention is directed to a method for preventing, treating or ameliorating a RORγt mediated inflammatory syndrome, disorder or disease comprising administering to a subject in need thereof an effective amount of a compound of Formula I or a form, composition or medicament thereof.

Since RORγt is an N-terminal isoform of RORγ, it is recognized that compounds of the present invention which are modulators of RORγt are likely to be modulators of RORγ as well. Therefore the mechanistic description "RORγt modulators" is intended to encompass RORγ modulators as well.

When employed as RORγt modulators, the compounds of the invention may be administered in an effective amount within the dosage range of about 0.5 mg to about 10 g, preferably between about 0.5 mg to about 5 g, in single or divided daily doses. The dosage administered will be affected by factors such as the route of administration, the health, weight and age of the recipient, the frequency of the treatment and the presence of concurrent and unrelated treatments.

It is also apparent to one skilled in the art that the therapeutically effective dose for compounds of the present invention or a pharmaceutical composition thereof will vary according to the desired effect. Therefore, optimal dosages to be administered may be readily determined by one skilled in the art and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

The compounds of Formula I may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutically-acceptable salts of the compounds of Formula I include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

The present invention also encompasses a method of making a pharmaceutical composition comprising mixing a pharmaceutically acceptable carrier with any of the compounds of the present invention. Additionally, the present invention includes pharmaceutical compositions made by mixing a pharmaceutically acceptable carrier with any of the compounds of the present invention.

Polymorphs and Solvates

Furthermore, the compounds of the present invention may have one or more polymorph or amorphous crystalline forms and as such are intended to be included in the scope of the invention. In addition, the compounds may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like.

It is intended that the present invention include within its scope polymorphs and solvates of the compounds of the present invention. Thus, in the methods of treatment of the present invention, the term "administering" shall encompass the means for treating, ameliorating or preventing a syndrome, disorder or disease described herein with the compounds of the present invention or a polymorph or solvate thereof, which would obviously be included within the scope of the invention albeit not specifically disclosed.

In another embodiment, the invention relates to a compound as described in Formula I for use as a medicament.

In another embodiment, the invention relates to the use of a compound as described in Formula I for the preparation of a medicament for the treatment of a disease associated with an elevated or aberrant RORγt activity.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", Ed. H. Bundgaard, Elsevier, 1985.

Furthermore, it is intended that within the scope of the present invention, any element, in particular when mentioned in relation to a compound of Formula I, shall comprise all isotopes and isotopic mixtures of said element, either naturally occurring or synthetically produced, either with natural abundance or in an isotopically enriched form. For example, a reference to hydrogen includes within its scope $^{1}$H, $^{2}$H (D), and $^{3}$H (T). Similarly, references to carbon and oxygen include within their scope respectively $^{13}$C and $^{14}$C and $^{16}$O and $^{18}$O. The isotopes may be radioactive or non-radioactive. Radiolabelled compounds of Formula I may comprise a radioactive isotope selected from the group $^{3}$H, $^{11}$C, $^{18}$F, $^{122}$I, $^{123}$I, $^{125}$I, $^{131}$I, $^{75}$Br, $^{76}$Br, $^{77}$Br and $^{82}$Br. Preferably, the radioactive isotope is selected from the group of $^{3}$H, $^{11}$C and $^{18}$F.

Some compounds of the present invention may exist as atropisomers. Atropisomers are stereoisomers resulting from hindered rotation about single bonds where the steric strain barrier to rotation is high enough to allow for the isolation of the conformers. It is to be understood that all such conformers and mixtures thereof are encompassed within the scope of the present invention.

Where the compounds according to this invention have at least one stereocenter, they may accordingly exist as enantiomers or diastereomers. It is to be understood that all such isomers and mixtures thereof are encompassed within the scope of the present invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

ABBREVIATIONS

Herein and throughout the application, the following abbreviations may be used.
Å angstrom
Ac acetyl
Ac$_2$O acetic anhydride
Ar aryl
Boc tert-butyloxy carbonyl
BHT butylated hydroxytoluene
Bn benzyl
br broad
Bu butyl
n-BuLi n-butyl lithium
d doublet
dba dibenzylideneacetone
DCM dichloromethane
Dess-Martin periodinane 1,1,1-tris(acetyloxy)-1,1-dihydro-1,2-benziodoxol-3-(1H)-one
DMA dimethylacetamide
DMF N,N-dimethylformamide
DMSO dimethyl sulfoxide
dppf (diphenylphosphino)ferrocene
Eaton's Reagent 7.7 wt % phosphorus pentoxide solution in methanesulfonic acid
EDCI N-(3-dimethylaminopropyl)-N'-ethylcarbodiimide hydrochloride
ESI electrospray ionization
Et ethyl
Et$_2$O diethyl ether
EtOAc ethyl acetate
EtOH ethyl alcohol
FCC flash column chromatography
HATU O-(7-azabenzotriazol-1-yl)-N,N,N',N'-tetramethyluronium hexafluorophosphate
HPLC high pressure liquid chromatography
Hz hertz
i-PrOH isopropyl alcohol
KHMDS potassium bis(trimethylsilyl)amide
LCMS liquid chromatography-mass spectrometry
m multiplet
M molar (moles/liter)
Meldrum's acid 2,2-dimethyl-1,3-dioxane-4,6-dione
MeOH methanol
MHz megahertz
min minutes
mL milliliters
MTBE methyl tertiary butyl ether
MS mass spectrometry
m/z mass to charge ratio
nm nanometers
NaOiPr sodium isopropoxide
NMR nuclear magnetic resonance
Ph phenyl
PPA polyphosphoric acid
ppm parts per million
Pr propyl
q quartet
RP-HPLC reverse phase high pressure liquid chromatography
s singlet
s TEA triethylamine
TEMPO (2,2,6,6-tetramethylpiperidin-1-yl)oxidanyl
TFA trifluoroacetic acid
THF tetrahydrofuran
TLC thin layer chromatography
UV ultra-violet
X-Phos 2-dicyclohexylphosphino-2',4',6'-triisopropylbiphenyl General Schemes:

Compounds of Formula I in the present invention can be synthesized in accordance with the general synthetic methods known to those who are skilled in the art. The following reaction schemes are only meant to represent examples of the invention and are in no way meant to be a limit of the invention.

Scheme 1 describes method used to prepare 6-bromo or 6-iodo-quinolines of Formula IV wherein $R^6$ is Ar, —$CH_2Ar$, —OAr or $NA^5Ar$ wherein Ar is a phenyl ring or a heteroaryl ring as described in the detailed description of the invention and $A^5$ is H or alkyl. As shown in path 1, the 6-haloanilines II can be condensed with substituted malonic acids III in phosphorus oxychloride at temperatures between 80-120° C. affording 6-haloquinolines IV wherein $R^6$ is Ar or $CH_2Ar$ and $R^5$ and $R^7$ are Cl. The 2-substituted malonic acids III wherein $R^6$ is $CH_2Ar$, can be obtained through commercial sources or can be prepared by addition of benzaldehydes to Meldrum's acid or dialkyl malonates as described by D. B. Ramachary et al. (*Tetrahedron Letters* 47 (2006) 651-656) followed by aqueous base hydrolysis under either microwave conditions or by heating at temperatures between 100 and 115° C., or treatment with an acid such as trifluoracetic acid in water at temperatures ranging from room temperature to 100° C. Path 2 illustrates how one skilled in the art could generate 6-haloquinolines of Formula IV by cyclization of amides VI ($R^6$ is Ar, $CH_2Ar$, OAr or $NA^5Ar$ and $A^5$ is H or alkyl), derived from acylation of 4-haloanilines I with substituted acid chlorides V (X=Cl) or by coupling with substituted carboxylic acids V (X=OH) in the presence of an appropriate coupling agent such as EDCI or HATU and a base such as $Et_3N$. Acid chlorides V can be obtained through commercial sources or prepared from the corresponding carboxylic acid by procedures known to those skilled in the art. The amides can then be cyclized by in-situ formylation under Vilsmeier-Haack conditions ($POCl_3$/DMF) followed by heating to promote ring cyclization as described in WO2007014940 providing 2-chloroquinolines IV wherein $R^5$ is H and $R^7$ is Cl. Path 3 describes the acylation of methyl 2-aminobenzoates VII with acid chlorides V (X=Cl) or with substituted acids V (X=OH) using a coupling agent as previously described to form amide intermediates, which can be further treated with a base, such as sodium ethoxide, lithium bis(trimethylsilyl)amide or potassium bis(trimethylsilyl)amide, to afford 6-halo-4-hydroxyquinolin-2(1H)-ones VIII wherein $R^6$ is Ar, $CH_2Ar$, OAr or $NA^5Ar$ and $A^5$ is H or alkyl. Conversion of hydroxyquinolin-2(1H)-ones VIII to 2,4-dichloroquinolines IV can be carried out in refluxing phosphorus oxychloride.

Path 4 describes how one skilled in the art could generate 6-haloquinolines of Formula IV by condensation of anilines II and aldehydes IX in ethanol to form compounds of Formula X which can be further cyclized in polyphosphoric acid at high temperatures followed by treatment with phosphorus oxychloride as previously described to provide 6-haloquinolinones IV wherein $R^6$ is Ar, $R^5$ is Cl and $R^7$ is H. As illustrated in path 5, hydroxyquinolin-2(1H)-ones XI can be prepared by condensation of readily available 6-bromo or 6-iodoanilines with Meldrum's acid and then subsequently heated in the presence of Eaton's reagent or PPA as described by W. T. Gao, et al. (*Synthetic Communications* 2010, 40, 732). Condensation with substituted aldehydes of the formula ArCHO in the presence of a Hantzsch ester, such as diethyl 2,6-dimethyl-1,4-dihydropyridine-3,5-dicarboxylate, in solvents like ethanol or pyridine can afford substituted 6-halo-4-hydroxyquinolin-2(1H)-ones VIII wherein $R^6$ is $CH_2Ar$. Subsequent heating of quinolines VIII in the presence of phosphorus oxychloride at temperatures between 80-120° C. with or without a solvent, such as acetonitrile, can provide the 6-haloquinolines IV wherein $R^5$ and $R^7$ are Cl.

Scheme I

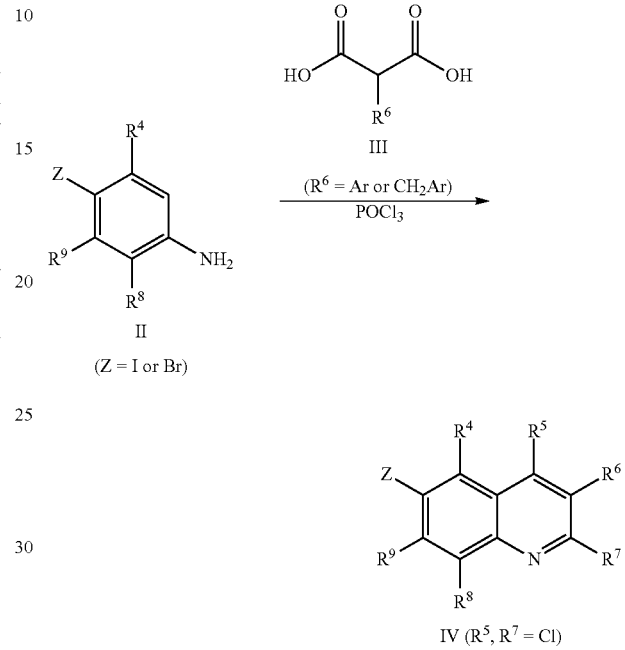

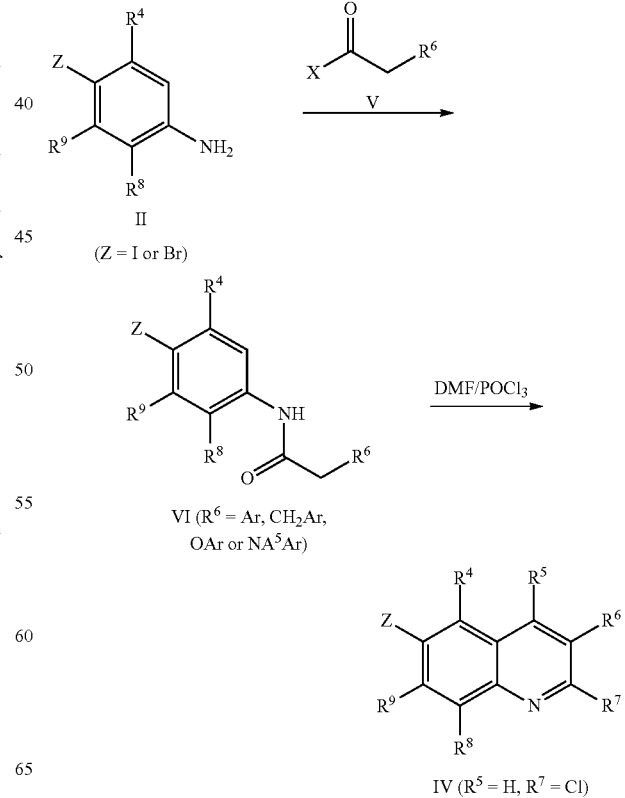

PATH 3
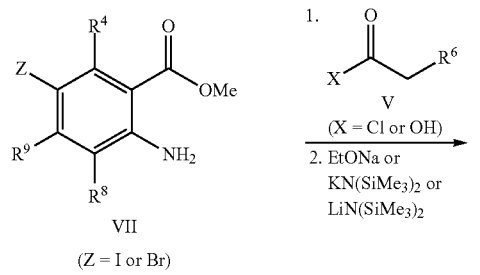
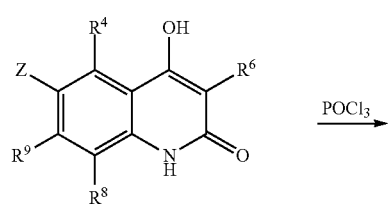
VIII (R⁶ = Ar, CH₂Ar, OAr or NA⁵Ar)
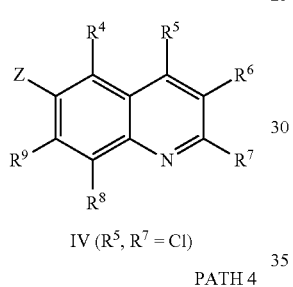
IV (R⁵, R⁷ = Cl)
PATH 4
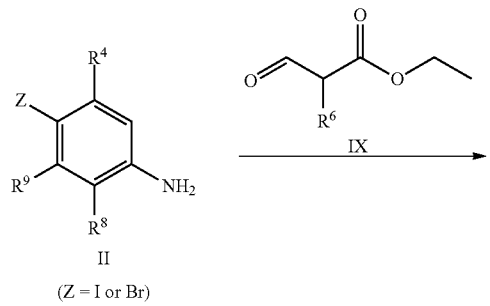
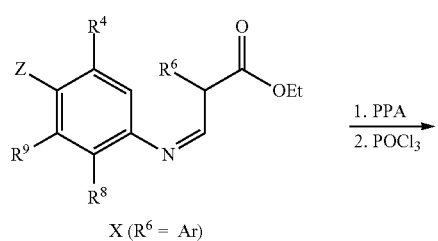
X (R⁶ = Ar)
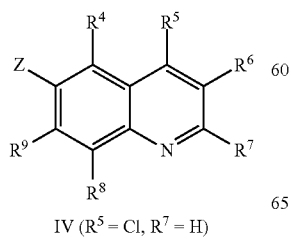
IV (R⁵ = Cl, R⁷ = H)
PATH 5
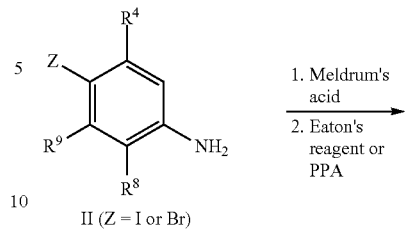
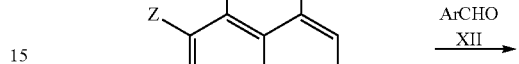
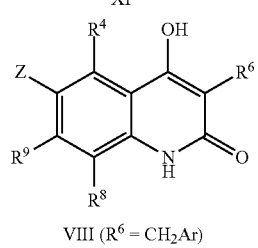
VIII (R⁶ = CH₂Ar)
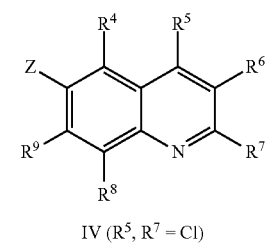
IV (R⁵, R⁷ = Cl)
PATH 6
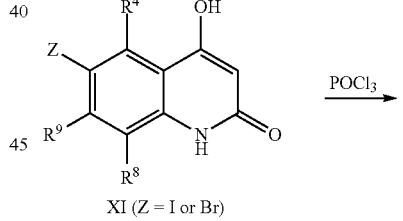
XI (Z = I or Br)
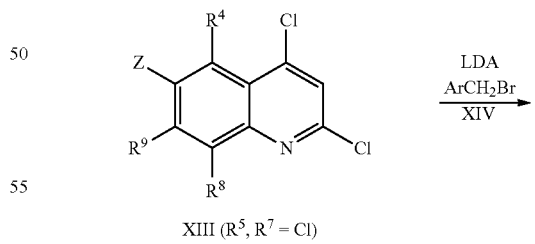
XIII (R⁵, R⁷ = Cl)
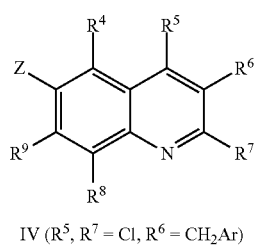
IV (R⁵, R⁷ = Cl, R⁶ = CH₂Ar)

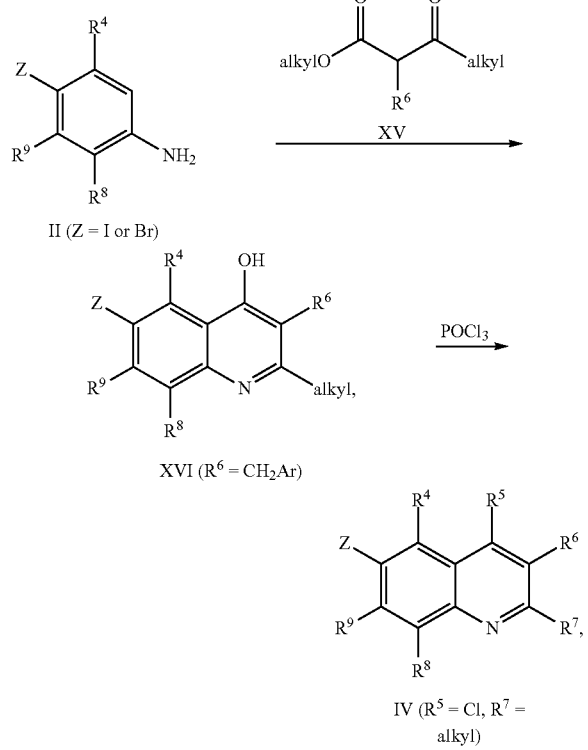

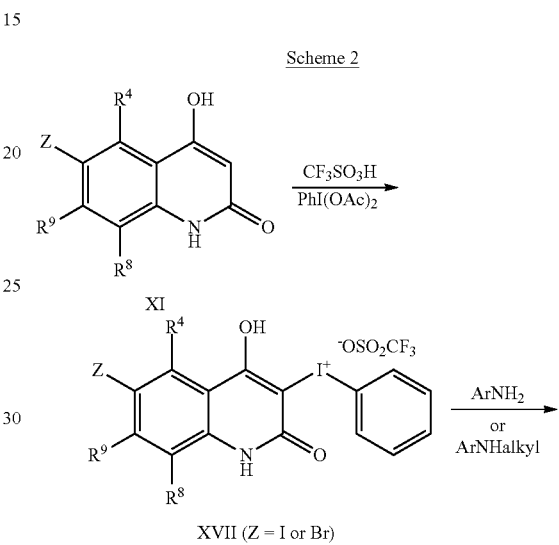

In path 6, hydroxyquinolin-2(1H)-ones XI can be transformed into the dichloroquinoline XIII with phosphorus oxychloride as described above. Deprotonation at the C3-position with a base such as lithium diisopropylamine in a solvent such as tetrahydrofuran at low temperatures such as −78° C. to 0° C. followed by addition of benzyl halide reagents XIV can provide 6-haloquinolines IV wherein $R^6$ is $CH_2Ar$ and both $R^5$ and $R^7$ are Cl.

Compounds of Formula IV, wherein $R^7$ is alkyl, can be prepared as illustrated in path 7. Intermediates of Formula XV can be prepared by deprotonation of β-keto esters, such as ethyl 3-oxobutanoate or ethyl 3-oxopentanoate, with a base like sodium hydride followed by alkylation with substituted alkyl halides. Intermediates of Formula XV can also be prepared by condensation of β-keto esters, such as ethyl 3-oxobutanoate or ethyl 3-oxopentanoate with aldehydes in the presence of piperidine and acetic acid in a solvent such as benzene followed by palladium catalyzed hydrogenation in a solvent such as ethanol. Condensation with 4-haloanilines II in the presence of an acid, such as para-toluenesulfonic acid (PTSA), in refluxing toluene with concomitant removal of water followed by intramolecular cyclization at elevated temperature affords 4-hydroxy quinolines XVI, wherein $R^7$ is alkyl. The hydroxyl group can then be converted to a chloro by heating in acetonitrile with phosphorus oxychloride to provide 6-haloquinolines IV wherein $R^5$ is Cl and $R^7$ is alkyl.

An alternative route that can be used to prepare 6-haloquinolines IV where $R^6$ is $NA^5Ar$ wherein Ar is phenyl or heteroaryl and $A^5$ is H, alkyl, $CO_2$alkyl or COalkyl is shown in Scheme 2. The 4-hydroxyquinolinones XI can be treated with (diacetoxyiodo)benzene and trifluoromethanesulfonic acid to yield 4-hydroxyquinolinone phenyliodoniumtrifluoromethane sulfonates XVII (Org. React. 2001, 57, 327). These intermediates can be treated with primary or secondary arylamines as described in Monatsh. Chem. 1984, 115 (2), 231 to provide the 4-hydroxyquinolinones VIII where $R^6$ is $NA^5Ar$ and $A^5$ is H or alkyl. Subsequent heating in phosphorus oxychloride as previously described could afford the 6-haloquinolines IV wherein $R^5$ and $R^7$ are chloro. Quinolines of Formula IV wherein $A^5$ is H can be further functionalized by N-alkylation or acylation with an alkyl halide or alkyl acid chloride to form amides IV ($R^6$ is $NA^5Ar$ and $A^5$ is alkyl or COalkyl). Quinolines of Formula IV wherein $A^5$ is H can also be treated with a dialkyl dicarbonate, such as di-tert-butyl dicarbonate, and DMAP in a polar solvent such as THF or DMF to form carbamates IV ($R^6$ is $NA^5Ar$ and $A^5$ is $CO_2$t-butyl).

Scheme 2

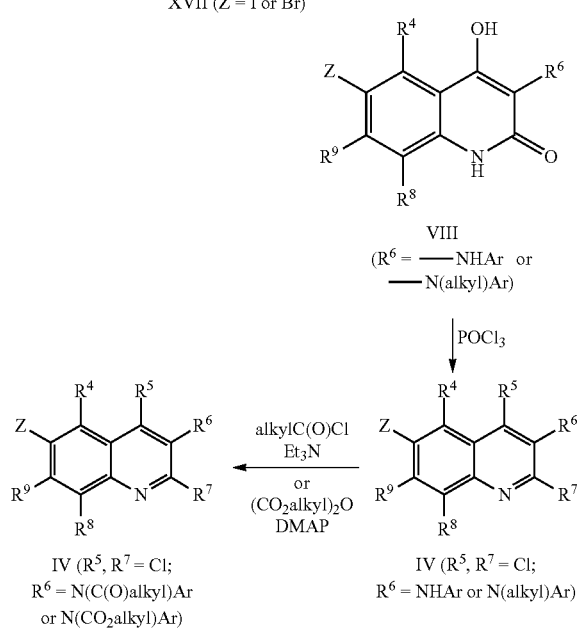

Scheme 3 illustrates how one skilled in the art could generate 6-haloquinolines of Formula IV wherein a $CF_3$ or $OCHF_2$ group is introduced at either 2, 4 or both 2 and 4 positions of the quinoline ring. As demonstrated in path 1, cyclization of 2-aminobenzoic acids XVIII with 1,1,1-trifluoropropan-2-ones XIX in Eaton's reagent at elevated temperatures could yield 4-hydroxy-2-trifluoromethylquinolines XX, which upon heating in phosphorus oxychloride at temperatures between 100-120° C. can give 6-haloquinolines IV, wherein $R^5$ is Cl and $R^7$ is $CF_3$. The quinolines IV wherein $R^5$ and $R^7$ are $CF_3$ could be formed by the reaction sequence illustrated in path 2. Treatment of 1-bromo-4-fluorobenzenes XXI with a base such as lithium diisopropylamide at temperatures between −78 and −40° C. followed by addition of ethyl trifluoroacetate can provide 2-fluorophenyl-2,2,2-trifluoroethanones XXII. Anilines XXIII could then be prepared by fluoride displacement with sodium azide followed by reduction with tin (II) chloride dihydrate. Cyclization of anilines XXIII with 1,1,1-trifluoropropan-2-ones XIX in the presence of tributylamine in a polar solvent, such as DMF or DMSO, at elevated temperatures can afford bromoquinolines IV wherein $R^5$ and $R^7$ are $CF_3$. Conversion of the 6-bromo to 6-iodoquinolines of Formula IV can then be accomplished with NaI, CuI, and N,N'-dimethylethylenediamine in a polar solvent such as t-BuOH at high temperatures under microwave conditions.

Acylation of anilines XXIII with acid chlorides or carboxylic acids and a coupling agent such as EDCI, in the presence of a base, such as triethylamine or potassium tert-butoxide, can lead directly to cyclized 4-(trifluoromethyl)quinolin-2(1H)-ones XXIV. Heating with phosphorus oxychloride with or without diisopropylethylamine yields 6-haloquinolines IV wherein $R^5$ is $CF_3$ and $R^7$ is Cl (path 3). Path 4 describes how one skilled in the art could generate compounds of Formula IV wherein $R^5$ is difluoromethoxy and $R^7$ is hydroxyl and compounds of Formula IV wherein both $R^5$ and $R^7$ are difluoromethoxy by treating hydroxyquinolin-2(1H)-ones VIII with 2-chloro-2,2-difluoroacetate and a base such as potassium carbonate in a polar aprotic solvent such as DMF. The 6-haloquinolin-2-one IV ($R^5$ is $OCHF_2$ and $R^7$ is OH) can be subsequently treated with phosphorus oxychloride as previously described to provide 6-haloquinolines IV wherein $R^5$ is difluoromethoxy and $R^7$ is Cl.

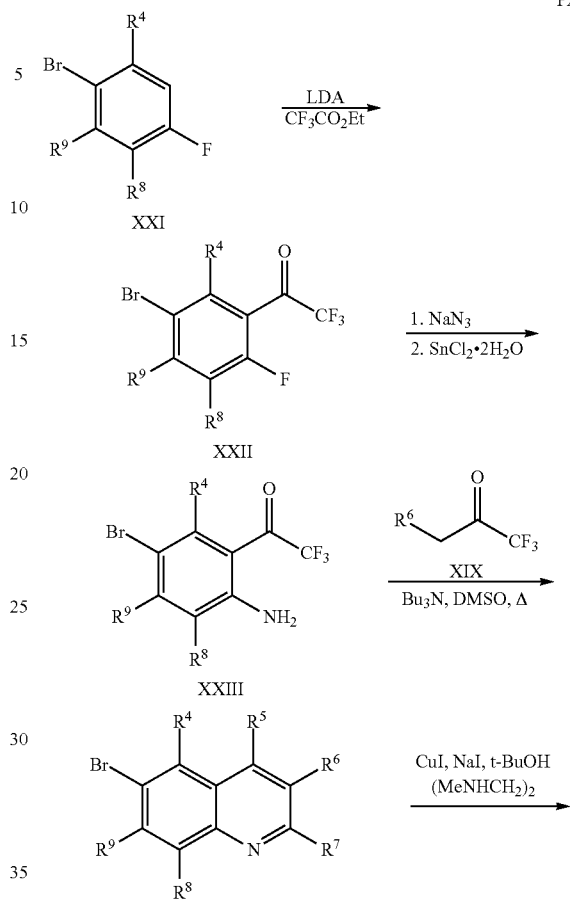

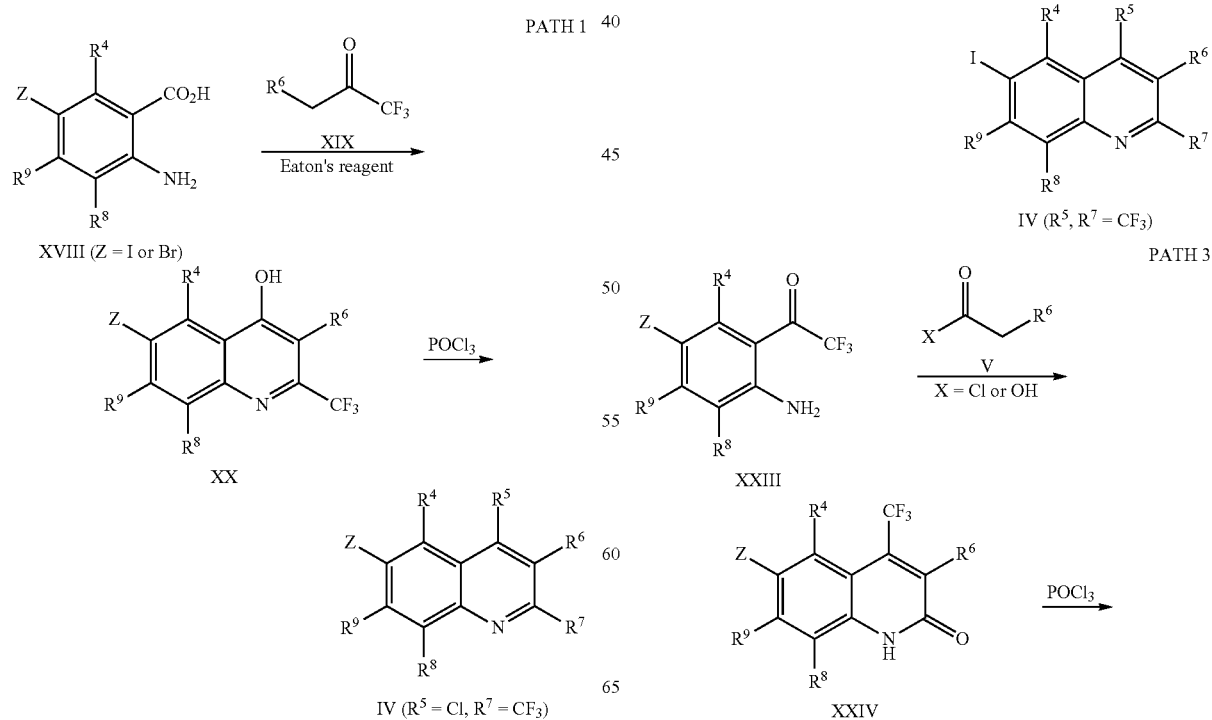

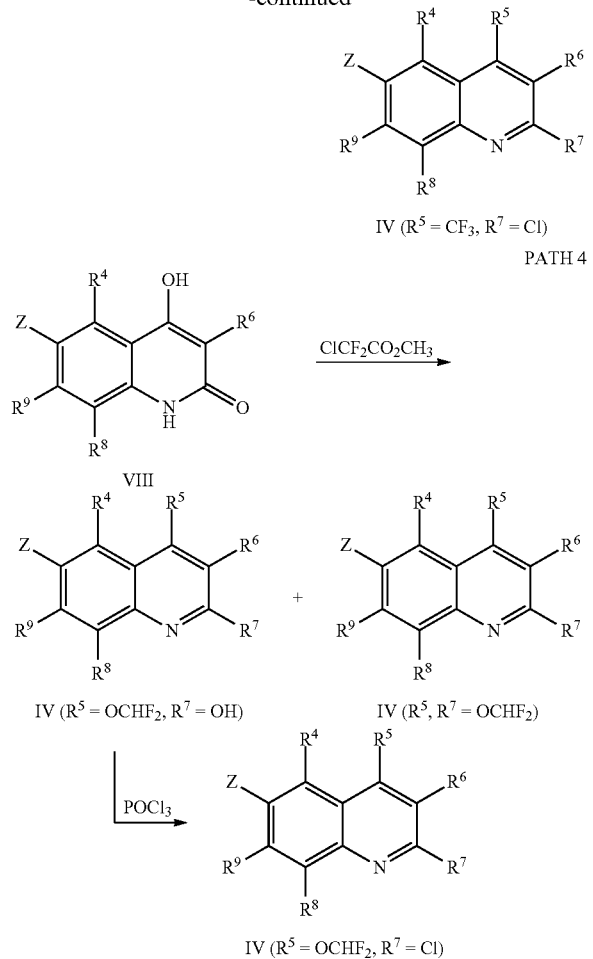

Scheme 4 illustrates alternative methods for the preparation of 6-haloquinoline intermediates VI wherein $R^6$ is $NA^5Ar$ or OAr and $R^7$ is hydrogen. Anilines II can be reacted with the in-situ generated methoxymethylene Meldrum's acid to form enamines XXV which can cyclize by heating in the range of 250-300° C. in a non-polar high-boiling solvent such as diphenyl ether, to provide 4-hydroxyquinolines XXVI (Madrid, P. B. et al., Bioorg. Med. Chem. Lett., 2005, 15, 1015). 4-Hydroxyquinolines XXVI may be nitrated at the 3-position by heating with nitric acid in an acidic solvent, such as propionic acid, to provide 3-nitro-4-hydroxyquinolines XXVII (path 1). Heating these intermediates with $POCl_3$ and reduction of the nitro group, for instance using tin (II) chloride dihydrate, provides 3-amino-4-chloroquinolines XXVIII. N-arylation or N-heteroarylation can be accomplished using aryl or heteroaryl boronic acids and a copper salt, such as $Cu(OAc)_2$, in the presence of a tertiary amine base. The resulting secondary amines can be further elaborated by N-alkylation or acylation with an alkyl halide or alkyl acid chloride and a base to provide 6-haloquinolines of Formula IV wherein $R^5$ is Cl, $R^7$ is H, $R^6$ is $NA^5Ar$ and $A^5$ is alkyl or COalkyl. Alternatively, 4-hydroxyquinolines XXVI may be brominated at the 3-position by heating with N-bromosuccinimide in acetic acid to furnish 3-bromo-4-hydroxyquinolines XXIX (path 2). Displacement of the 3-bromo substituent can be accomplished by heating with an aryl or heteroaryl potassium phenoxide salt in the presence of copper powder and copper (I) bromide in a polar solvent, such as DMF, as described in Collini, M. D. et al., US 20050131014. The resulting 4-hydroxyquinolines XXX can be heated in $POCl_3$ to provide 6-haloquinolines IV wherein $R^5$ is Cl, $R^7$ is H, $R^6$ is OAr.

Scheme 4

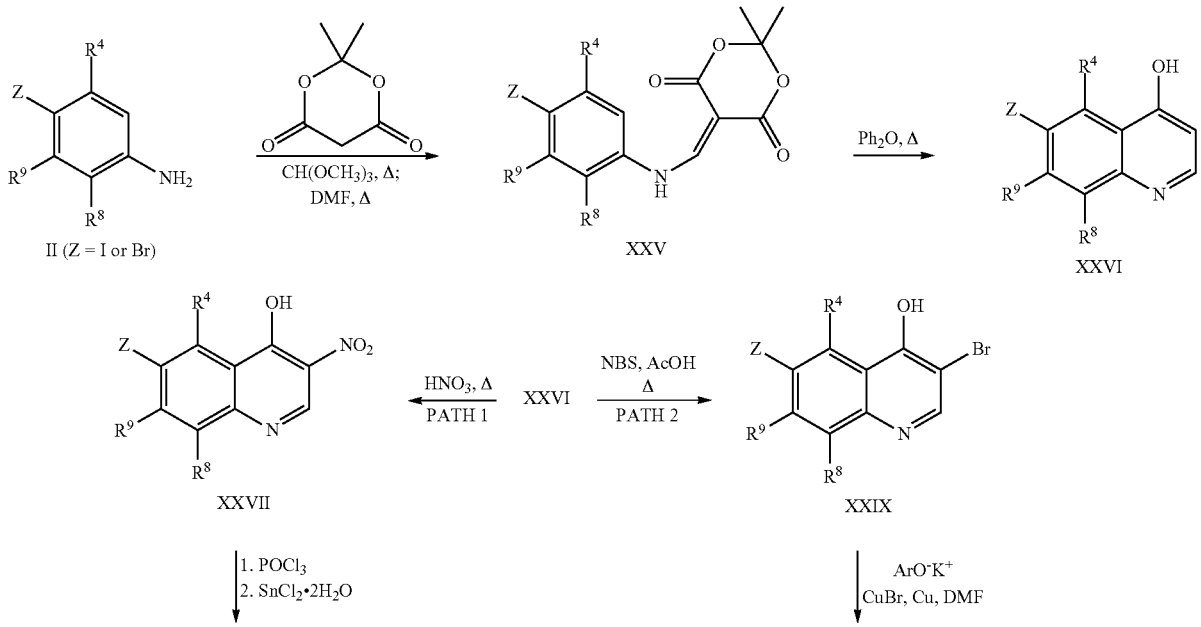

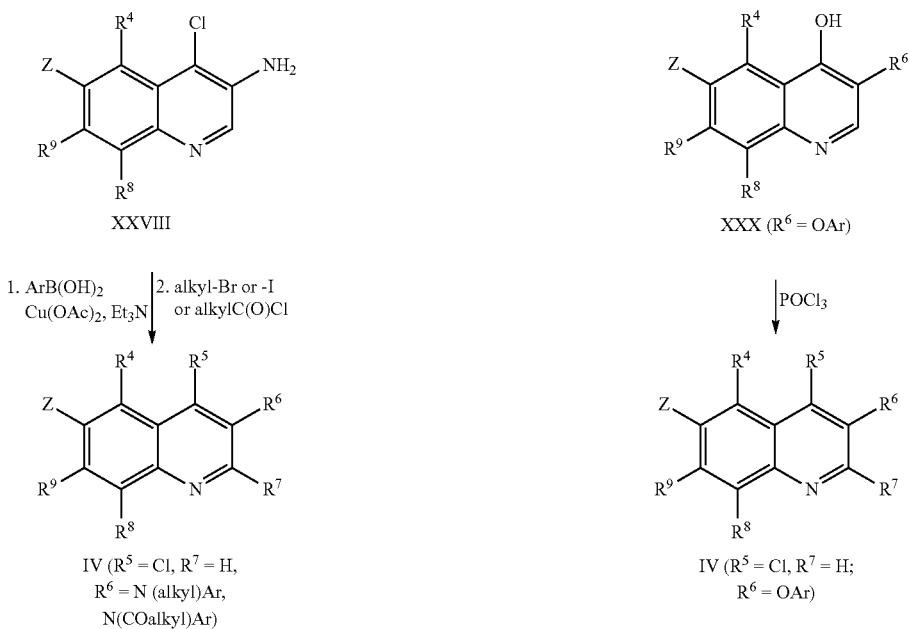

Scheme 5 provides methods used to displace the 2-Cl of 6-haloquinolines IV with oxygen or nitrogen neuclophiles. As shown in path 1, displacement of the 2-Cl with sodium alkoxides can be accomplished in an alcoholic solvent such as methanol, ethanol or isopropanol or at elevated temperatures or in a non-polar solvent such as toluene (Alan Osborne et al. *J. Chem. Soc. Perkin Trans.* 1 (1993) 181-184 and *J. Chem. Research* (S), 2002, 4) to provide substituted quinolines IV wherein, $R^7$ is Oalkyl. Likewise 6-haloquinolines of Formula IV where $R^7$ is $NA^1A^2$ can be obtained by displacement of the 2-Cl group with substituted amines using standard methods known in the art (path 2).

n-BuLi and trapped with dimethylformamide to provide aldehydes XXXII. Substituted carboxylic acids XXXIV can be treated with N,O-dimethylhydroxylamine hydrochloride in the presence of a base such as triethylamine or Hunig's base and a coupling reagent such as EDCI to provide the Weinreb amides XXXV (path 3). Acid chlorides XXXVI, which can be obtained through commercial sources or prepared from the corresponding carboxylic acid, can also be converted to the Weinreb amide XXXV using procedures known in the art (path 4).

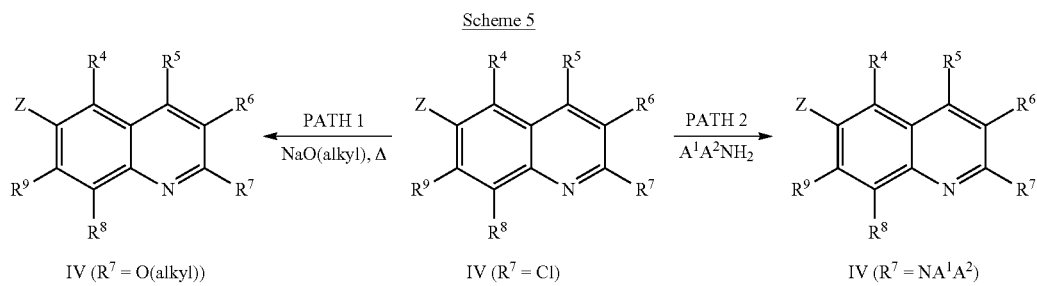

Scheme 6 depicts the synthesis of aldehydes of the Formula XXXII, which are not available through commercial sources, and Weinreb amides of Formula XXXV. As shown in path 1, aryl or heteroaryl halides XXXI are transformed into the corresponding organolithium or organomagnesium reagents with n-BuLi or a magnesium reagent, respectively, then trapped with dimethylformamide to provide aldehydes XXXII. Alternatively, as shown in path 2, heteroaryl rings XXXIII with an acidic proton can be deprotonated with

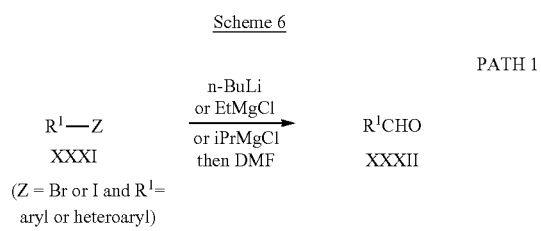

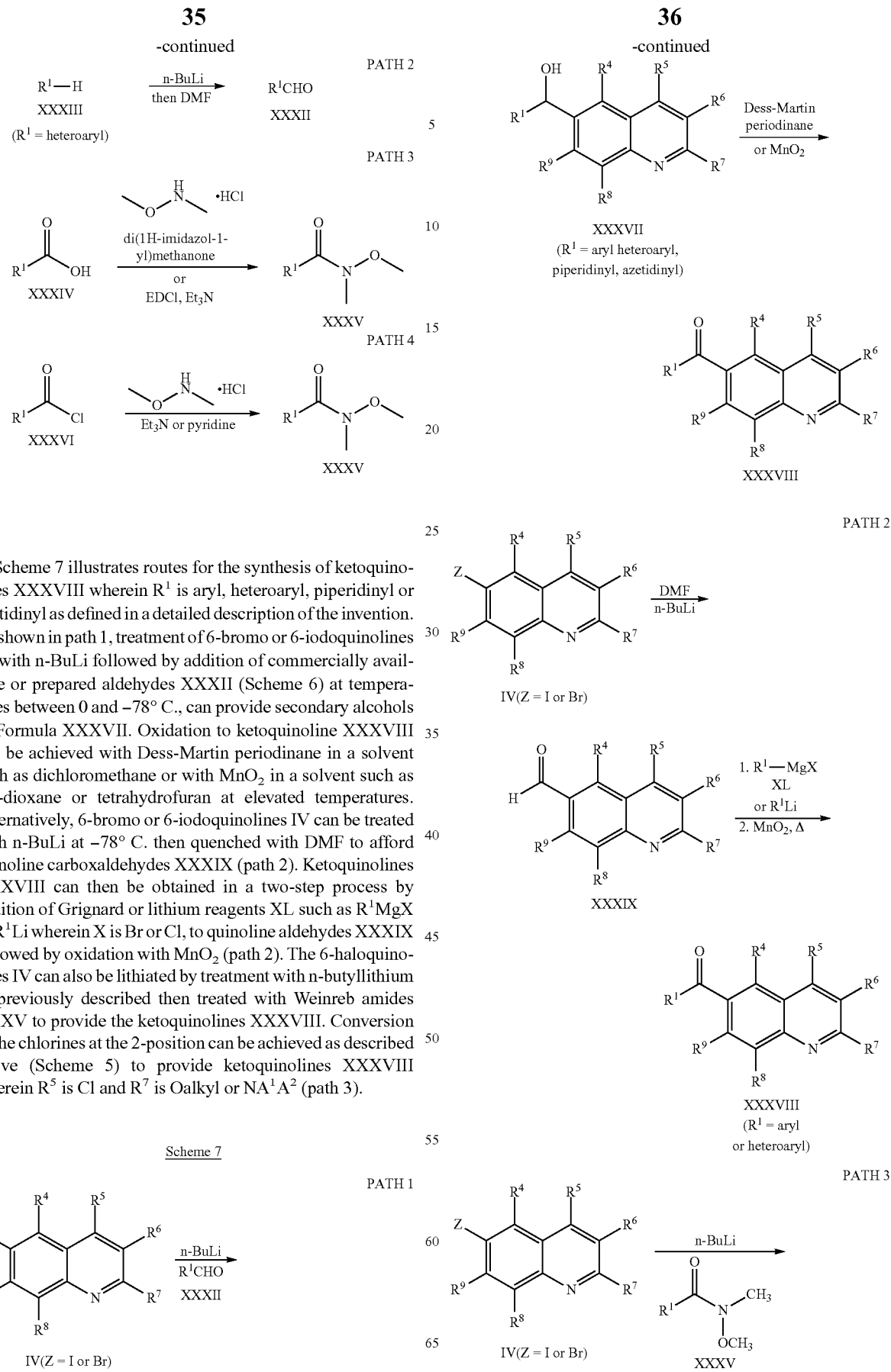

Scheme 7 illustrates routes for the synthesis of ketoquinolines XXXVIII wherein $R^1$ is aryl, heteroaryl, piperidinyl or azetidinyl as defined in a detailed description of the invention. As shown in path 1, treatment of 6-bromo or 6-iodoquinolines IV with n-BuLi followed by addition of commercially available or prepared aldehydes XXXII (Scheme 6) at temperatures between 0 and –78° C., can provide secondary alcohols of Formula XXXVII. Oxidation to ketoquinoline XXXVIII can be achieved with Dess-Martin periodinane in a solvent such as dichloromethane or with $MnO_2$ in a solvent such as 1,4-dioxane or tetrahydrofuran at elevated temperatures. Alternatively, 6-bromo or 6-iodoquinolines IV can be treated with n-BuLi at –78° C. then quenched with DMF to afford quinoline carboxaldehydes XXXIX (path 2). Ketoquinolines XXXVIII can then be obtained in a two-step process by addition of Grignard or lithium reagents XL such as $R^1MgX$ or $R^1Li$ wherein X is Br or Cl, to quinoline aldehydes XXXIX followed by oxidation with $MnO_2$ (path 2). The 6-haloquinolines IV can also be lithiated by treatment with n-butyllithium as previously described then treated with Weinreb amides XXXV to provide the ketoquinolines XXXVIII. Conversion of the chlorines at the 2-position can be achieved as described above (Scheme 5) to provide ketoquinolines XXXVIII wherein $R^5$ is Cl and $R^7$ is Oalkyl or $NA^1A^2$ (path 3).

Scheme 7

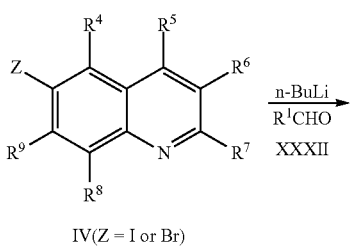

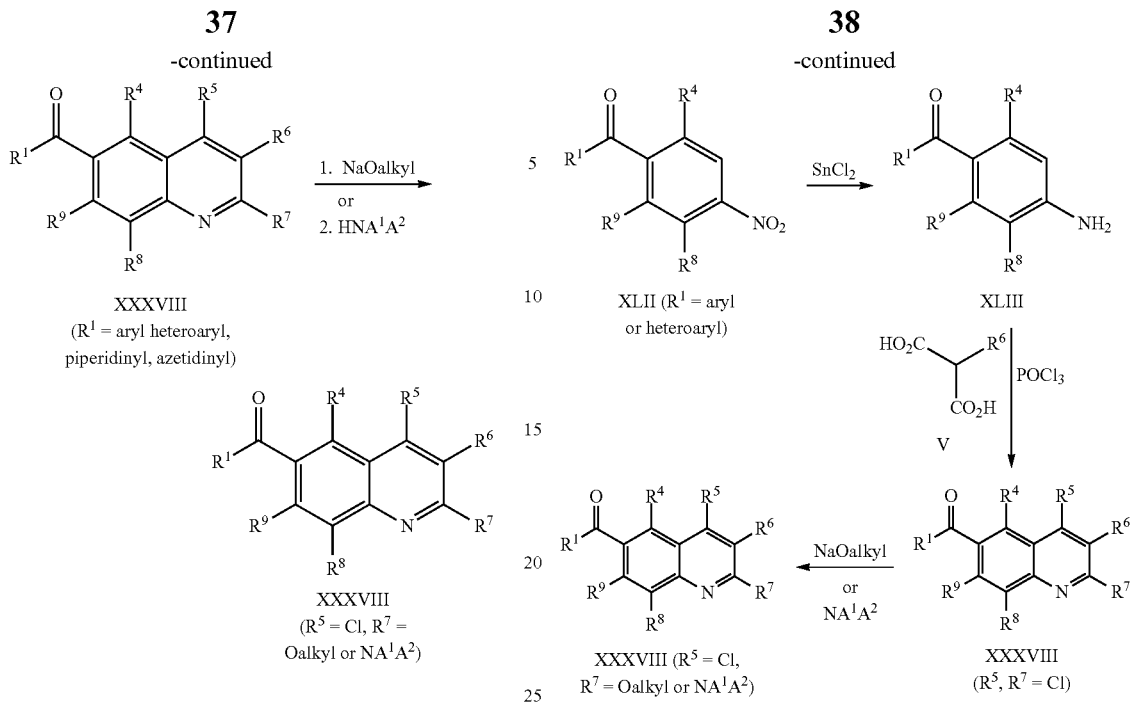

Scheme 8 describes an alternative synthesis of ketoquinolines of Formula XXXVIII. The starting 4-nitro benzoic acids can be converted to the N,O-dimethylhydroxamic acid derivatives XLI, which, following treatment with an organolithium or organomagnesium reagent (prepared in-situ as previously described), could provide 4-nitrophenylketones of Formula XLII. The nitro group can then be reduced with reagents such as tin (II) chloride under standard conditions well known in the art, to provide ketoanilines XLIII. The ketoanilines XLIII can be condensed with malonic acids V and phosphorus oxychloride as previously described (Scheme 1) to form 6-ketoquinolines XXXVIII wherein $R^5$ and $R^7$ are Cl. Conversion of the chlorines at the 2-position can be achieved as described above (Scheme 5) to provide ketoquinolines XXXVIII wherein $R^5$ is Cl and $R^7$ is Oalkyl or $NA^1A^2$.

Scheme 9 exemplifies the method used to introduce $R^2$ for the formation of tertiary alcohols of Formula I wherein $R^2$ is alkyl, substituted alkyl, cycloalkyl or alkynyl and $R^3$ is OH. As shown in path 1, Grignard reagents $R^2MgX$ (X=Br or I) of Formula XLIV, obtained through commercial sources or prepared from the corresponding bromides or halides and magnesium using standard procedures well known by those skilled in the art, could be added to ketoquinolines XXXVIII wherein $R^1$ is aryl or heteroaryl at temperatures between 0° C. and ambient temperature to provide compounds of Formula I, wherein $R^2$ is alkyl, substituted alkyl or cycloalkyl and $R^3$ is OH. Similarly, an organolithium reagent such as $R^2Li$ can be added to the ketoquinoline XXXVIII wherein $R^1$ is aryl or heteroaryl at temperatures between −78° C. and ambient temperature in a preferred solvent such as tetrahydrofuran to afford the tertiary alcohols of Formula I wherein $R^2$ is alkyl and $R^3$ is OH (path 2). The ketoquinolines XXXVIII can also be treated with protected alkynyl lithium such as TMS-lithiumacetylide at temperatures between 0° C. and ambient temperature in a solvent such as THF followed by deprotection with a base such as KOH in a polar alcohol solvent such as methanol or ethanol to provide compounds of Formula I where in $R^2$ is acetylene and $R^3$ is OH (path 3).

Scheme 8

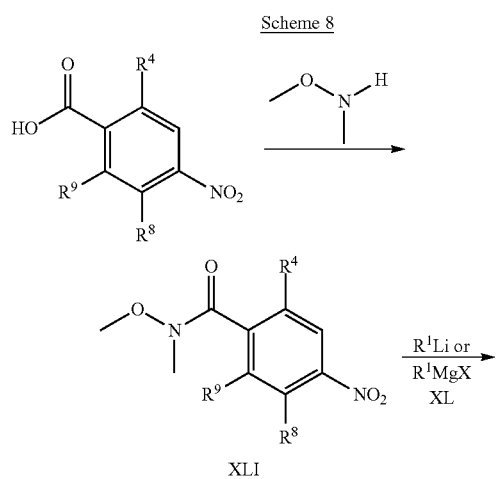

Scheme 9

PATH 1

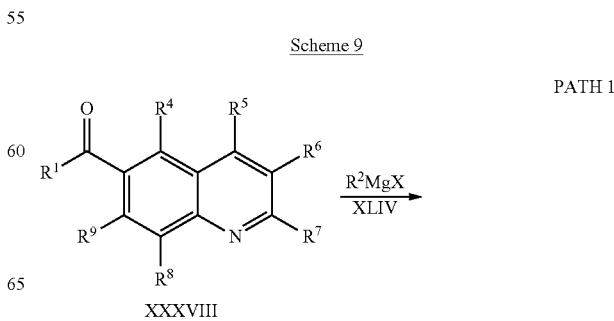

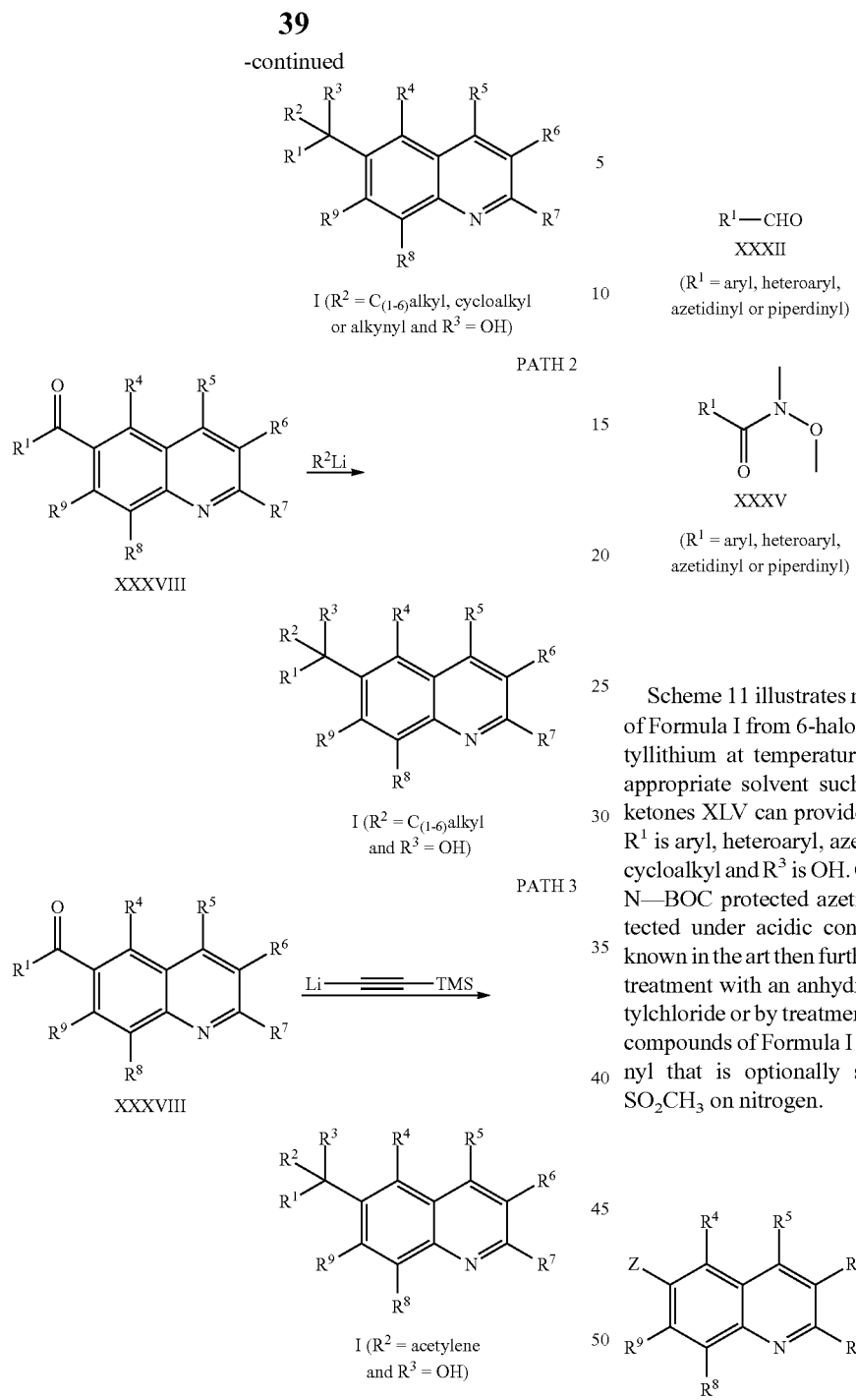
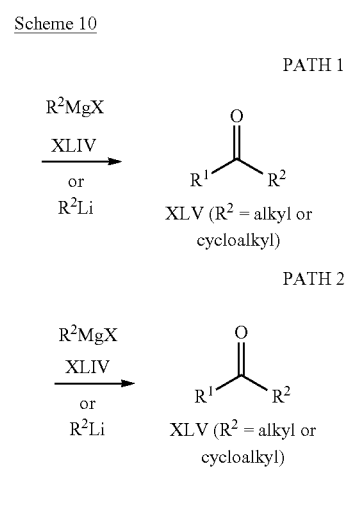

Scheme 10 provides routes that can be used to prepare ketones of Formula XLV. Ketones XLV wherein $R^1$ is aryl, heteroaryl, piperidinyl or azetidinyl and $R^2$ is alkyl or cycloalkyl as described in the detailed description of this invention, can be prepared from commercially available or prepared aldehydes XXXII (Scheme 6) by addition of lithium or Grignard reagents as shown in path 1. As shown in path 2, Weinreb amides XXXV can also be treated with lithium or Grignard (XLIV) reagents to provide the ketones of Formula XLV.

Scheme 11 illustrates methods used to prepare compounds of Formula I from 6-haloquinolines IV. Treatment with n-butyllithium at temperatures between −78 and 60° C. in an appropriate solvent such as THF followed by addition of ketones XLV can provide compounds of Formula I wherein $R^1$ is aryl, heteroaryl, azetidinyl or piperidinyl, $R^2$ is alkyl or cycloalkyl and $R^3$ is OH. Compounds of Formula I containing N—BOC protected azetidinyl or piperidinyl can be deprotected under acidic conditions using standard procedures known in the art then further functionalized on the nitrogen by treatment with an anhydride or acylating agent such as acetylchloride or by treatment with a sulfonylchloride to provide compounds of Formula I wherein $R_1$ is azetidinyl or piperidinyl that is optionally substituted with $COC_{(1-4)}$alkyl or $SO_2CH_3$ on nitrogen.

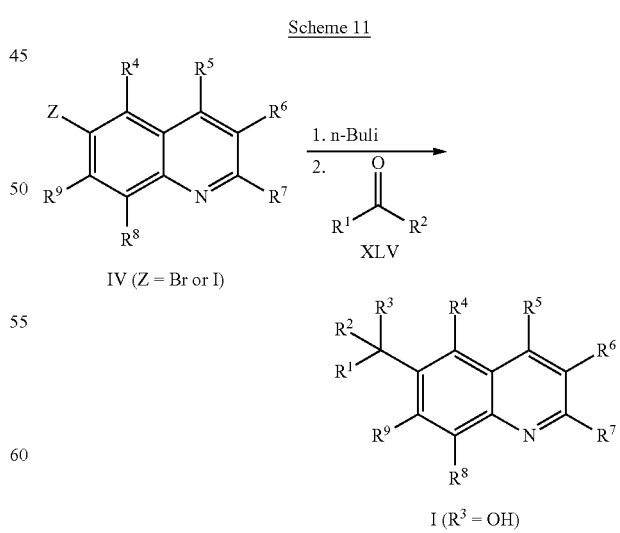

Scheme 12 illustrates methods used to synthesize compounds of Formula I wherein either the chlorine at $R^5$, $R^7$ or at both $R^5$ and $R^7$ positions are replaced with nitrogen, oxygen, sulfur or alkyl groups. In path 1 and 4, nucleophilic displacement of 2,4-dichloroquinolines of Formula I ($R^5$ and $R^7$ are Cl) with NaO(alkyl), or NaS(alkyl), such as NaOMe, NaSMe, NaOEt, or NaO$^i$Pr, in an appropriate solvent, such as MeOH, EtOH, i-PrOH or DMF at elevated temperatures or with substituted hydroxy reagents such as 2-methoxyethanol and 4 of quinolines of Formula I ($R^5$ and $R^7$ are Cl) with alkyl groups could be carried out using Zn(alkyl)$_2$ in the presence of $K_2CO_3$ and a palladium catalyst, such as PdCl$_2$(dppf), to afford 2-alkyl and 2,4-dialkylquinolines of Formula I (path 3).

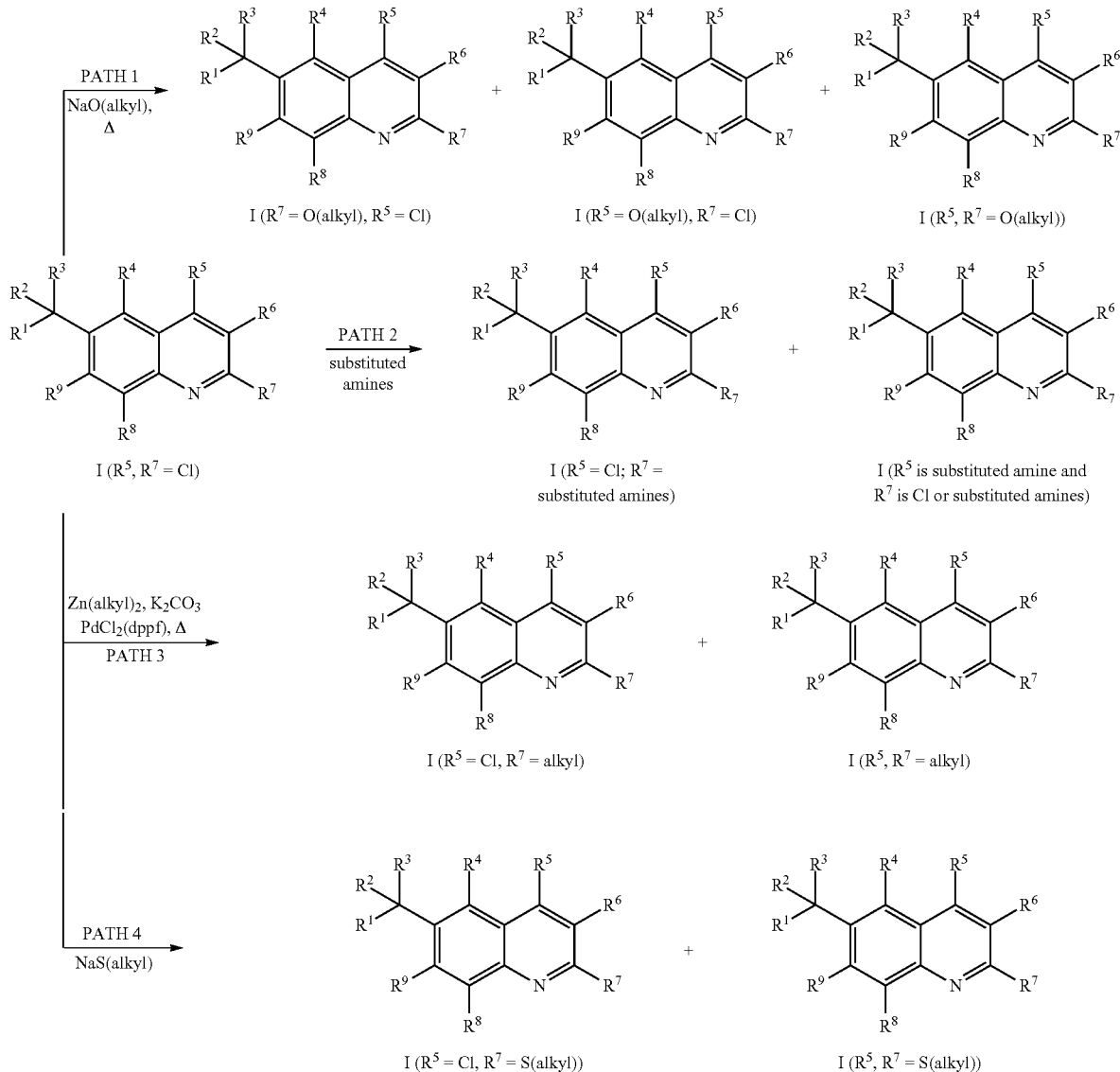

Scheme 12 in the presence of a base like sodium hydride in a non-polar solvent such as toluene (as described above) provides compounds of Formula I wherein $R^5$ is Cl and $R^7$ is O(alkyl), O(CH$_2$)$_2$OCH$_3$ or S(alkyl) and compounds of Formula I wherein $R^5$ and $R^7$ are O(alkyl) or S(alkyl). Likewise, nucleophilic displacement of 2,4-dichloroquinolines of Formula I ($R^5$ and $R^7$ are Cl) with primary or secondary alkyl amines, heterocyclic amines, or N,O-dimethylhydroxylamine in polar solvents such as MeOH, EtOH, or Et$_2$NCHO, or DMF provides quinolines of Formula I (path 2) wherein $R^5$ is NH(alkyl), N(alkyl)$_2$, N(CH$_3$)OCH$_3$, or Cl, and $R^7$ is NH(alkyl), N(alkyl)$_2$, N(CH$_3$)OCH$_3$, NA$^1$A$^2$, NHC$_{(2-3)}$alkylNA$^1$A$^2$ or N(CH$_3$)C$_{(2-4)}$alkylNA$^1$A$^2$, wherein A$^1$ and A$^2$ are as defined above. Replacement of chlorine at positions 2

Synthetic routes to compounds of Formula I, wherein $R^5$ is Cl or CN, and $R^7$ is CN or aryl, are illustrated in Scheme 13. In path 1, cyanation of the 2,4-dichloroquinolines of Formula I with Zn(CN)$_2$ in the presence of Zn, a palladium catalyst, such as Pd$_2$(dba)$_3$, and a ligand, such as dppf or X-phos, at high temperatures can provide 2-CN and 2,4-diCN quinolines of Formula I. The 2,4-dichloroquinolines of Formula I can also undergo a Suzuki reaction with ArB(OH)$_2$ or ArB(OR)$_2$ and a palladium catalyst, such as PdCl$_2$(dppf), yielding compounds of Formula I wherein $R^7$ is phenyl, substituted phenyl and five or six-membered heteroaryls such as furan, pyridine, pyridazine, pyrazine, pyrimidine, pyrrole, pyrazole or imidazole (path 2).

Scheme 13

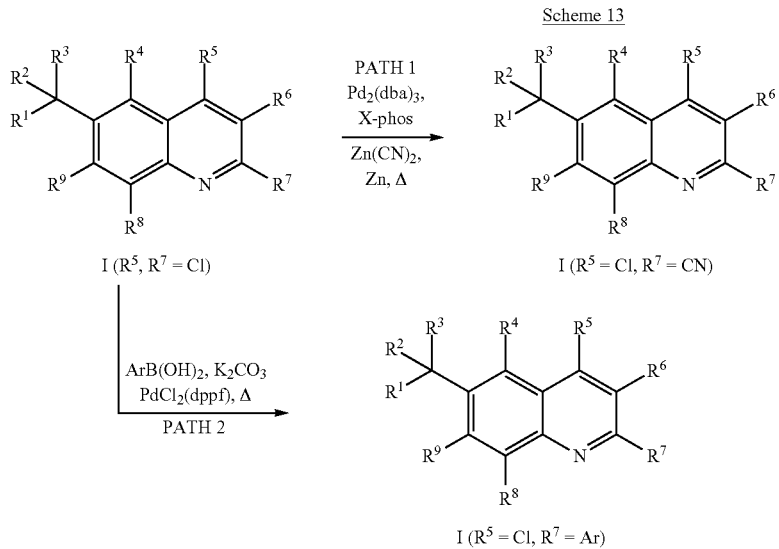
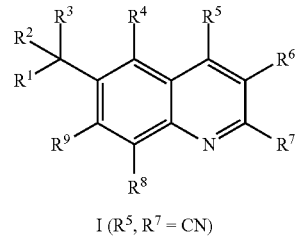

As illustrated in Scheme 14, compounds of Formula I wherein $R^5$ is a chlorine can be further substituted by treatment with alkylboronic acids or esters under Suzuki reaction conditions (path 1), with sodium alkoxides (path 2), or with zinc cyanide (path 3) using conditions previously described to provide compounds of Formula I wherein $R^5$ is alkyl, O(alkyl) or CN and $R^7$ is as described above. Palladium catalyzed hydrogenation, as shown in path 4, could also provide compounds of Formula I, wherein $R^5$ is H.

Scheme 14

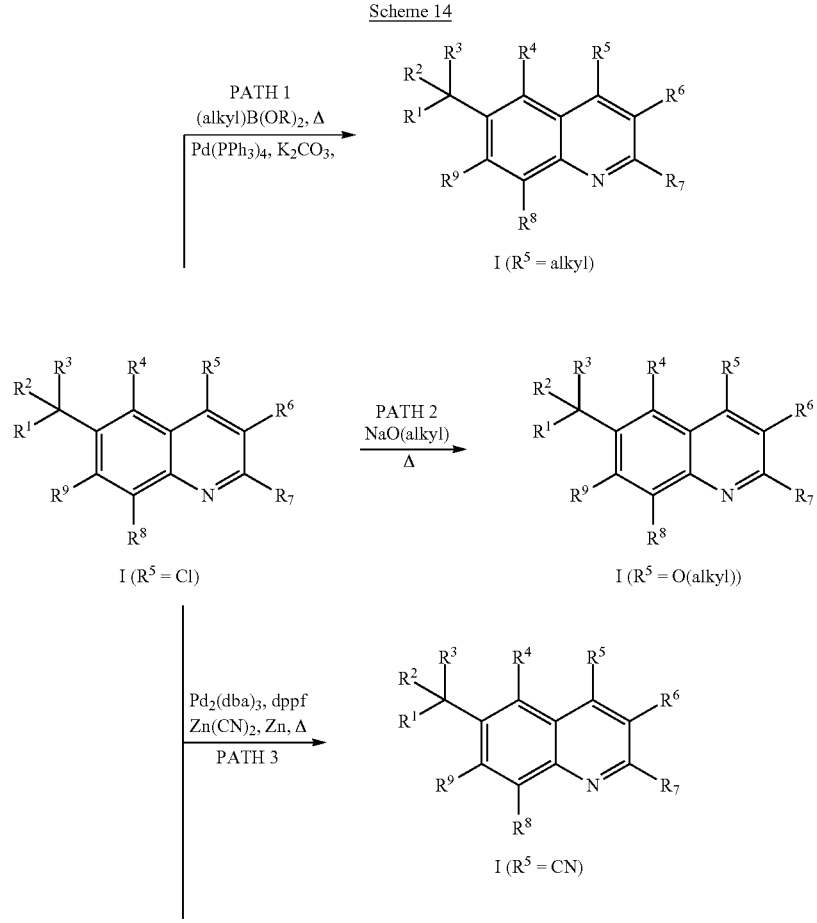

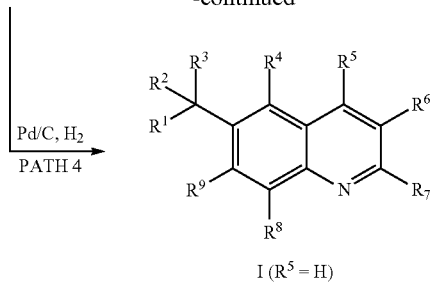

Scheme 15 describes methods known to those skilled in the art which could lead to compounds of Formula I wherein $R^3$=OMe. Tertiary alcohols of Formula I can be treated with base, such as NaH, and alkylated with MeI in DMF to provide compounds of Formula I wherein $R^3$ is OMe.

intermediate acetate wherein $R^3$ is OAc. The acetate can then be combined with a solution of ammonia in methanol and heated at temperatures between 60 and 85° C. to provide compounds of Formula I, wherein $R^3$ is $NH_2$ (path 3).

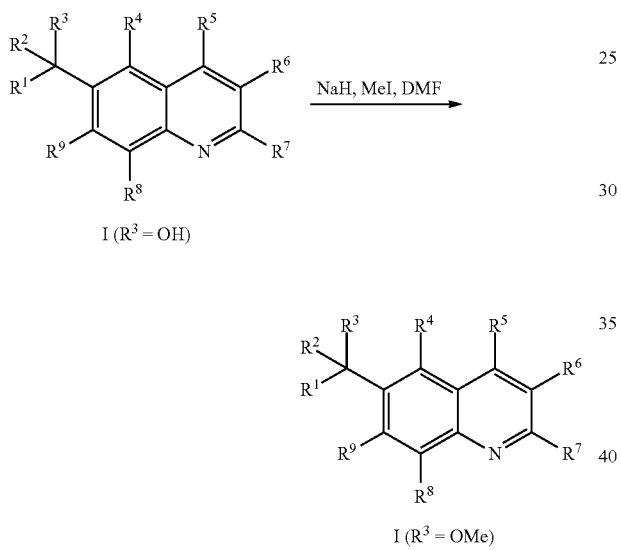

ynthetic routes that can lead to compounds of Formula I, wherein $R^a$ is $NH_2$, are illustrated in Scheme 16. Ketimine XLVI which can be prepared by Ti(OEt)$_4$ mediated condensation of ketones XLV with 2-methylpropane-2-sulfinamide in refluxing THF, can be added to lithiated 6-bromo or 6-iodoquinolines IV at −78° C. Cleavage of the tert-butanesulfinyl group with HCl in MeOH can liberate the amines I wherein $R^3$ is $NH_2$ (path 1). Path 2 illustrates an alternative route that can convert the ketoquinolines XXXVIII to ketimines XLVII. An alkyl, cycloalkyl or alkynyl magnesium bromide or chloride of Formula XLIV ($R^2$MgX) or an alkyllithium ($R^2$Li) can then be added to ketimines XLVII, followed by acidic cleavage of the tert-butanesulfinyl group using a solvent such as $CH_3OH$ to provide the tertiary amines of Formula I. Alternatively, compounds of Formula I, wherein $R^3$ is OH, can be treated with sodium hydride followed by addition of acetic anhydride or acetyl chloride and stirred at room temperature over a 24 to 72 hour period to provide the

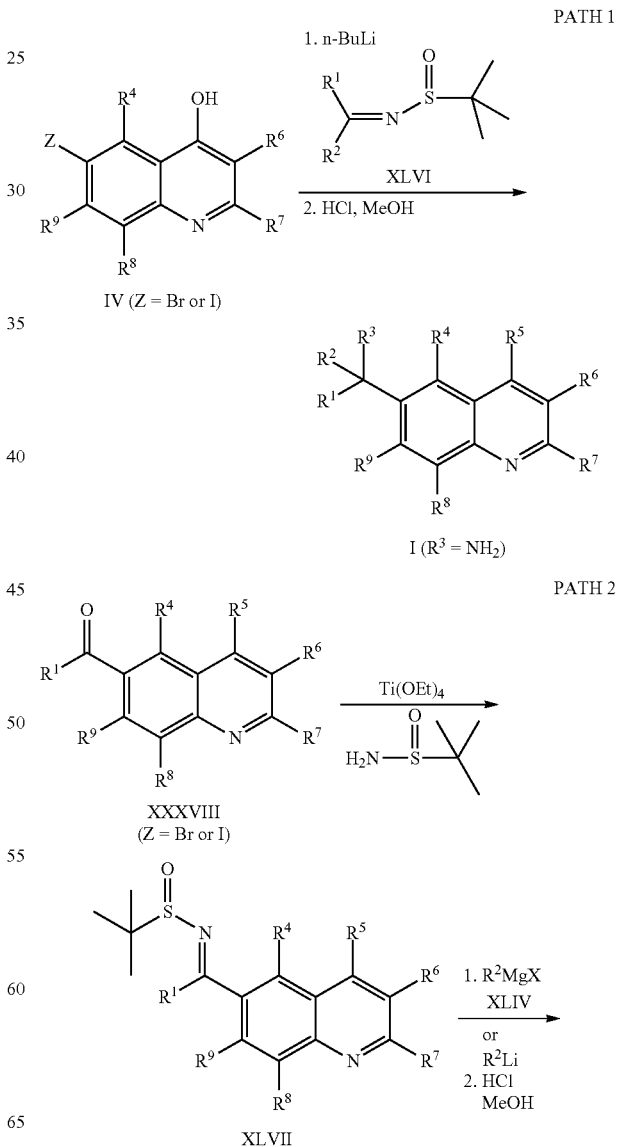

As shown in Scheme 18, compounds of the Formula I wherein $R^3$ is H can be prepared by treating compounds of Formula I wherein $R^3$ is OH with a hydride source such as triethylsilane and an acid such as trifluoracetic acid in a solvent such as dichloromethane at room temperature or with heating (WO2009091735).

Scheme 18

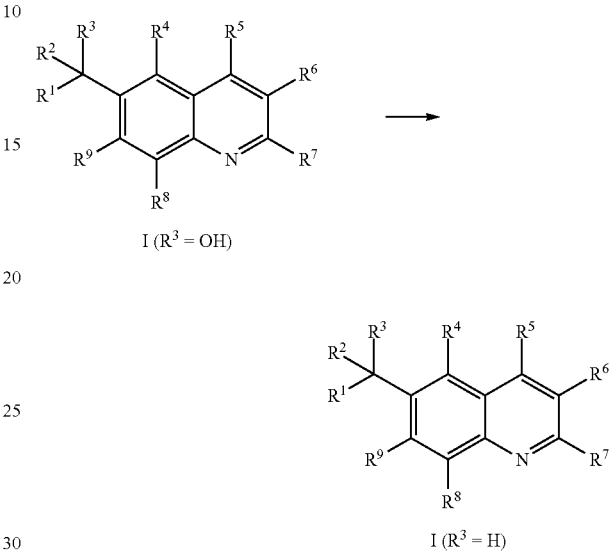

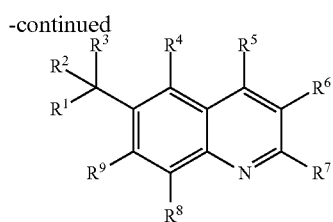

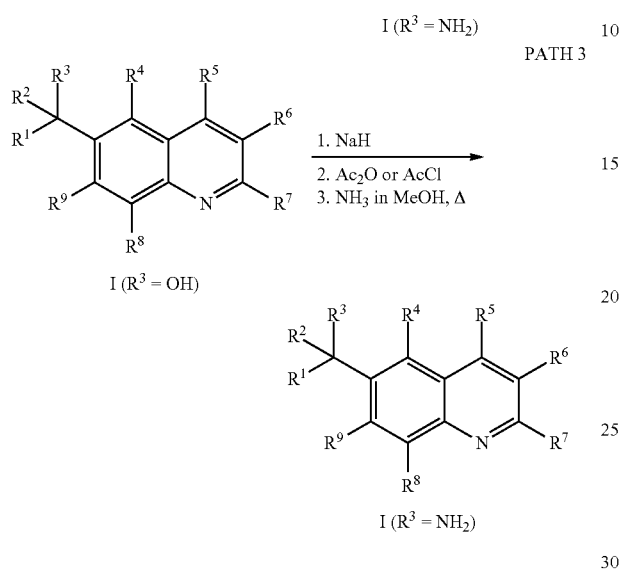

As shown in Scheme 17, the quinolines of Formula I wherein $R^7$ is CN can be hydrolyzed as described in US20080188521 by treatment with sodium carbonate and hydrogen peroxide to provide compounds of Formula I wherein $R^7$ is $CONH_2$ (path 1) or can be treated with a strong acid like HCl to convert CN to a carboxylic acid XLVIII (path 2). Once formed, the acid can be further coupled to substituted amines using appropriate coupling reagents such as EDCI or HATU in the presence of a base such as triethylamine or Hunig's base to provide compounds of Formula I wherein $R^7$ is $CONA^1A^2$.

Synthesis of compounds of Formula I, wherein $R^7$ is an aminoalkylaminomethylene or an aminoalkoxymethylene, can be prepared from 2-methylquinolines as shown in Scheme 19. Bromination of 2-methylquinolines of Formula I can be accomplished with N-bromosuccinimide in acetic acid at elevated temperatures as described in WO2010151740, to provide the methylbromide intermediates XLIX. Nucleophilic displacement of the bromide under basic conditions using procedures known in the art could afford compounds of Scheme 17

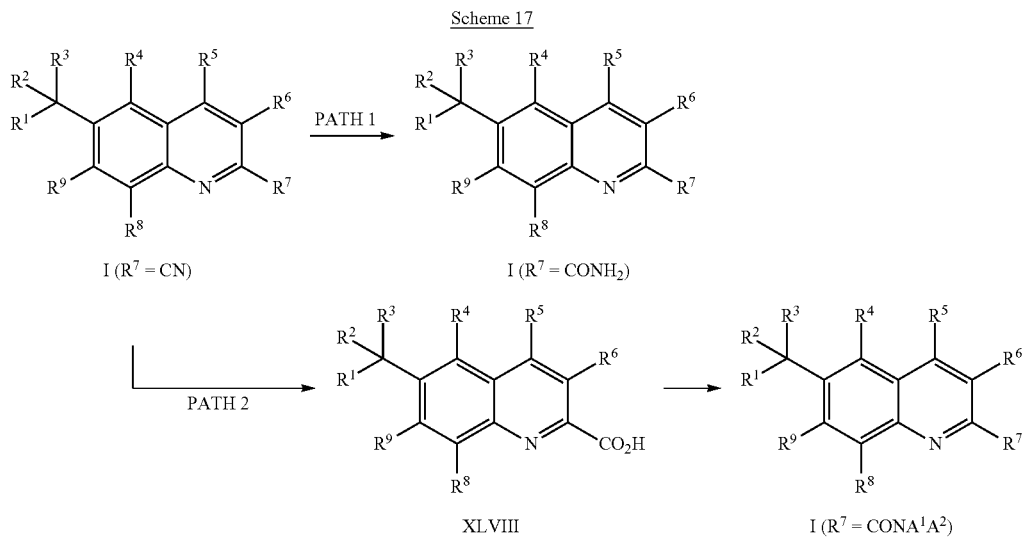

Formula I wherein $R^7$ is —$CH_2N(H)C_{(2-3)}alkylNA^1A^2$ or —$CH_2N(CH_3)C_{(2-3)}alkylNA^1A^2$ (path 1) or $CH_2OC_{(2-3)}alkylNA^1A^2$ (path 2) and $A^1$ and $A^2$ are as defined above.

Scheme 19

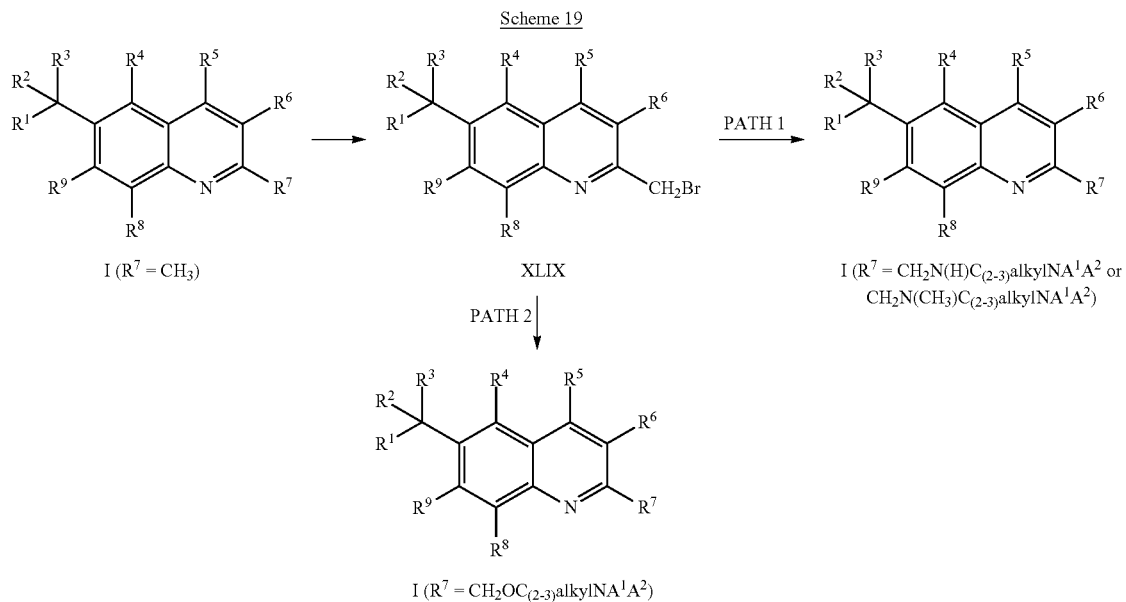

Scheme 20 outlines alternative synthetic methods to compounds of Formula I wherein $R^6$ is Ar and Ar is a phenyl ring, or heteroaryl ring as defined in the detailed description of the invention. Acylation of anilines VII with benzyloxyacetyl chloride in the presence of a base such as triethylamine in a solvent such as dichloromethane affords amides L. Amides L can undergo an intramolecular cyclization reaction with a base such as potassium bis(trimethylsilyl)amide in a solvent such as tetrahydrofuran to provide 6-halo-4-hydroxyquinolin-2(1H)-ones VIII, wherein $R^6$ is OBn. Conversion to the 2,4-dichloroquinolines IV can be accomplished in phosphorus oxychloride as previously described. The coupling of 6-haloquinolines IV and aldehydes of Formula XXXII followed by displacement of the 2 or 4-chloro using procedures previously described provides quinolines of Formula LI wherein $R^1$, $R^2$, $R^5$ and $R^7$ are as defined above. Palladium-catalyzed hydrogenation of compounds of Formula LI that are substituted with a benzyloxy at C-3 can provide intermediate quinolin-3-ols LII. The quinoline-3-ols LII can be converted into the corresponding triflates LIII with trifluoromethanesulfonic acid in the presence of a base, such as pyridine, in a solvent such as dichloromethane. The triflates LIII can be converted into compounds of Formula I, wherein $R^6$ is aryl or heteroaryl as defined above, by a palladium-catalyzed cross coupling with organoboron reagents of the formula $R^6B(OR)_2$ in the presence of a base, such as potassium carbonate, in a solvent mixture such as 1,4-dioxane/water.

Scheme 20

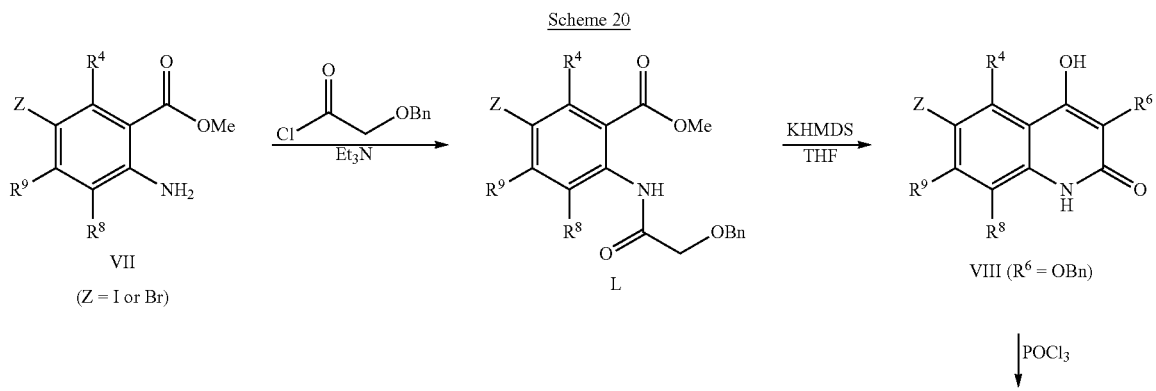

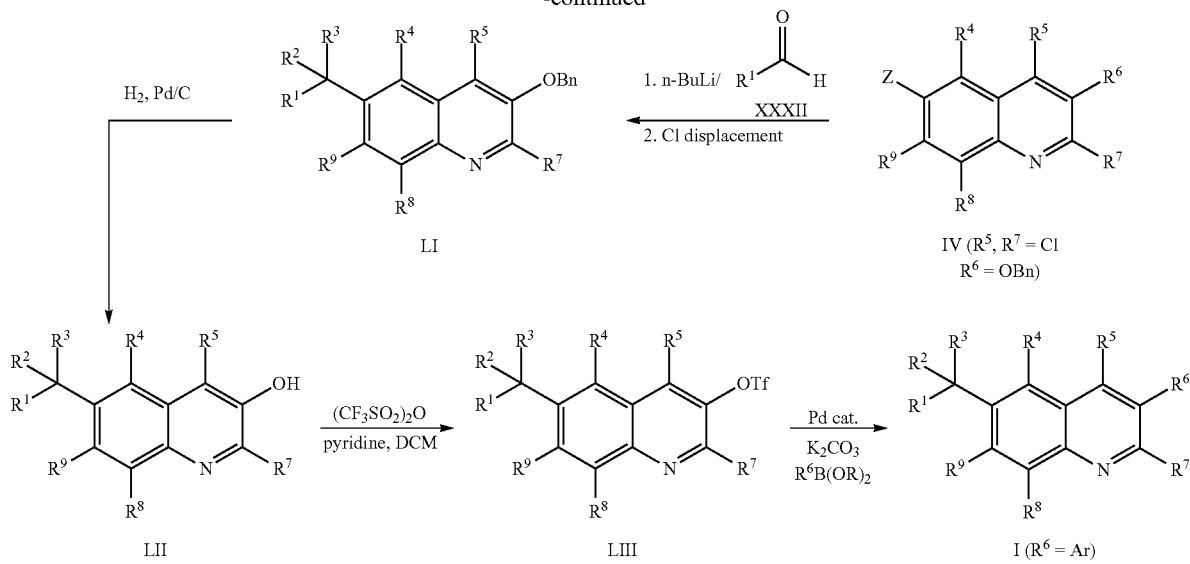

Compounds of Formula I wherein $R^1$, $R^2$, or $R^6$ are or contain a pyridyl can be treated with m-chloroperbenzoic acid in a chlorinated solvent at ambient temperature to 40° C. to form the pyridyl-N-oxides of Formula I.

EXAMPLES

Compounds of the present invention can be prepared by methods known to those who are skilled in the art. The following examples are only meant to represent examples of the invention and are in no way meant to be a limit of the invention.

Intermediate 1: Step a

Methyl 5-bromo-2-(2-phenylacetamido)benzoate

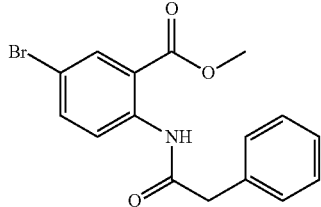 [SMILES: COC(=O)c1cc(Br)ccc1NC(=O)Cc1ccccc1]

To a mixture of methyl 2-amino-5-bromobenzoate (9.00 g, 39.1 mmol) and $Et_3N$ (7.6 mL, 54.8 mmol) in $CH_2Cl_2$ (90 mL) was added 2-phenylacetyl chloride (7.26 g, 46.9 mmol) at 4° C. dropwise. After completion of the addition, the cooling bath was removed and the mixture was stirred for 27 hours. TLC showed some of the starting material methyl 2-amino-5-bromobenzoate still remained. More 2-phenylacetyl chloride (1.88 g, 12.2 mmol) and $Et_3N$ (2.2 mL, 15.9 mmol) were added, and the mixture was stirred overnight. $K_2CO_3$ (aqueous) was added, the organic layer was separated, and the aqueous layer was extracted with $CH_2Cl_2$. The combined organic layers were washed with water, dried ($Na_2SO_4$), filtered, and concentrated in vacuo. $CH_3CN$ (100 mL) was added, and the precipitated solid was filtered, washed with $Et_2O$, and dried to provide the title compound. The filtrate was concentrated in vacuo, and the solid was filtered, washed with $Et_2O$, and dried to provide additional title compound.

Intermediate 1: Step b

6-Bromo-4-hydroxy-3-phenylquinolin-2(1H)-one

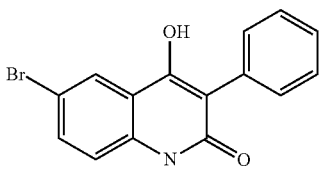 [SMILES: O=c1[nH]c2ccc(Br)cc2c(O)c1-c1ccccc1]

To a solution of methyl 5-bromo-2-(2-phenylacetamido) benzoate (7.71 g, 22.1 mmol, Intermediate 1: step a) in THF (50 mL) at −78° C. was added 1.0 M lithium bis(trimethylsilyl)amide in hexane (48.7 mL, 48.7 mmol) slowly, and the color changed from clear to clear red. The mixture was stirred at −78° C. to room temperature for 4 hours, during which time the color changed to cloudy yellow. The reaction was quenched with water, and acidified with 37% HCl until pH~5. The precipitated solid was filtered, washed with water and $Et_2O$, and air dried to provide the title compound. More solid was precipitated from the filtrate after standing overnight. The solid was collected by filtering, washing with water and $Et_2O$, and air drying to afford additional title compound.

Intermediate 1: Step c

6-Bromo-2,4-dichloro-3-phenylquinoline

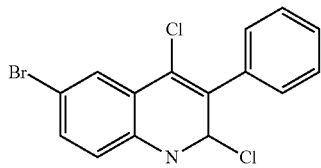 [SMILES: ClC1=C(c2ccccc2)C(Cl)Nc2ccc(Br)cc21]

A solution of 6-bromo-4-hydroxy-3-phenylquinolin-2 (1H)-one (8.50 g, 26.9 mmol, Intermediate): step b) in phosphoryl trichloride (51 mL, 547 mmol) was heated at 107° C. for 3.5 hours, and then cooled to room temperature. After evaporation of the POCl$_3$ in vacuo, concentrated NH$_4$OH (aqueous) was added dropwise at 4° C. until pH 9. The precipitated solid was filtered, washed with water, and dried at 50° C. under vacuum overnight to provide the title compound.

Intermediate 2: Step a

(2,4-Dichloro-3-phenylquinolin-6-yl)(1-methyl-1H-imidazol-5-yl)methanol

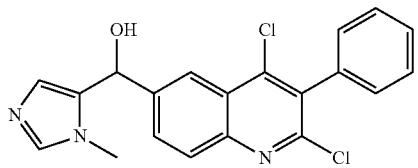 [SMILES: Cn1cncc1C(O)c1ccc2nc(Cl)c(-c3ccccc3)c(Cl)c2c1]

To a cloudy mixture of 6-bromo-2,4-dichloro-3-phenylquinoline (290.5 mg, 0.823 mmol, Intermediate 1: step c) and 1-methyl-1H-imidazole-5-carbaldehyde (90.6 mg, 0.823 mmol) in THF (8 mL) under nitrogen at −78° C. was added n-BuLi (1.6 M in hexane, 0.643 mL, 1.03 mmol) dropwise. The resulting solution was stirred at −78° C. for 3 hours, then was warmed to 0° C. for 15 minutes before addition of saturated aqueous NH$_4$Cl to quench. The mixture was diluted with water and was extracted three times with EtOAc. The organic phase was dried (Na$_2$SO$_4$), filtered, and concentrated. The residue was purified by flash column chromatography (silica gel, 0-6% MeOH-DCM) to afford the title compound as a white powder.

Intermediate 2: Step b

(2,4-Dichloro-3-phenylquinolin-6-yl)(1-methyl-1H-imidazol-5-yl)methanone

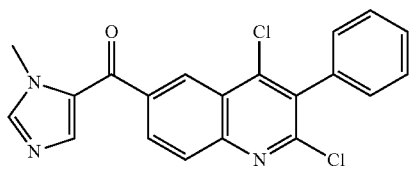 [SMILES: Cn1cncc1C(=O)c1ccc2nc(Cl)c(-c3ccccc3)c(Cl)c2c1]

Manganese (IV) oxide (1.17 g, 13.4 mmol) was added to a solution of (2,4-dichloro-3-phenylquinolin-6-yl)(1-methyl-1H-imidazol-5-yl)methanol (1.03 g, 2.68 mmol, Intermediate 2: step a) in 1,4-dioxane (15 mL). The resulting black suspension was fitted with a reflux condenser and was refluxed for 3 hours. The reaction mixture was cooled to room temperature, diluted with DCM, and was filtered through Celite®, washing with DCM. The filtrate was concentrated and the residue was purified by flash column chromatography (silica gel, 1-3% MeOH-DCM, first column; 10-25% acetone-EtOAc, second column) to afford the title compound as a white solid.

Intermediate 3: Step a

(2,4-Dichloro-3-phenylquinolin-6-yl)(3-methylisoxazol-5-yl)methanol

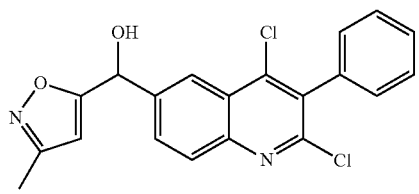 [SMILES: Cc1cc(C(O)c2ccc3nc(Cl)c(-c4ccccc4)c(Cl)c3c2)on1]

To a mixture of 6-bromo-2,4-dichloro-3-phenylquinoline (363 mg, 1.03 mmol, Intermediate 1: step c) and 3-methylisoxazole-5-carbaldehyde (149 mg, 1.34 mmol) in THF (5 mL) at −78° C. was added n-BuLi (1.6 M in hexane, 0.707 mL, 1.13 mmol) dropwise. The mixture was stirred at −78° C. for 30 minutes, then moved to an ice bath and stirred for 30 minutes. The reaction was quenched by addition of saturated aqueous NH$_4$Cl and then diluted with water. The mixture was extracted three times with EtOAc. The organic phase was dried (Na$_2$SO$_4$), filtered, and concentrated to afford the crude title compound which was used without further purification in the next reaction.

Intermediate 3: Step b

(2,4-Dichloro-3-phenylquinolin-6-yl)(3-methylisoxazol-5-yl)methanone

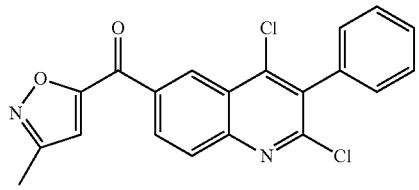 [SMILES: Cc1cc(C(=O)c2ccc3nc(Cl)c(-c4ccccc4)c(Cl)c3c2)on1]

1,4-dioxane (7.5 mL) and manganese (IV) dioxide (447 mg, 5.14 mmol) were added to crude (2,4-dichloro-3-phenylquinolin-6-yl)(3-methylisoxazol-5-yl)methanol (Intermediate 3: step a, 1.03 mmol assuming theoretical yield in prior step). The resulting black suspension was heated in a 100° C. oil bath in a sealed tube for 3 hours then cooled to room temperature. The mixture was then diluted with DCM, and filtered through Celite®. The filtrate was concentrated and the residue was purified by flash column chromatography

Intermediate 4: Step a 1-(2,4-dimethylthiazol-5-yl)-2-methylpropan-1-ol

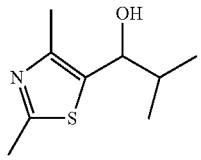

A solution of 2,4-dimethylthiazole-5-carbaldehyde (1.07 g, 7.58 mmol) in THF (12 mL) was cooled to 0° C. Isopropyl magnesium chloride LiCl complex (1.3 M in THF, 6 mL, 8.8 mmol) was then added dropwise. After 30 minutes, the reaction mixture was quenched with aqueous NH$_4$Cl solution and the aqueous portion was extracted with EtOAc (3×50 mL). The combined organics were washed with brine, dried over MgSO$_4$, filtered and concentrated to afford an orange oil. Chromatography on silica gel (5% acetone-DCM increasing to 30% acetone) provided the title compound as a light amber oil.

Intermediate 4: Step b 1-(2,4-dimethylthiazol-5-yl)-2-methylpropan-1-one

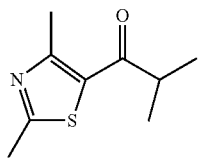

A flask containing Dess-Martin reagent (2.5 g, 5.89 mmol) in DCM (50 mL) was cooled to 0° C. and then a solution of 1-(2,4-dimethylthiazol-5-yl)-2-methylpropan-1-ol (830 mg, 4.48 mmol, Intermediate 4: step a) in DCM (10 mL) was added. After 5 minutes, the ice bath was removed and the reaction mixture was allowed to stir at room temperature for 45 minutes. The mixture was quenched with saturated aqueous NaHCO$_3$ and 1 N aqueous NaOH (2 mL) and the aqueous portion (pH~9) was extracted with DCM (3×75 mL). The combined organics were washed with brine, dried over MgSO$_4$, filtered and concentrated. Chromatography on silica gel (10% EtOAc-DCM) afforded the title compound as a colorless oil.

(silica gel, 3-15% EtOAc-heptane) to afford slightly impure title compound which was used without further purification.

Intermediate 5: Step a 2,2-Dimethyl-5-(4-(trifluoromethyl)benzyl)-1,3-dioxane-4,6-dione

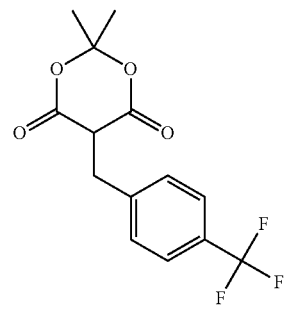 [SMILES: CC1(C)OC(=O)C(Cc2ccc(C(F)(F)F)cc2)C(=O)O1]

Similar procedures to those referenced in Tett. Lett. (2006), 651, D. Ramachary; Eur. J. Org. Chem. (2008), 975, D. Ramachary were employed. To a 5 L 3-necked flask fitted with an overhead mechanical stirrer was charged with 4-(trifluoromethyl)benzaldehyde (43.5 g, 250 mmol) followed by the addition of anhydrous EtOH (3,000 mL), Meldrum's acid (37.5 g, 260 mmol), diethyl 2,6-dimethyl-1,4-dihydropyridine-3,5-dicarboxylate (67.5 g, 266 mmol) and L-proline (6.0 g, 51 mmol) at room temperature. The yellowish reaction mixture was stirred at room temperature under N$_2$. An aliquot was removed after 4 hours and rinsed with EtOH and then Et$_2$O, and air dried. The $^1$H NMR of this aliquot showed the reaction to be complete. The full reaction was stopped and the white precipitate from the reaction was collected by filtration and rinsed with EtOH and then Et$_2$O and dried under vacuum to afford the title compound in the first crop as a fine white solid. The yellowish mother liquors were concentrated and allowed to crystallize overnight from EtOH and the solid material was collected as before to provide the title compound.

Intermediate 5: Step b 2-(4-(Trifluoromethyl)benzyl)malonic acid

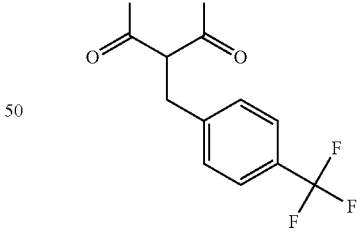

To a 2 L flask containing 2,2-dimethyl-5-(4-(trifluoromethyl)benzyl)-1,3-dioxane-4,6-dione (65 g, 215 mmol, Intermediate 5: step a) was added a TFA/water solution (v/v, 560 mL/280 mL) at room temperature and the white suspension was heated between 70° C. and 78° C. in a large oil bath. The suspension did not dissolve until a temperature of 72° C. was reached. After approximately 40 minutes, the suspension became a clear homogeneous solution. After 3 hours, HPLC indicated that the reaction was complete. The mixture was concentrated on the rotary evaporator and azeotroped with toluene (4×100 mL) to provide the title compound as a white solid which was used without further purification.

Intermediate 5: Step c

6-Bromo-2,4-dichloro-3-(4-(trifluoromethyl)benzyl)quinoline

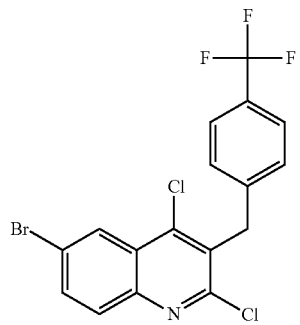 [SMILES: FC(F)(F)c1ccc(Cc2c(Cl)nc3ccc(Br)cc3c2Cl)cc1]

A 500 mL 3-necked flask fitted with a reflux condenser and Drierite drying tube, was charged with $POCl_3$ (190 mL). Then, 2-(4-(trifluoromethyl)benzyl)malonic acid (28.5 g, 109 mmol, Intermediate 5: step b) was added followed by 4-bromoaniline (19 g, 110 mmol) at room temperature. The heterogeneous mixture was heated in an aluminum mantle to 100° C. which resulted in a light amber homogenous solution after approximately 10 minutes. The reaction was stirred at 110° C. for 6.5 hours, after which removal of an aliquot and TLC (20% hexane-DCM) showed the reaction to be complete. The contents were transferred to a 1 L single-necked round bottom flask and the $POCl_3$ was removed by evaporation. The resulting dark brown material was then poured onto ice chips (~500 g) in a 2 L Erlenmeyer flask pre-cooled to 0° C. DCM (~500 mL) was added and the solution was stirred at 0° C. as a solution of 6 M aqueous KOH (~500 mL) was added carefully. 5 N aqueous $NH_4OH$ (~100 mL) was also added to bring the pH to ~8-9. The neutralization process was kept at 0° C. throughout. More DCM was added and the organic phase was separated. The aqueous portion was washed with DCM (3×250 mL) and the combined organics were washed with brine, dried over $Na_2SO_4$, filtered and concentrated to provide a brown solid. The crude solid was triturated with $CH_3CN$ which provided the title compound as a white fluffy solid after filtration.

Intermediate 5: Step d

6-Bromo-4-chloro-2-methoxy-3-(4-(trifluoromethyl)benzyl)quinoline

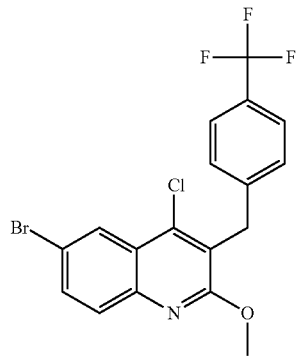 [SMILES: COc1nc2ccc(Br)cc2c(Cl)c1Cc1ccc(C(F)(F)F)cc1]

To a 1 L flask containing 6-bromo-2,4-dichloro-3-(4-(trifluoromethyl)benzyl)quinoline (32.5 g, 74.7 mmol, Intermediate 5: step c) was added toluene (550 mL) followed by solid sodium methoxide (40 g, 740 mmol, 97% purity) at room temperature. The suspension was stirred at reflux (~118° C.) in an aluminum mantle. TLC (50% hexane-DCM) and HPLC after 5.5 hours showed the reaction to be complete. The reaction mixture was filtered through Celite® while still warm (~80° C.) and rinsed with warm toluene (~70° C., 500 mL). The colorless filtrate was concentrated which then solidified to afford the title compound as an off white solid.

Intermediate 6: Step a

5-(4-Methylsulfonylbenzyl)-2,2-dimethyl-1,3-dioxane-4,6-dione

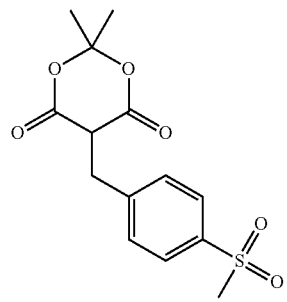 [SMILES: CC1(C)OC(=O)C(Cc2ccc(S(C)(=O)=O)cc2)C(=O)O1]

Proline (0.126 g, 1.086 mmol) was added to a solution of 4-(methylsulfonyl)benzaldehyde (1.00 g, 5.43 mmol) and Meldrum's acid (1.38 g, 5.43 mmol) in EtOH (10 mL). The mixture was stirred at room temperature for 1 hour and then diethyl 1,4-dihydro-2,6-dimethyl-3,5-pyridinedicarboxylate (1.38 g, 5.43 mmol) was added. Stirring was continued for 3 hours and then EtOH was removed under reduced pressure. The residue was diluted with i-PrOH and filtered to provide the title compound as a white solid.

Intermediate 6: Step b

2-(4-Methylsulfonylbenzyl)malonic acid

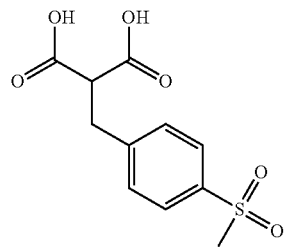 [SMILES: CS(=O)(=O)c1ccc(CC(C(=O)O)C(=O)O)cc1]

A solution of 5-(4-methylsulfonylbenzyl)-2,2-dimethyl-1,3-dioxane-4,6-dione (1.50 g, 4.80 mmol, Intermediate 6: step a) and 3 M aqueous NaOH (16 mL) was heated in the microwave at 75 W for 20 minutes at 120° C. The aqueous mixture was extracted with EtOAc (1×). The aqueous layer was acidified to pH 1 with concentrated aqueous HCl and extracted with EtOAc (2 x). The combined EtOAc extracts was washed with $H_2O$, brine, dried over $Na_2SO_4$, filtered and evaporated to dryness to afford the title compound as a white solid.

Intermediate 7: Step a

N-Methoxy-N-methyl-4-nitrobenzamide

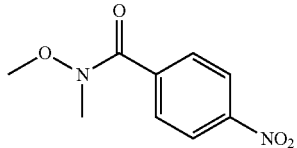

Triethylamine (4.89 mL, 35.18 mmol) was added slowly to a mixture of 4-nitrobenzoic acid (3.0 g, 17.59 mmol), N,O-dimethylhydroxylamine hydrochloride (1.92 g, 19.35 mmol), and EDCI (4.05 g, 21.1 mmol) in $CH_2Cl_2$ (30 mL). The mixture was stirred at room temperature overnight then quenched with saturated aqueous $NaHCO_3$. Water (50 mL) was added followed by additional $CH_2Cl_2$. The mixture as stirred for 10 minutes and layers were separated. The $CH_2Cl_2$ layer was dried over $Na_2SO_4$, then filtered. The solvent was removed under reduced pressure and the residual oil chromatographed ($CH_2Cl_2$/EtOAc) to provide the title compound as a white solid.

Intermediate 7: Step b (1-Methyl-1H-imidazol-5-yl)(4-nitrophenyl)methanone

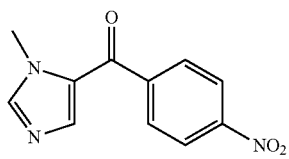 [SMILES: Cn1cncc1C(=O)c1ccc([N+](=O)[O-])cc1]

To a solution of 5-bromo-1-methyl-1H-imidazole (3.22 g, 19.98 mmol) in DCM (15 mL) was added ethyl magnesium bromide (6.66 mL, 19.98 mmol, 3.0 M in diethyl ether) dropwise over a 10 minute period. The resulting orange-red solution was stirred at room temperature for 15 minutes, cooled in an ice bath to 0° C. and N-methoxy-N-methyl-4-nitrobenzamide (3.5 g, 16.65 mmol, Intermediate 7: step a) dissolved in DCM (10 mL) was added dropwise. The ice bath was removed and the solid suspension stirred at room temperature for 48 hours. Water was added followed by 6 M aqueous HCl to a neutral pH (pH=6-7). The aqueous mixture was extracted with DCM, dried over $Na_2SO_4$, filtered and concentrated. $Et_2O$ was added and the mixture sonicated. The precipitate was collected by filtration and dried to provide the title compound as a tan solid.

Intermediate 7: Step c (4-Aminophenyl)(1-methyl-1H-imidazol-5-yl)methanone

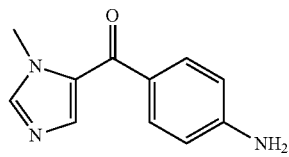

A mixture of (1-methyl-1H-imidazol-5-yl)(4-nitrophenyl)methanone (1.30 g, 5.62 mmol, Intermediate 7: step b) and tin (II) chloride dihydrate (6.54 g, 28.1 mmol) in EtOH (35 mL) was stirred at reflux for 1 hour, cooled to room temperature and evaporated in vacuo to remove most of the EtOH. The residue was poured into a 3 M aqueous NaOH/ice solution rinsing with EtOAc. The mixture was stirred at room temperature for 15 minutes then the layers were separated. The aqueous layer was extracted with EtOAc. The combined EtOAc extracts were washed with brine, dried ($Na_2SO_4$), filtered and evaporated in vacuo to provide the title compound as a yellow solid.

Intermediate 7: Step d (2,4-Dichloro-3-(4-(methylsulfonyl)benzyl)quinolin-6-yl)(1-methyl-1H-imidazol-5-yl)methanone

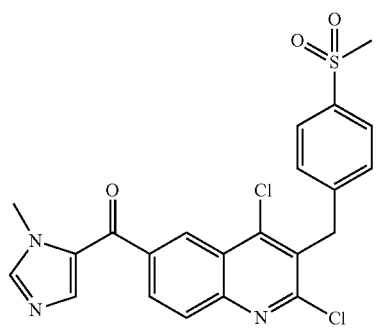 [SMILES: Cn1cncc1C(=O)c1ccc2nc(Cl)c(Cc3ccc(S(C)(=O)=O)cc3)c(Cl)c2c1]

A heterogeneous mixture of (4-aminophenyl)(1-methyl-1H-imidazol-5-yl)methanone (0.27 g, 1.34 mmol, Intermediate 7: step c), 2-(4-methylsulfonylbenzyl)malonic acid (0.36 g, 1.34 mmol, Intermediate 6: step b) and $POCl_3$ was heated in an oil bath at 105° C. for 4 hours, then cooled to room temperature and concentrated to remove excess $POCl_3$. Ice water was added and the mixture treated with aqueous $NH_4OH$ (28-30% solution) to a basic pH (8-9). The mixture was extracted with DCM (2×). The organic layers were dried over $Na_2SO_4$, filtered, evaporated in vacuo and chromatographed (0-5% MeOH in DCM) to provide the title compound as a yellow solid.

Intermediate 7: Step e (4-Chloro-2-methoxy-3-(4-(methylsulfonyl)benzyl)quinolin-6-yl)(1-methyl-1H-imidazol-5-yl)methanone

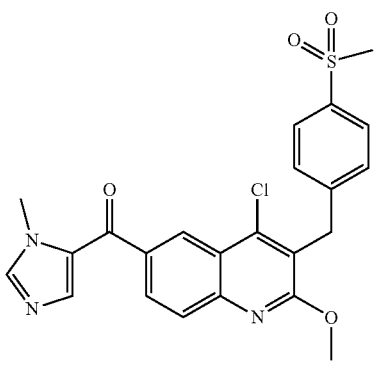 [SMILES: COc1nc2ccc(C(=O)c3cncn3C)cc2c(Cl)c1Cc1ccc(S(C)(=O)=O)cc1]

A mixture of (2,4-dichloro-3-(4-(methylsulfonyl)benzyl)quinolin-6-yl)(1-methyl-1H-imidazol-5-yl)methanone (0.2 g, 0.42 mmol, Intermediate 7: step d) and dry sodium methoxide (0.11 g, 2.11 mmol) in toluene (10 mL) was heated in a sealed tube at 105° C. for 6 hours. The mixture was then cooled to room temperature, diluted with DCM and stirred for 30 minutes at room temperature. The resulting suspension was filtered through Celite®, rinsing several times with DCM. The solvents were removed under reduced pressure and the residue chromatographed (heptane/DCM gradient) to provide the title compound as a white solid.

Intermediate 8: Step a (4-Chloro-2-methoxy-3-(4-(trifluoromethyl)benzyl)quinolin-6-yl)(1,2-dimethyl-1H-imidazol-5-yl)methanol

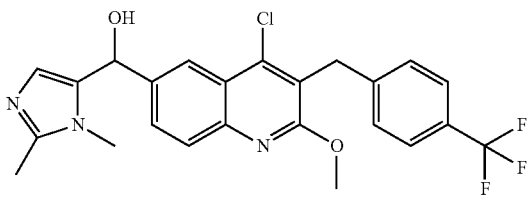 [SMILES: COc1nc2ccc(C(O)c3cnc(C)n3C)cc2c(Cl)c1Cc1ccc(C(F)(F)F)cc1]

To a flask containing 6-bromo-4-chloro-2-methoxy-3-(4-(trifluoromethyl)benzyl)quinoline (2.0 g, 4.64 mmol, Intermediate 5: step d) was added THF (25 mL). The solution was cooled to −70° C. and then n-BuLi (2.5 M in hexanes, 1.8 mL, 4.5 mmol) was added dropwise. After 2 minutes, 1,2-dimethyl-1H-imidazole-5-carbaldehyde (720 mg, 5.8 mmol in 5 mL THF) was introduced. The reaction mixture was allowed to warm to 0° C. over 60 minutes at which time it was quenched with aqueous $NH_4Cl$ solution. The aqueous portion was extracted with EtOAc:THF (10:1, 5×50 mL). The combined organics were washed with brine, dried over $MgSO_4$, filtered and concentrated. The solid was triturated with EtOAc:$Et_2O$ (1:1), collected by filtration, rinsed with additional $Et_2O$ and dried to afford the title compound. The mother liquors were concentrated and chromatographed on silica gel (3% MeOH-DCM increasing to 10% MeOH) to provide additional title compound.

Intermediate 8: Step b (4-Chloro-2-methoxy-3-(4-(trifluoromethyl)benzyl)quinolin-6-yl)(1,2-dimethyl-1H-imidazol-5-yl)methanone

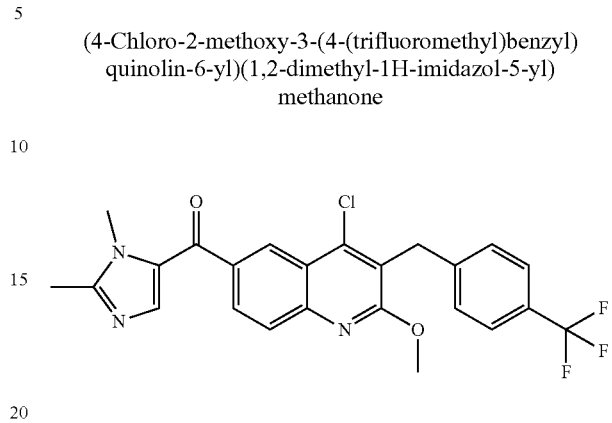

To a flask containing (4-chloro-2-methoxy-3-(4-(trifluoromethyl)benzyl)quinolin-6-yl)(1,2-dimethyl-1H-imidazol-5-yl)methanol (1.68 g, 3.53 mmol, Intermediate 8: step a) was added 1,4-dioxane (75 mL) and THF (10 mL) which produced a suspension at room temperature. Warming to 45° C. formed a homogeneous solution. Then, manganese dioxide (1.5 g, 17.25 mmol) was introduced and the mixture was heated to 80° C. After 60 minutes, the contents were filtered through a Celite® pad, rinsing with THF, and then the solution was concentrated. Trituration with $Et_2O$ provided the title compound as a white powder.

Intermediate 9: Step a (4-Chloro-2-methoxy-3-(4-(trifluoromethyl)benzyl)quinolin-6-yl)(1-methyl-1H-1,2,3-triazol-5-yl)methanol

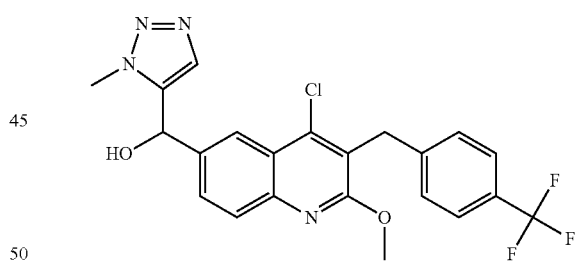

To a flask containing 6-bromo-4-chloro-2-methoxy-3-(4-(trifluoromethyl)benzyl)quinoline (1.45 g, 3.37 mmol, Intermediate 5: step d) was added THF (25 mL) and the solution was cooled to −75° C. n-BuLi (2.5 M in hexanes, 1.3 mL, 3.25 mmol) was then added dropwise. After 2 minutes, 1-methyl-1H-1,2,3-triazole-5-carbaldehyde (580 mg, 5.22 mmol, in 3 mL THF) was introduced. The reaction mixture was allowed to warm to −20° C. over 45 minutes at which time the reaction was quenched with aqueous $NH_4Cl$ solution. The aqueous portion was extracted with EtOAc (5×40 mL) and the combined organics were washed with brine, dried over $MgSO_4$, filtered and concentrated to dryness. Chromatography on silica gel (5% $CH_3CN$-DCM increasing to 30% $CH_3CN$+2% MeOH) provided the title compound as an off white amorphous solid.

Intermediate 9: Step b (4-Chloro-2-methoxy-3-(4-(trifluoromethyl)benzyl)quinolin-6-yl)(1-methyl-1H-1,2,3-triazol-5-yl)methanone

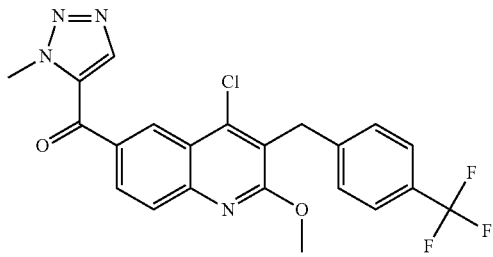 [SMILES: COc1nc2ccc(C(=O)c3cnnn3C)cc2c(Cl)c1Cc1ccc(C(F)(F)F)cc1]

To a flask containing (4-chloro-2-methoxy-3-(4-(trifluoromethyl)benzyl)quinolin-6-yl)(1-methyl-1H-1,2,3-triazol-5-yl)methanol (745 mg, 1.61 mmol, Intermediate 9: step a) was added 1,4-dioxane (35 mL), producing a suspension at room temperature. Warming to 45° C. formed a homogeneous solution. Then manganese dioxide (719 mg, 8.28 mmol) was introduced and the mixture was heated to 85° C. After 2 hours, the contents were filtered through Celite® while still warm and rinsed with THF. The solution was concentrated and the crude material was triturated with Et$_2$O to provide the title compound as a bright white solid. The mother liquors were re-purified by concentrating and re-triturating with Et$_2$O to afford additional title compound.

Intermediate 10: Step a (4-Chloro-2-methoxy-3-(4-(trifluoromethyl)benzyl)quinolin-6-yl)(2,6-dimethylpyridin-3-yl)methanol

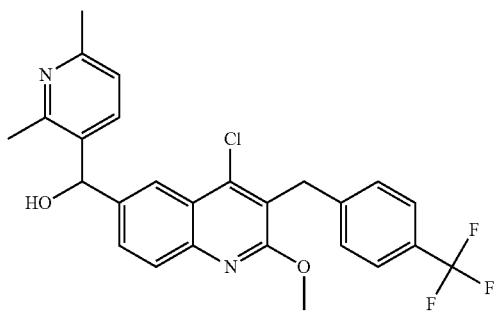 [SMILES: COc1nc2ccc(C(O)c3ccc(C)nc3C)cc2c(Cl)c1Cc1ccc(C(F)(F)F)cc1]

To a flask containing 6-bromo-4-chloro-2-methoxy-3-(4-(trifluoromethyl)benzyl)quinoline (1.85 g, 4.3 mmol, Intermediate 5: step d) was added THF (45 mL) at room temperature which resulted in a colorless homogeneous solution. The solution was cooled to −70° C. and then n-BuLi (2.5 M in hexanes, 1.75 mL, 4.38 mmol) was added dropwise. After 2 minutes, 2,6-dimethylnicotinaldehyde (755 mg, 5.50 mmol, in 2 mL THF) was introduced and the color of the mixture changed from a reddish-brown to green. The reaction mixture was allowed to warm to −20° C. over 40 minutes at which time the reaction was quenched with aqueous NH$_4$Cl solution. The aqueous portion was extracted with EtOAc (3×50 mL) and the combined organics were washed with brine, dried over MgSO$_4$, filtered and concentrated to dryness. Chromatography on silica gel (10% acetone-hexane increasing to 30% acetone) afforded the title compound.

Intermediate 10: Step b (4-Chloro-2-methoxy-3-(4-(trifluoromethyl)benzyl)quinolin-6-yl)(2,6-dimethylpyridin-3-yl)methanone

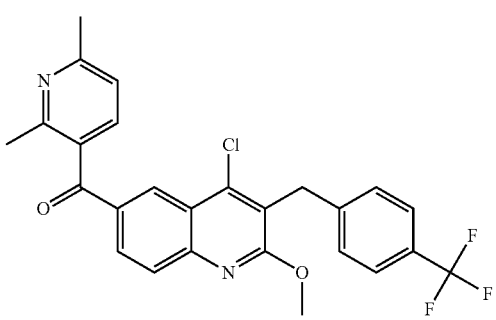 [SMILES: COc1nc2ccc(C(=O)c3ccc(C)nc3C)cc2c(Cl)c1Cc1ccc(C(F)(F)F)cc1]

To a flask containing (4-chloro-2-methoxy-3-(4-(trifluoromethyl)benzyl)quinolin-6-yl)(2,6-dimethylpyridin-3-yl)methanol (1.51 g, 3.1 mmol, Intermediate 10: step a) was added 1,4-dioxane (50 mL) followed by activated manganese dioxide (1.31 g, 15.1 mmol) and the reaction mixture was heated to reflux. After 1 hour, the contents were filtered while still hot through a pad of Celite® and rinsed with THF. The resulting light yellow solution was concentrated and chromatographed on silica gel (10% acetone-hexane increasing to 25% acetone) to provide the title compound as a light yellowish amorphous solid.

Intermediate 11: Step a (4-Chloro-2-methoxy-3-(4-(trifluoromethyl)benzyl)quinolin-6-yl)(2,4-dimethyloxazol-5-yl)methanol

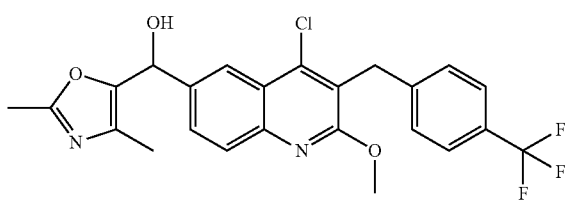 [SMILES: COc1nc2ccc(C(O)c3oc(C)nc3C)cc2c(Cl)c1Cc1ccc(C(F)(F)F)cc1]

To a flask containing 6-bromo-4-chloro-2-methoxy-3-(4-(trifluoromethyl)benzyl)quinoline (1.5 g, 3.48 mmol, Intermediate 5: step d) was added THF (65 mL) and the solution was cooled to −70° C. n-BuLi (2.5 M in hexanes, 1.62 mL, 4.04 mmol) was then added dropwise. After 2 minutes, 2,4-dimethyloxazole-5-carbaldehyde (520 mg, 4.16 mmol in 3 mL THF) was introduced. After 25 minutes the reaction mixture was quenched with aqueous NH$_4$Cl solution and the aqueous portion was extracted with EtOAc (5×40 mL). The combined organics were washed with brine, dried over MgSO$_4$, filtered and concentrated to dryness. Chromatography on silica gel (10% CH$_3$CN-DCM increasing to 30% CH$_3$CN+1% MeOH) provided the title compound as a white amorphous solid.

Intermediate 11: Step b (4-Chloro-2-methoxy-3-(4-(trifluoromethyl)benzyl)quinolin-6-yl)(2,4-dimethyloxazol-5-yl)methanone

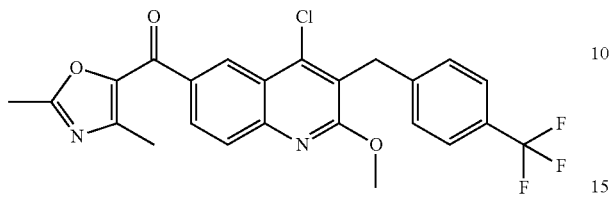

To a flask containing (4-chloro-2-methoxy-3-(4-(trifluoromethyl)benzyl)quinolin-6-yl)(2,4-dimethyloxazol-5-yl)methanol (960 mg, 2.01 mmol, Intermediate 11: step a) was added 1,4-dioxane (50 mL) followed by manganese dioxide (900 mg, 103 mmol) at room temperature. The mixture was heated to 85° C., for 60 minutes, and then the contents were filtered through Celite® while still warm and rinsed with THF. The solution was concentrated and the crude material was triturated with Et$_2$O to afford the title compound as a white solid. The mother liquors were re-purified by chromatography on silica gel (2% MeOH-DCM increasing to 5% MeOH) to provide additional title compound.

Intermediate 12: Step a (4-Chloro-2-methoxy-3-(4-(trifluoromethyl)benzyl)quinolin-6-yl)(1-methyl-1H-imidazol-5-yl)methanol

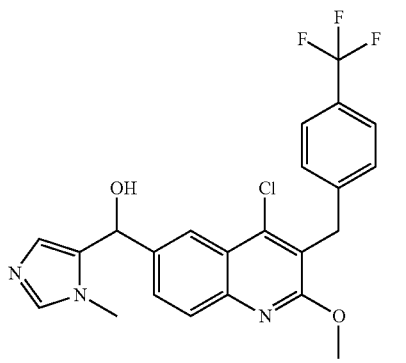 [SMILES: COc1nc2ccc(C(O)c3cncn3C)cc2c(Cl)c1Cc1ccc(C(F)(F)F)cc1]

To a flask containing 6-bromo-4-chloro-2-methoxy-3-(4-(trifluoromethyl)benzyl)quinoline (3.0 g, 6.97 mmol, Intermediate 5: step d) was added THF (40 mL) and the solution was cooled to −70° C. n-BuLi (2.5 M in hexanes, 2.8 mL, 7 mmol) was then added dropwise. After 2 minutes, 1-methyl-1H-imidazole-5-carbaldehyde (1.2 g, 9 mmol, in 10 mL THF) was introduced. After 15 minutes, the dry-ice bath was replaced with a 0° C. bath. After 35 minutes the reaction mixture was quenched with aqueous NH$_4$Cl solution and the aqueous portion was extracted with EtOAc:THF (10:2, 5×50 mL). The combined organics were washed with brine, dried over Na$_2$SO$_4$, filtered and concentrated to dryness. Chromatography on silica gel (30% acetone-DCM increasing to 5% MeOH) provided the title compound.

Intermediate 12: Step b (4-Chloro-2-methoxy-3-(4-(trifluoromethyl)benzyl)quinolin-6-yl)(1-methyl-1H-imidazol-5-yl)methanone

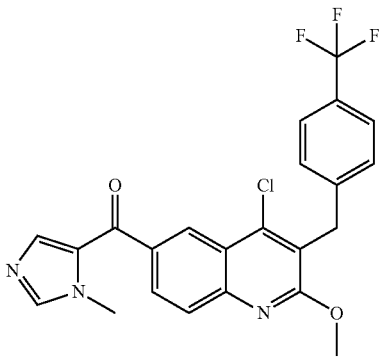 [SMILES: COc1nc2ccc(C(=O)c3cncn3C)cc2c(Cl)c1Cc1ccc(C(F)(F)F)cc1]

To a flask containing (4-chloro-2-methoxy-3-(4-(trifluoromethyl)benzyl)quinolin-6-yl)(1-methyl-1H-imidazol-5-yl)methanol (2.3 g, 4.98 mmol, Intermediate 12: step a) was added 1,4-dioxane (80 mL) to give a suspension at room temperature. The flask was fitted with a reflux condenser and heated briefly to 50° C. which resulted in a homogeneous solution. Then, activated manganese dioxide (1.73 g, 19.9 mmol) was introduced and the temperature was raised to 80° C. After 65 minutes, the reaction mixture was filtered through Celite® and rinsed with warm THF. The effluent was concentrated to dryness to provide the title compound as a white solid.

Intermediate 13: Step a tert-Butyl-3-((4-chloro-2-methoxy-3-(4-(trifluoromethyl)benzyl)quinolin-6-yl)(hydroxy)methyl)azetidine-1-carboxylate

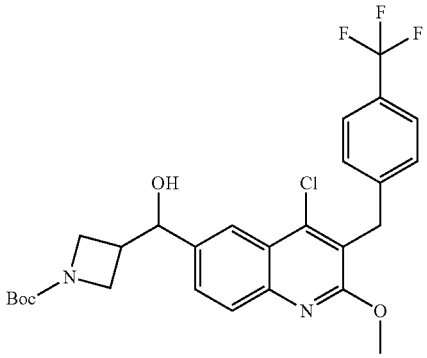 [SMILES: COc1nc2ccc(C(O)C3CN(C(=O)OC(C)(C)C)C3)cc2c(Cl)c1Cc1ccc(C(F)(F)F)cc1]

To a flask containing 6-bromo-4-chloro-2-methoxy-3-(4-(trifluoromethyl)benzyl)quinoline (1.0 g, 2.32 mmol, Intermediate 5: step d) was added THF (30 mL) at room temperature which resulted in a colorless homogeneous mixture. The solution was cooled to −75° C. and then n-BuLi (2.5 M in hexanes, 1.08 mL, 2.69 mmol) was added dropwise. After 2 minutes, tert-butyl 3-formylazetidine-1-carboxylate (545 mg, 2.94 mmol in 3 mL THF) was introduced. After 5 minutes, the reaction mixture was transferred to an ice-water bath and stirring was continued for 30 minutes. The reaction mixture was quenched with aqueous NH₄Cl solution and the aqueous portion was extracted with EtOAc (5×40 mL). The combined organics were washed with brine, dried over MgSO₄, filtered and concentrated to dryness. The crude material was chromatographed on silica gel (20% EtOAc-hexanes increasing to 50% EtOAc) to provide the title compound as a white solid.

Intermediate 13: Step b tert-Butyl-3-(4-chloro-2-methoxy-3-(4-(trifluoromethyl)benzyl)quinoline-6-carbonyl)azetidine-1-carboxylate

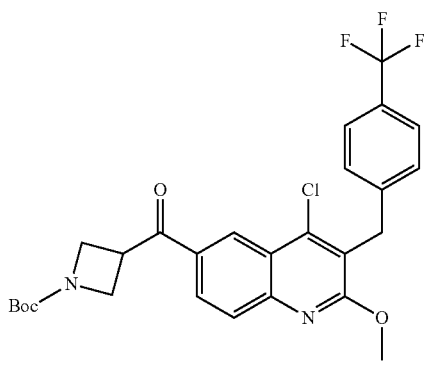 [SMILES: COc1nc2ccc(C(=O)C3CN(C(=O)OC(C)(C)C)C3)cc2c(Cl)c1Cc1ccc(C(F)(F)F)cc1]

To a flask containing tert-butyl 3-((4-chloro-2-methoxy-3-(4-(trifluoromethyl)benzyl)quinolin-6-yl)(hydroxy)methyl)azetidine-1-carboxylate (4.75 g, 8.85 mmol, Intermediate 13: step a) was added 1,4-dioxane (200 mL) and THF (100 mL) to give a homogeneous solution. Activated MnO₂ (5.0 g, 57.5 mmol) was then introduced and the mixture was heated to 85° C. After 3 hours the reaction mixture was filtered through Celite® while still warm and rinsed with additional THF and concentrated. Chromatography on silica gel (10% acetone-hexane increasing to 25% acetone) provided the title compound as an off white solid.

Example 1

1-(2,4-Dichloro-3-phenylquinolin-6-yl)-1-(3-methyl-isoxazol-5-yl)pentan-1-ol.TFA

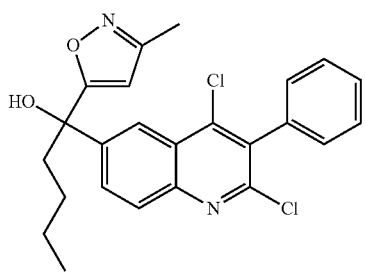 [SMILES: CCCCC(O)(c1ccc2nc(Cl)c(-c3ccccc3)c(Cl)c2c1)c1cc(C)no1]

5-Bromo-2-methoxypyridine (0.019 mL, 0.15 mmol) was added to a solution of (2,4-dichloro-3-phenylquinolin-6-yl)(3-methylisoxazol-5-yl)methanone (44.1 mg, 0.115 mmol, Intermediate 3: step b) in THF (1 mL) under a nitrogen atmosphere. The mixture was cooled to −78° C. and n-BuLi (1.6 M in hexane, 0.094 mL, 0.150 mmol) was added dropwise. The mixture was stirred at −78° C. for 30 minutes, then moved to an ice bath and stirred for 30 minutes. The reaction was quenched by addition of saturated aqueous NH₄Cl and was diluted with water. The mixture was extracted three times with EtOAc. The organic phase was dried (Na₂SO₄), filtered, and concentrated to dryness. The crude product was purified by RP-HPLC (10-90% CH₃CN—H₂O, 0.1% TFA) to afford the title compound along with the intended product (2,4-dichloro-3-phenylquinolin-6-yl)(6-methoxypyridin-3-yl)(3-methylisoxazol-5-yl)methanol. $^1$H NMR (400 MHz, DMSO-d₆) δ 8.41 (s, 1H), 8.06 (d, J=8.80 Hz, 1H), 7.93 (d, J=8.80 Hz, 1H), 7.47-7.60 (m, 3H), 7.38-7.47 (m, 2H), 6.55 (br. s., 1H), 6.33 (s, 1H), 2.22-2.36 (m, 2H), 2.20 (s, 3H), 1.17-1.36 (m, 3H), 0.92-1.10 (m, 1H), 0.81 (t, J=6.97 Hz, 3H); MS m/e 441.1 (M+H)⁺.

Example 2

1-(2,4-Dichloro-3-phenylquinolin-6-yl)-1-(3-methyl-isoxazol-5-yl)propan-1-ol.TFA

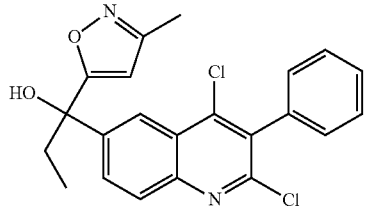 [SMILES: CCC(O)(c1ccc2nc(Cl)c(-c3ccccc3)c(Cl)c2c1)c1cc(C)no1]

Ethylmagnesium bromide (3 M in Et₂O, 0.064 mL, 0.193 mmol) was added dropwise to a solution of 5-bromo-1-methyl-1H-imidazole (31.0 mg, 0.193 mmol) in DCM (1 mL) under a nitrogen atmosphere. The mixture was stirred at room temperature for 15 minutes, then was cooled to 0° C. A solution of (2,4-dichloro-3-phenylquinolin-6-yl)(3-methyl-isoxazol-5-yl)methanone (49.2 mg, 0.128 mmol, Intermediate 3: step b) in DCM (2 mL) was added via cannula. The mixture was stirred at room temperature for 2 hours. The reaction was quenched by addition of saturated aqueous NH₄Cl and was diluted with water. The mixture was extracted three times with EtOAc. The organic phase was dried (Na₂SO₄), filtered, and concentrated to dryness. The crude product was purified by RP-HPLC (10-90% CH₃CN—H₂O, 0.1% TFA) to afford the title compound along with the intended product (2,4-dichloro-3-phenylquinolin-6-yl)(1-methyl-1H-imidazol-5-yl)(3-methylisoxazol-5-yl)methanol. $^1$H NMR (400 MHz, DMSO-d₆) δ 8.41 (s, 1H), 8.06 (d, J=9.05 Hz, 1H), 7.92 (d, J=8.80 Hz, 1H), 7.47-7.63 (m, 3H), 7.36-7.47 (m, 2H), 6.53 (br. s., 1H), 6.34 (s, 1H), 2.23-2.38 (m, 2H), 2.20 (s, 3H), 0.76 (t, J=7.21 Hz, 3H); MS m/e 413.1 (M+H)⁺.

Example 3

Cyclopropyl(2,4-dichloro-3-phenylquinolin-6-yl)(1-methyl-1H-imidazol-5-yl)methanol

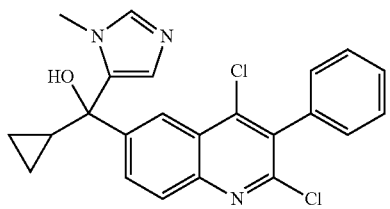 [SMILES: Cn1cncc1C(O)(c1ccc2nc(Cl)c(-c3ccccc3)c(Cl)c2c1)C1CC1]

Cyclopropylmagnesium bromide (0.5 M in THF, 0.6 mL, 0.3 mmol) was added dropwise to a solution of (2,4-dichloro-3-phenylquinolin-6-yl)(1-methyl-1H-imidazol-5-yl)methanone (57.3 mg, 0.15 mmol, Intermediate 2: step b) in THF (1 mL) at 0° C. The mixture was stirred at 0° C. for 5 minutes, then the ice bath was removed and the mixture was stirred for 3 hours. The reaction was quenched by the addition of saturated aqueous NH$_4$Cl and was diluted with water. The mixture was extracted three times with EtOAc. The organic phase was dried (Na$_2$SO$_4$), filtered, and concentrated. The residue was purified by flash column chromatography (silica gel, 0-4% MeOH-DCM) to afford the title compound. $^1$H NMR (400 MHz, DMSO-d$_6$) δ 8.20 (d, J=1.71 Hz, 1H), 8.03 (d, J=8.80 Hz, 1H), 7.66 (dd, J=1.96, 8.80 Hz, 1H), 7.46-7.61 (m, 4H), 7.39-7.46 (m, 2H), 7.30 (d, J=0.98 Hz, 1H), 5.82 (s, 1H), 3.14 (s, 3H), 1.63-1.74 (m, 1H), 0.53-0.71 (m, 2H), 0.19-0.42 (m, 2H); MS m/e 424.0 (M+H)$^+$.

Example 4

1-(2,4-Dichloro-3-phenylquinolin-6-yl)-1-(1-methyl-1H-imidazol-5-yl)pentan-1-ol.TFA

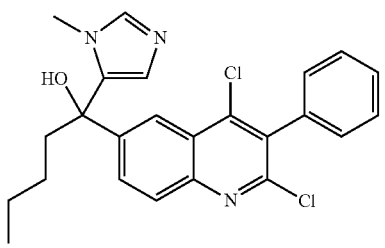 [SMILES: CCCCC(O)(c1ccc2nc(Cl)c(-c3ccccc3)c(Cl)c2c1)c1cncn1C]

n-BuLi (1.6 M in hexane, 0.063 mL, 0.101 mmol) was added dropwise to a solution of (2,4-dichloro-3-phenylquinolin-6-yl)(1-methyl-1H-imidazol-5-yl)methanone (35 mg, 0.092 mmol, Intermediate 2: step b) in THF (1 mL) at −78° C. The mixture was stirred at −78° C. for 5 minutes, then was transferred to an ice bath and stirred for an additional 45 minutes. The reaction was quenched by the addition of saturated aqueous NH$_4$Cl and was diluted with water. The mixture was extracted three times with EtOAc. The combined organic phases were dried (Na$_2$SO$_4$), filtered, and concentrated to dryness. The title compound was isolated by RP-HPLC (10-90% CH$_3$CN—H$_2$O, 0.1% TFA). $^1$H NMR (400 MHz, DMSO-d$_6$) δ 8.98 (s, 1H), 8.37 (d, J=1.71 Hz, 1H), 8.07 (d, J=8.80 Hz, 1H), 8.02 (d, J=1.47 Hz, 1H), 7.68 (dd, J=1.96, 8.80 Hz, 1H), 7.47-7.62 (m, 3H), 7.39-7.48 (m, 2H), 6.58 (s, 1H), 3.42 (s, 3H), 2.25-2.36 (m, 2H), 1.37-1.51 (m, 1H), 1.16-1.34 (m, 2H), 0.80 (t, J=7.34 Hz, 3H), 0.67-0.79 (m, 1H); MS m/e 440.1 (M+H)$^+$.

Example 5

1-(2,4-Dichloro-3-phenylquinolin-6-yl)-2-methyl-1-(1-methyl-1H-imidazol-5-yl)propan-1-ol

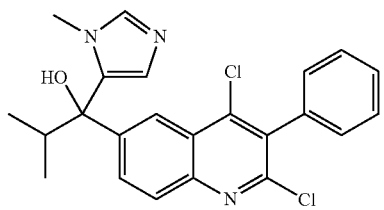 [SMILES: CC(C)C(O)(c1ccc2nc(Cl)c(-c3ccccc3)c(Cl)c2c1)c1cncn1C]

Isopropylmagnesium chloride (2.0 M in THF, 0.056 mL, 0.11 mmol) was added dropwise to a solution of (2,4-dichloro-3-phenylquinolin-6-yl)(1-methyl-1H-imidazol-5-yl)methanone (35 mg, 0.092 mmol, Intermediate 2: step b) in THF (1 mL) at 0° C. The mixture was stirred at 0° C. for 5 minutes, then the ice bath was removed and the mixture was stirred for 25 minutes. The reaction was quenched by the addition of saturated aqueous NH$_4$Cl and was diluted with water. The mixture was extracted three times with EtOAc. The organic phase was dried (Na$_2$SO$_4$), filtered, and concentrated to dryness. The residue was purified by RP-HPLC (10-90% CH$_3$CN—H$_2$O, 0.1% TFA), then was converted to the free base (saturated aqueous NaHCO$_3$/DCM extraction) and re-purified by flash column chromatography (silica gel, 25-70% acetone-EtOAc) to afford the title compound. $^1$H NMR (400 MHz, CDCl$_3$) δ 8.32 (s, 1H), 7.99 (d, J=8.80 Hz, 1H), 7.62 (d, J=8.80 Hz, 1H), 7.46-7.57 (m, 3H), 7.32-7.39 (m, 2H), 7.28-7.32 (m, 1H), 7.18-7.25 (m, 1H), 3.29 (s, 3H), 2.65-2.76 (m, 1H), 1.24 (d, J=6.60 Hz, 3H), 0.72 (d, J=6.85 Hz, 3H); MS m/e 426.1 (M+H)$^+$.

Example 6

1-(4-Chloro-2-methoxy-3-(4-(methylsulfonyl)benzyl)quinolin-6-yl)-1-(1-methyl-1H-imidazol-5-yl)propan-1-ol

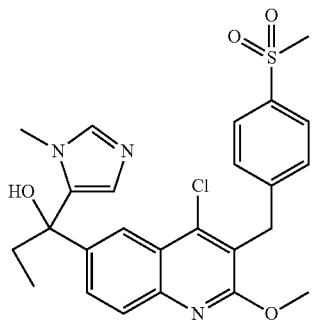 [SMILES: CCC(O)(c1ccc2nc(OC)c(Cc3ccc(S(C)(=O)=O)cc3)c(Cl)c2c1)c1cncn1C]

Ethyl magnesium bromide solution (3 M in Et$_2$O, 0.1 mL, 0.334 mmol) was added slowly to a solution of 5-bromo-2-(trifluoromethyl)pyridine (0.075 g, 0.334 mmol) in dry THF (3 mL). The resulting cloudy solution was stirred at room temperature for 20 minutes, cooled to 0° C. and then (4-chloro-2-methoxy-3-(4-(methylsulfonyl)benzyl)quinolin-6-yl)(1-methyl-1H-imidazol-5-yl)methanone (0.056 g, 0.119 mmol, Intermediate 7: step e) in dry DCM (1 mL) was added. The resulting suspension was stirred at room temperature for 10 minutes then heated in a 60° C. oil bath, for 6 hours, then at 80° C. for an additional 12 hours. The mixture was cooled to room temperature, then H$_2$O was added followed by 6 N aqueous HCl to bring the contents to a neutral pH. The solvents were removed under reduced pressure and the product extracted out with CH$_2$Cl$_2$ (2×). The combined organic extract was dried (Na$_2$SO$_4$), filtered, evaporated in vacuo and chromatographed (0-10% MeOH in DCM) to provide a yellow solid by-product. Further purification by RP-HPLC (water/acetonitrile/0.1% TFA) of this by-product provided the title compound as a white solid. $^1$H NMR (400 MHz, CD$_3$OD) δ 8.80 (s, 1H), 8.32 (d, J=2.0 Hz, 1H), 7.84 (d, J=7.6 Hz, 4H), 7.51 (d, J=8.6 Hz, 3H), 4.44 (s, 2H), 4.07 (s, 3H), 3.53 (s, 3H), 3.07 (s, 3H), 2.26-2.48 (m, 2H), 0.83 (t, J=7.0 Hz, 3H); MS (ESI) 500 [M+H]$^+$.

Example 7a 1-(3-(1-(4-Chloro-2-methoxy-3-(4-(trifluoromethyl) benzyl)quinolin-6-yl)-1-hydroxyprop-2-yn-1-yl) azetidin-1-yl)ethanone

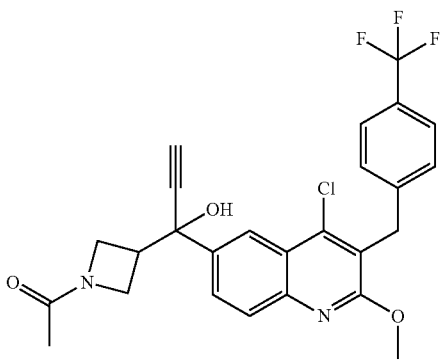 [SMILES: C#CC(O)(c1ccc2nc(OC)c(Cc3ccc(C(F)(F)F)cc3)c(Cl)c2c1)C1CN(C(C)=O)C1]

To a flask containing crude 1-(azetidin-3-yl)-1-(4-chloro-2-methoxy-3-(4-(trifluoromethyl)-benzyl)quinolin-6-yl) prop-2-yn-1-ol (130 mg, 0.28 mmol, Example 16) was added DCM (10 mL) followed by Et$_3$N (0.2 mL, 1.44 mmol) and acetic anhydride (0.1 mL, 1.06 mmol) at room temperature. The mixture was heated to 40° C. for 2 hours and then quenched with a solution of saturated aqueous NaHCO$_3$. The aqueous portion was extracted with DCM (3×35 mL) and the combined organics were dried over MgSO$_4$, filtered and concentrated to dryness. Chromatography on silica gel using (5% MeOH-DCM) provided the title compound as an off white amorphous solid. $^1$H NMR (500 MHz, CD$_3$OD) δ 8.44 (d, J=1.9 Hz, 1H), 7.94 (d, J=8.7 Hz, 1H), 7.91-7.82 (m, 1H), 7.55 (d, J=8.2 Hz, 2H), 7.42 (d, J=8.1 Hz, 2H), 4.40 (s, 2H), 4.36-4.18 (m, 1H), 4.16-4.01 (m, 4H containing a singlet at 4.07), 4.05-3.98 (m, 1H), 3.93-3.80 (m, 1H), 3.28 (s, 1H), 3.24-3.09 (m, 1H), 1.85 (d, J=3.3 Hz, 3H); MS (ESI): mass calcd. for C$_{26}$H$_{22}$ClF$_3$N$_2$O$_3$, 502.1, m/z found 503.2 [M+H]$^+$. 1-(3-(1-(4-chloro-2-methoxy-3-(4-(trifluoromethyl)benzyl) quinolin-6-yl)-1-hydroxyprop-2-yn-1-yl)azetidin-1-yl)ethanone was purified by chiral SFC: (Stationary phase: CHIRALPAK AD-H, 5 μm, 250×20 mm), Mobile phase: 70% CO$_2$, 30% MeOH), to give 2 enantiomers. The first eluting enantiomer was Example 7b and the second eluting enantiomer was Example 7c.

Example 8 tert-Butyl-3-(1-(4-chloro-2-methoxy-3-(4-(trifluoromethyl)benzyl)quinolin-6-yl)-1-hydroxyprop-2-yn-1-yl)azetidine-1-carboxylate

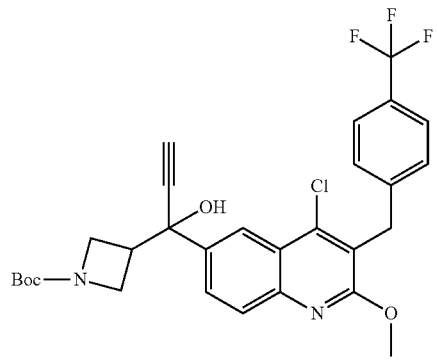 [SMILES: C#CC(O)(c1ccc2nc(OC)c(Cc3ccc(C(F)(F)F)cc3)c(Cl)c2c1)C1CN(C(=O)OC(C)(C)C)C1]

To a flask containing tert-butyl 3-(4-chloro-2-methoxy-3-(4-(trifluoromethyl)benzyl)quinoline-6-carbonyl)azetidine-1-carboxylate (500 mg, 0.93 mmol, Intermediate 13: step b) was added THF (10 mL) and the solution was cooled to 0° C. Then, TMS-lithiumacetylide (0.5 M in Et$_2$O, 2.0 mL, 1 mmol) was added and the reaction was allowed to warm gradually to room temperature. After 5 hours, additional TMS-lithiumacetylide (2 mL, 1.0 mmol, 0.5 M in Et$_2$O) was added and the reaction mixture was stirred at room temperature overnight. After 24 hours, the mixture was quenched with aqueous NH$_4$Cl solution and extracted with EtOAc (3×30 mL). The combined organics were washed with brine, dried over MgSO$_4$, filtered and concentrated to dryness. Chromatography on silica gel (1% acetone-DCM increasing to 5% acetone) provided a mixture of title compound and the silylated title compound. To a flask containing tert-butyl-3-(1-(4-chloro-2-methoxy-3-(4-(trifluoromethyl)benzyl)quinolin-6-yl)-1-hydroxy-3-(trimethylsilyl)prop-2-yn-1-yl)azetidine-1-carboxylate (220 mg, 0.35 mmol) was added MeOH (8 mL) followed by 2 M aqueous KOH (0.4 mL) at room temperature. After stirring for 15 minutes, the reaction was concentrated and chromatographed directly on silica gel (5% acetone-DCM increasing to 25% acetone) to provide the title compound as an amorphous white solid. $^1$H NMR (500 MHz, CDCl$_3$) δ 8.36 (d, J=1.1 Hz, 1H), 7.88-7.79 (m, 2H), 7.50 (d, J=8.2 Hz, 2H), 7.38 (d, J=8.1 Hz, 2H), 4.35 (s, 2H), 4.19-4.12 (m, 1H), 4.07 (s, 3H), 4.01-3.94 (m, 1H), 3.91-3.79 (m, 2H), 3.14-3.03 (m, 1H), 2.81 (s, 1H), 2.68 (s, 1H), 1.43 (s, 9H); MS (ESI): mass calcd. for C$_{29}$H$_{28}$ClF$_3$N$_2$O$_4$, 560.2, m/z found 504.9 [M-t-Butyl]$^+$.

Example 9a 1-(4-Chloro-2-methoxy-3-(4-(trifluoromethyl)benzyl)quinolin-6-yl)-1-(1-methyl-1H-imidazol-5-yl)ethanol

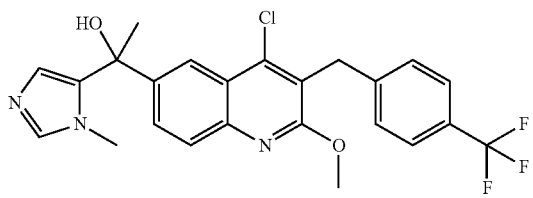 [SMILES: COc1nc2ccc(C(C)(O)c3cncn3C)cc2c(Cl)c1Cc1ccc(C(F)(F)F)cc1]

To a flask containing (4-chloro-2-methoxy-3-(4-(trifluoromethyl)benzyl)quinolin-6-yl)(1-methyl-1H-imidazol-5-yl)methanone (400 mg, 0.87 mmol, Intermediate 12: step b) was added THF (20 mL) and the solution was cooled to −43° C. (CH$_3$CN—CO$_2$). MeLi (1.6 M in Et$_2$O, 0.63 mL, 1.01 mmol) was then introduced. After 30 minutes, the reaction mixture was quenched with saturated aqueous NH$_4$Cl solution. The aqueous portion was extracted with EtOAc (4×30 mL) and the combined organics were washed with brine, dried over MgSO$_4$, filtered and concentrated to dryness. Chromatography on silica gel (30% CH$_3$CN-DCM increasing to 3% MeOH-DCM) provided the title compound as a white amorphous solid. $^1$H NMR (400 MHz, CDCl$_3$) δ 8.24 (d, J=1.9 Hz, 1H), 7.77 (d, J=8.9 Hz, 1H), 7.49 (dd, J=8.6, 2.2 Hz, 3H), 7.40 (d, J=8.1 Hz, 2H), 7.34 (s, 1H), 7.17 (d, J=0.8 Hz, 1H), 4.35 (s, 2H), 4.07 (s, 3H), 3.25 (s, 3H), 3.0 (br. s, 1H), 1.99 (s, 3H); MS (ESI): mass calcd. for C$_{24}$H$_{21}$ClF$_3$N$_3$O$_2$, 475.1, m/z found 475.9 [M+H]+. 1-(4-Chloro-2-methoxy-3-(4-(trifluoromethyl)benzyl)quinolin-6-yl)-1-(1-methyl-1H-imidazol-5-yl)ethanol was purified by chiral SFC: (Stationary phase: CHIRALCEL OD-H, 5 μm, 250×20 mm), Mobile phase: 70% CO$_2$, 30% MeOH), to give 2 enantiomers. The first eluting enantiomer was Example 9b and the second eluting enantiomer was Example 9c.

Example 10a 1-(4-Chloro-2-methoxy-3-(4-(trifluoromethyl)benzyl)quinolin-6-yl)-1-(2,4-dimethyloxazol-5-yl)ethanol

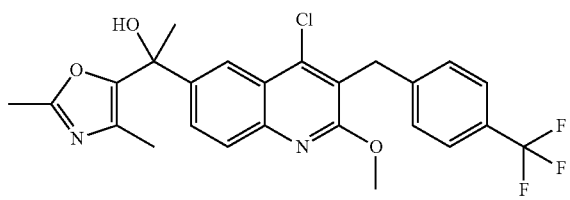 [SMILES: COc1nc2ccc(C(C)(O)c3oc(C)nc3C)cc2c(Cl)c1Cc1ccc(C(F)(F)F)cc1]

To a flask containing (4-chloro-2-methoxy-3-(4-(trifluoromethyl)benzyl)quinolin-6-yl)(2,4-dimethyloxazol-5-yl)methanone (0.225 g, 0.474 mmol, Intermediate 11: step b) was added THF (15 mL). The solution was cooled to −78° C. and MeLi (1.6 M in Et$_2$O, 0.36 mL, 0.58 mmol) was introduced which resulted in an immediate light orange homogeneous mixture. After 35 minutes the reaction mixture was quenched with aqueous NH$_4$Cl solution. The aqueous portion was extracted with EtOAc (4×30 mL) and the combined organics were washed with brine, dried over MgSO$_4$, filtered and concentrated to dryness. Chromatography on silica gel (10% CH$_3$CN-DCM increasing to 25% CH$_3$CN and then to 5% MeOH) provided the title compound as a pale yellow amorphous solid. $^1$H NMR (500 MHz, CDCl$_3$) δ 8.26 (d, J=1.9 Hz, 1H), 7.81 (d, J=8.7 Hz, 1H), 7.61 (dd, J=8.7, 2.1 Hz, 1H), 7.50 (d, J=8.1 Hz, 2H), 7.39 (d, J=8.0 Hz, 2H), 4.35 (s, 2H), 4.07 (s, 3H), 2.57 (s, 1H), 2.39 (s, 3H), 1.99 (s, 3H), 1.92 (s, 3H); MS (ESI): mass calcd. for C$_{25}$H$_{22}$ClF$_3$N$_2$O$_3$, 490.1, m/z found 491.1 [M+H]$^+$. 1-(4-Chloro-2-methoxy-3-(4-(trifluoromethyl)benzyl)quinolin-6-yl)-1-(2,4-dimethyloxazol-5-yl)ethanol was purified by chiral chromatography (Chiralpak AD-H, solvent: 95% heptane/5% ethanol), to give 2 enantiomers. The first eluting enantiomer was Example 10b and the second eluting enantiomer was Example 10c.

Example 11a 1-(4-Chloro-2-methoxy-3-(4-(trifluoromethyl)benzyl)quinolin-6-yl)-1-(1-methyl-1H-1,2,3-triazol-5-yl)ethanol

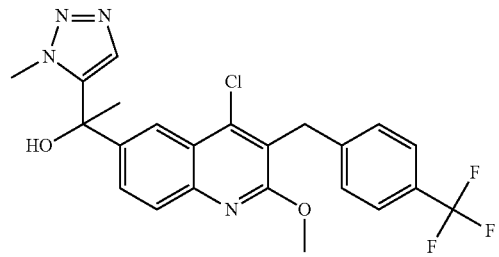 [SMILES: COc1nc2ccc(C(C)(O)c3cnnn3C)cc2c(Cl)c1Cc1ccc(C(F)(F)F)cc1]

To flask containing (4-chloro-2-methoxy-3-(4-(trifluoromethyl)benzyl)quinolin-6-yl)(1-methyl-1H-1,2,3-triazol-5-yl)methanone (250 mg, 0.54 mmol, Intermediate 9: step b) was added THF (15 mL). The solution was cooled to −78° C. and MeLi (1.6 M in Et$_2$O, 0.4 mL, 0.64 mmol) was introduced. The reaction mixture was quenched after 25 minutes with aqueous NH$_4$Cl solution and the aqueous portion was extracted with EtOAc (4×30 mL). The combined organics were washed with brine, dried over MgSO$_4$, filtered and concentrated to dryness to afford an off white solid. Chromatography on silica gel (10% CH$_3$CN-DCM increasing to 30% CH$_3$CN) provided the title compound as a white amorphous solid. $^1$H NMR (500 MHz, CDCl$_3$) δ 8.21 (d, J=2.1 Hz, 1H), 7.80 (d, J=8.7 Hz, 1H), 7.74 (d, J=2.9 Hz, 1H), 7.50 (d, J=8.2 Hz, 2H), 7.45-7.35 (m, 3H), 4.35 (s, 2H), 4.07 (s, 3H), 3.71 (s, 3H), 2.82 (br. s, 1H), 2.06 (s, 3H); MS (ESI): mass calcd. for C$_{23}$H$_{20}$ClF$_3$N$_4$O$_2$, 476.1, m/z found 477.1 [M+H]$^+$. 1-(4-Chloro-2-methoxy-3-(4-(trifluoromethyl)benzyl)quinolin-6-yl)-1-(1-methyl-1H-1,2,3-triazol-5-yl)ethanol was purified by chiral SFC (Stationary phase: Lux 5 m cellulose-3, 4.6 mm×250 mm, Mobile phase: 12% EtOH, 0.2% Et$_3$N, 88% CO$_2$) to give 2 enantiomers. The first eluting enantiomer was Example 11b and the second eluting enantiomer was Example 11c.

Example 12a 1-(4-Chloro-2-methoxy-3-(4-(trifluoromethyl)benzyl)quinolin-6-yl)-1-(1,2-dimethyl-1H-imidazol-5-yl)ethanol

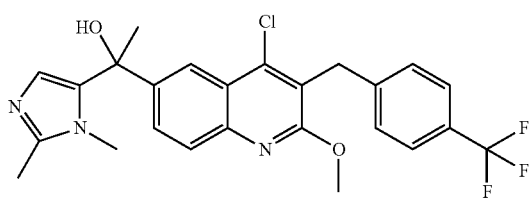 [SMILES: COc1nc2ccc(C(C)(O)c3cnc(C)n3C)cc2c(Cl)c1Cc1ccc(C(F)(F)F)cc1]

To a flask containing (4-chloro-2-methoxy-3-(4-(trifluoromethyl)benzyl)quinolin-6-yl)(1,2-dimethyl-1H-imidazol-5-yl)methanone (408 mg, 0.86 mmol, Intermediate 8: step b) was added THF (20 mL) and the solution was cooled to −78° C. MeLi (1.6 M in $Et_2O$, 0.6 mL, 0.96 mmol) was then introduced. After 25 minutes, the reaction mixture was quenched with aqueous $NH_4Cl$ solution and the aqueous portion was extracted with EtOAc (4×40 mL). The combined organics were washed with brine, dried over $MgSO_4$, filtered and concentrated to dryness. Chromatography on silica gel (5% MeOH-DCM increasing to 10% MeOH) provided the title compound as a white amorphous solid. $^1H$ NMR (500 MHz, $CDCl_3$) δ 8.26 (d, J=1.7 Hz, 1H), 7.77 (d, J=8.7 Hz, 1H), 7.50 (d, J=8.2 Hz, 3H), 7.40 (d, J=8.1 Hz, 2H), 7.04 (d, J=10.7 Hz, 1H), 4.35 (s, 2H), 4.07 (s, 3H), 3.14 (s, 3H), 2.29 (s, 3H), 1.95 (s, 3H); MS (ESI): mass calcd. for $C_{25}H_{23}ClF_3N_3O_2$, 489.1, m/z found 490.1 [M+H]$^+$. 1-(4-Chloro-2-methoxy-3-(4-(trifluoromethyl)benzyl)quinolin-6-yl)-1-(1,2-dimethyl-1H-imidazol-5-yl)ethanol was purified by chiral chromatography (Chiracel OD (20 μM) diacel, 50×41 cm, heptane:ethanol with 2% isopropylamine (90:10)), to give 2 enantiomers. The first eluting enantiomer was Example 12b and the second eluting enantiomer was Example 12c.

Example 13a 1-(4-Chloro-2-methoxy-3-(4-(trifluoromethyl)benzyl)quinolin-6-yl)-1-(2,6-dimethylpyridin-3-yl)ethanol

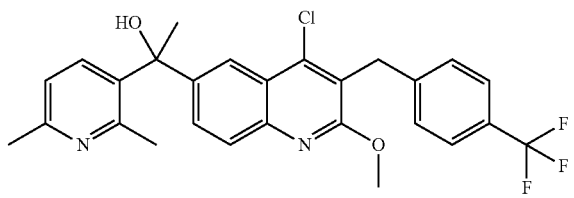 [SMILES: COc1nc2ccc(C(C)(O)c3ccc(C)nc3C)cc2c(Cl)c1Cc1ccc(C(F)(F)F)cc1]

To a flask containing (4-chloro-2-methoxy-3-(4-(trifluoromethyl)benzyl)quinolin-6-yl)(2,6-dimethylpyridin-3-yl)methanone (220 mg, 0.45 mmol, Intermediate 10: step b) was added THF (15 mL). The solution was cooled in a dry ice bath and then MeLi (1.6 M in $Et_2O$, 0.33 mL, 0.53 mmol) was introduced. After 40 minutes, the reaction was quenched with aqueous $NH_4Cl$ solution and the aqueous portion was extracted with EtOAc (4×30 mL). The combined organics were washed with brine, dried over $MgSO_4$, filtered and concentrated to dryness to afford an amber gum. Chromatography on silica gel (3% MeOH-DCM increasing to 5% MeOH) provided the title compound as a white amorphous solid. $^1H$ NMR (500 MHz, $CDCl_3$) δ 8.19 (d, J=2.0 Hz, 1H), 7.92 (d, J=8.0 Hz, 1H), 7.74 (d, J=8.7 Hz, 1H), 7.50 (d, J=8.2 Hz, 2H), 7.45-7.35 (m, 3H), 7.07 (d, J=8.0 Hz, 1H), 4.34 (s, 2H), 4.06 (s, 3H), 2.54 (s, 3H), 2.24 (s, 1H), 2.17 (s, 3H), 2.01 (s, 3H); MS (ESI): mass calcd. for $C_{27}H_{24}ClF_3N_2O_2$, 500.2, m/z found 501.1 [M+H]$^+$. 1-(4-Chloro-2-methoxy-3-(4-(trifluoromethyl)benzyl)quinolin-6-yl)-1-(2,6-dimethylpyridin-3-yl)ethanol was purified by chiral SFC (Stationary phase: Chiracel OD column (50×250 mm, 5 micron), Mobile phase: 12% EtOH-hexane with 0.2% $Et_3N$), to give 2 enantiomers. The first eluting enantiomer was Example 13b and the second eluting enantiomer was Example 13c.

Example 14a 1-(4-Chloro-2-methoxy-3-(4-(trifluoromethyl)benzyl)quinolin-6-yl)-1-(1,2-dimethyl-1H-imidazol-5-yl)prop-2-yn-1-ol

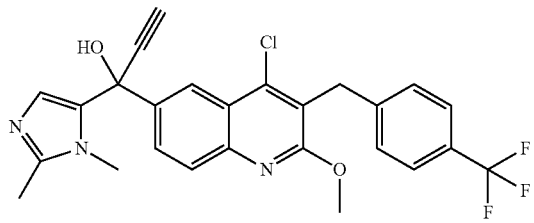 [SMILES: C#CC(O)(c1ccc2nc(OC)c(Cc3ccc(C(F)(F)F)cc3)c(Cl)c2c1)c1cnc(C)n1C]

To a flask containing (4-chloro-2-methoxy-3-(4-(trifluoromethyl)benzyl)quinolin-6-yl)(1,2-dimethyl-1H-imidazol-5-yl)methanone (405 mg, 0.85 mmol, Intermediate 8: step b) was added THF (20 mL). The solution was cooled in a dry-ice bath and TMS-lithiumacetylide (0.5 M in $Et_2O$, 1.8 mL, 0.9 mmol) was introduced. After 60 minutes, additional TMS-lithiumacetylide (5.0 mL, 2.5 mmol, 0.5 M in $Et_2O$) was added and the reaction mixture was stirred at room temperature overnight. After 24 hours, the reaction was quenched with aqueous $NH_4Cl$ solution and the aqueous portion was extracted with EtOAc (4×40 mL). The combined organics were washed with brine, dried over $MgSO_4$, filtered and concentrated. Chromatography on silica gel (2% MeOH-DCM increasing to 5% 2 M $NH_3$-MeOH) afforded the title compound and the silylated title compound. $^1H$ NMR (400 MHz, $CDCl_3$) δ 8.46 (d, J=1.9 Hz, 1H), 7.84-7.68 (m, 2H), 7.44 (dd, J=43.2, 8.2 Hz, 5H), 6.67 (s, 1H), 4.34 (s, 2H), 4.07 (s, 3H), 3.37 (s, 3H), 2.77 (s, 1H), 2.32-2.12 (m, 3H); MS (ESI): mass calcd. for $C_{26}H_{21}ClF_3N_3O_2$, 499.1, m/z found 500.1 [M+H]$^+$. 1-(4-Chloro-2-methoxy-3-(4-(trifluoromethyl)benzyl)quinolin-6-yl)-1-(1,2-dimethyl-1H-imidazol-5-yl)prop-2-yn-1-ol was purified by chiral chromatography (Chiralpak AD (20 μM) diacel (41 mm×41 mm), heptane:2-propanol with 2% isopropylamine (93:7)) to give 2 enantiomers. The first eluting enantiomer was Example 14b and the second eluting enantiomer was Example 14c.

Example 15

1-(2,4-Dichloro-3-phenylquinolin-6-yl)-1-(2,4-dimethylthiazol-5-yl)-2-methylpropan-1-ol

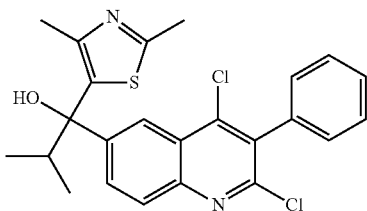 [SMILES: Cc1nc(C)c(C(O)(c2ccc3nc(Cl)c(-c4ccccc4)c(Cl)c3c2)C(C)C)s1]

To a flask containing 6-bromo-2,4-dichloro-3-phenylquinoline (275 mg, 0.78 mmol, Intermediate 1: step c) was added THF (10 mL) to give a homogeneous clear solution. The solution was cooled in a dry ice—acetone bath and n-BuLi (2.5 M in hexanes, 0.28 mL, 0.7 mmol) was added which resulted in an immediate orange-brown homogeneous solution. After 2 minutes, a solution of 1-(2,4-dimethylthiazol-5-yl)-2-methylpropan-1-one (200 mg, 1.09 mmol, Intermediate 4: step b) in 3 mL THF was added. The reaction mixture was maintained at −75° C. for 5 minutes then the dry ice—acetone bath was replaced with a 0° C. ice-bath. After 20 minutes the ice-bath was removed and the mixture was stirred at room temperature for 20 minutes. The mixture was quenched after a total reaction time of 45 minutes with aqueous $NH_4Cl$ solution and the aqueous portion was extracted with EtOAc (3×50 mL). The combined organics were washed with brine, dried over $MgSO_4$, filtered and concentrated to dryness. Chromatography on silica gel (100% DCM increasing to 20% EtOAc/DCM) provided the title compound as a white amorphous solid. $^1H$ NMR (500 MHz, $CD_2Cl_2$) δ 8.42 (d, J=1.9 Hz, 1H), 7.96 (d, J=8.8 Hz, 1H), 7.81 (dd, J=8.9, 2.1 Hz, 1H), 7.57-7.46 (m, 3H), 7.41-7.27 (m, 2H), 2.77 (p, J=6.6 Hz, 1H), 2.52 (s, 3H), 2.19 (s, 3H), 1.16 (d, J=6.7 Hz, 3H), 0.81 (d, J=6.7 Hz, 3H); MS (ESI): mass calcd. for $C_{24}H_{22}Cl_2N_2OS$, 456.1, m/z found 457.0 $[M+H]^+$.

Example 16

1-(Azetidin-3-yl)-1-(4-chloro-2-methoxy-3-(4-(trifluoromethyl)benzyl)quinolin-6-yl)prop-2-yn-1-ol

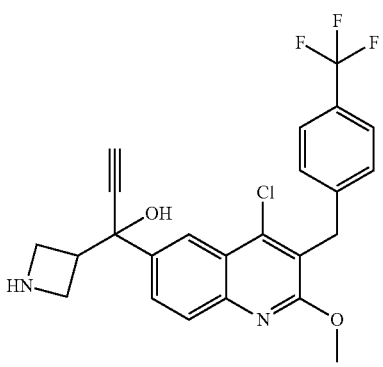 [SMILES: C#CC(O)(c1ccc2nc(OC)c(Cc3ccc(C(F)(F)F)cc3)c(Cl)c2c1)C1CNC1]

To a flask containing tert-butyl 3-(1-(4-chloro-2-methoxy-3-(4-(trifluoromethyl)benzyl)quinolin-6-yl)-1-hydroxyprop-2-yn-1-yl)azetidine-1-carboxylate (165 mg, 0.29 mmol, Example 8) was added formic acid (5 mL, 132.5 mmol). The solution was cooled to 0° C. and 6 N aqueous HCl (50 μL, 0.3 mmol) was added. The mixture was stirred at 0° C. for 30 minutes then allowed to warm to room temperature. After 60 minutes, the reaction mixture was quenched with MeOH (10 mL) and stirred for 15 minutes and then concentrated. The residue was passed through a short column of silica gel (5% MeOH-DCM increasing to 10% 2 M $NH_3$ in MeOH) which afforded the title compound as a light amber solid. $^1H$ NMR (400 MHz, $CD_3OD$) δ 8.44 (d, J=2.0 Hz, 1H), 8.01-7.72 (m, 3H), 7.53 (d, J=8.2 Hz, 2H), 7.40 (d, J=8.2 Hz, 2H), 4.43-4.25 (m, 3H), 4.22-4.09 (m, 2H), 4.06 (d, J=2.2 Hz, 3H), 3.88 (t, J=9.7 Hz, 1H), 3.49-3.36 (m, 1H), 3.36 (d, J=1.9 Hz, 1H). MS (ESI): mass calcd. for $C_{24}H_{20}ClF_3N_2O_2$, 460.1; m/z found 460.9 $[M+H]^+$.

Example 17 tert-Butyl-3-(1-(4-chloro-2-methoxy-3-(4-(trifluoromethyl)benzyl)quinolin-6-yl)-1-hydroxypropyl)azetidine-1-carboxylate

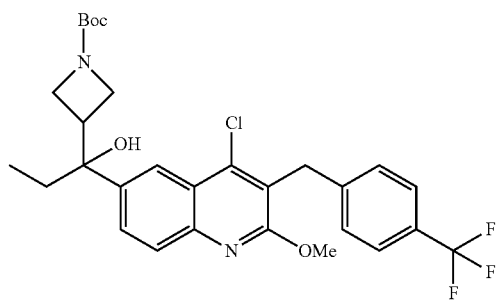 [SMILES: CCC(O)(c1ccc2nc(OC)c(Cc3ccc(C(F)(F)F)cc3)c(Cl)c2c1)C1CN(C(=O)OC(C)(C)C)C1]

To a flask containing tert-butyl-3-(4-chloro-2-methoxy-3-(4-(trifluoromethyl)benzyl)quinoline-6-carbonyl)azetidine-1-carboxylate (250 mg, 0.47 mmol, Intermediate 13: step b) was added THF (8 mL) to give a homogeneous solution. The solution was cooled in an ice-water bath and ethylmagnesium bromide (3 M in $Et_2O$, 0.3 mL, 0.9 mmol) was introduced. After 35 minutes the reaction mixture was quenched with aqueous $NH_4Cl$ solution and extracted with EtOAc, (4×30 mL). The combined organics were washed with brine, dried over $MgSO_4$, filtered and concentrated to dryness to afford a colorless gum. Chromatography on silica gel (5% EtOAc-DCM increasing to 1% MeOH-DCM) provided the title compound as a white amorphous solid. $^1H$ NMR (400 MHz, $CDCl_3$) δ 8.14 (d, J=2.0 Hz, 1H), 7.82 (d, J=8.7 Hz, 1H), 7.60 (dd, J=8.7, 2.1 Hz, 1H), 7.50 (d, J=8.2 Hz, 2H), 7.40 (d, J=8.1 Hz, 2H), 4.35 (s, 2H), 4.16-4.08 (m, 1H), 4.07 (s, 3H), 4.00 (t, J=8.5 Hz, 1H), 3.71-3.53 (m, 2H), 3.20-3.07 (m, 1H), 2.13 (s, 1H), 1.97-1.74 (m, 2H), 1.41 (s, 9H), 0.73 (t, J=7.4 Hz, 3H); MS (ESI): mass calcd. for $C_{29}H_{32}ClF_3N_2O_4$, 564.2, m/z found 565.3 $(M+H)^+$.

In Vitro Biological Data
ThermoFluor® Assay

ThermoFluor® is a fluorescence based assay that estimates ligand binding affinities by measuring the effect of a ligand on protein thermal stability (Pantoliano, M. W., Petrella, E. C., Kwasnoski, J. D., Lobanov, V. S., Myslik, J., Graf, E., Carver, T., Asel, E., Springer, B. A., Lane, P., and Salemme, F. R. (2001) High-density miniaturized thermal shift assays as a general strategy for drug discovery. *J Biomol Screen* 6, 429-40, and Matulis, D., Kranz, J. K., Salemme, F. R., and Todd, M. J. (2005) Thermodynamic stability of carbonic anhydrase: measurements of binding affinity and stoichiometry using ThermoFluor. *Biochemistry* 44, 5258-66). This approach is applicable to a wide variety of systems, and rigorous in theoretical interpretation through quantitation of equilibrium binding constants ($K_D$).

In a ThermoFluor® experiment where protein stability is monitored as the temperature is steadily increased, an equilibrium binding ligand causes the midpoint of an unfolding transition ($T_m$) to occur at a higher temperature. The shift in the melting point described as a $\Delta T_m$ is proportional to the concentration and affinity of the ligand. The compound potency may be compared as a rank order of either $\Delta T_m$ values at a single compound concentration or in terms of $K_D$ values, estimated from concentration response curves.

RORγt ThermoFluor® Assay Construct

For the RORγt construct used in the ThermoFluor® assay, numbering for the nucleotide sequences was based on the reference sequence for human RORγt, transcript variant 2, NCBI Accession: NM_001001523.1 (SEQ ID NO:1). Nucleotides 850-1635 (SEQ ID NO:2) coding for the wild type human RORγt ligand binding domain (RORγt LBD) were cloned into the pHIS1 vector, a modified pET *E. coli* expression vector (Accelagen, San Diego), containing an in-frame N-terminal His-tag and a TurboTEV protease cleavage site (ENLYFQG, SEQ ID NO:3) upstream of the cloned insert sequence. The amino acid sequence for the RORγt construct used in the Thermofluor assay is shown as SEQ ID NO:4.

ThermoFluor® experiments were carried out using instruments owned by Janssen Research and Discovery, L.L.C. through its acquisition of 3-Dimensional Pharmaceuticals, Inc. 1,8-ANS (Invitrogen) was used as a fluorescent dye. Protein and compound solutions are dispensed into black 384-well polypropylene PCR microplates (Abgene) and overlayed with silicone oil (1 μL, Fluka, type DC 200) to prevent evaporation.

Bar-coded assay plates are robotically loaded onto a thermostatically controlled PCR-type thermal block and then heated at a typical ramp-rate of 1° C./min for all experiments. Fluorescence was measured by continuous illumination with UV light (Hamamatsu LC6) supplied via fiber optic and filtered through a band-pass filter (380-400 nm; >6 OD cutoff). Fluorescence emission of the entire 384-well plate was detected by measuring light intensity using a CCD camera (Sensys, Roper Scientific) filtered to detect 500±25 nm, resulting in simultaneous and independent readings of all 384 wells. Images were collected at each temperature, and the sum of the pixel intensity in a given area of the assay plate was recorded versus temperature. Reference wells contained RORγt without compounds, and the assay conditions were as follows:

0.065 mg/mL RORγt
  60 μM 1,8-ANS
  100 mM Hepes, pH 7.0
  10 mM NaCl
  2.5 mM GSH
  0.002% Tween-20

Project compounds were arranged in a pre-dosed mother plate (Greiner Bio-one) wherein compounds are serially diluted in 100% DMSO by 1:2 from a high concentration of 10 mM over 12 columns within a series (column 12 is a reference well containing DMSO, no compound). The compounds were robotically dispensed directly into assay plates (1x=46 nL) using a Hummingbird capillary liquid handling instrument (Digilab). Following compound dispense, protein and dye in buffer was added to achieve the final assay volume of 3 μL, followed by 1 μL of silicone oil.

The binding affinity was estimated as described previously (Matulis, D., Kranz, J. K., Salemme, F. R., and Todd, M. J. (2005) Thermodynamic stability of carbonic anhydrase: measurements of binding affinity and stoichiometry using ThermoFluor®. *Biochemistry* 44, 5258-66) using the following thermodynamic parameters of protein unfolding:

Reference RORγt $T_m$: 47.8° C.
$\Delta H_{(Tm)}$=115 kcal/mol
$\Delta C_{p(Tm)}$=3 kcal/mol Cell Based Biological Data RORγt Reporter Assay A reporter assay was used to test functional activity of RORγt modulatory compounds on transcriptional activation driven by the RORγt LBD. Cells used in the assay were co-transfected with two constructs. The first construct, pBIND-RORγt LBD, contained the wild type human RORγt LBD fused to the DNA binding domain of the GAL4 protein. The second construct, pGL4.31 (Promega Cat no. C935A), contained multiple GAL4 responsive DNA elements upstream of firefly luciferase. To generate a background control, cells were similarly co-transfected with two constructs, but in the first construct the AF2 amino acid motif in the RORγt LBD was changed from LYKELF (SEQ ID NO:5) to LFKELF (SEQ ID NO:6). The AF2 mutation has been shown to prevent co-activator binding to the RORγt LBD, thus preventing transcription of firefly luciferase. The mutant construct was called pBIND-RORγt-AF2.

For the RORγt constructs used in the reporter assay, numbering for the nucleotide sequences was also based on the reference sequence for human RORγt, transcript variant 2, NCBI Accession: NM_001001523.1 (SEQ ID NO:1). For the wild type human RORγt LBD construct, pBIND-RORγt LBD, nucleotides 850-1635 (SEQ ID NO:2) coding for the wild type human RORγt LBD were cloned into EcoRI and NotI sites in the pBIND vector (Promega cat. No E245A). The pBIND vector contains the GAL4 DNA Binding Domain (GAL4 DBD) and the *renilla* luciferase gene under control of the SV40 promoter. *Renilla* luciferase expression serves as a control for transfection efficiency and cell viability. For the background control construct, pBIND-RORγt-AF2, the AF2 domain of RORγt LBD was mutated using the Quik Change II Site Directed Mutagenesis System (Stratagene Cat. No. 200519). The nucleotide sequence coding for the RORγt LBD sequence with the mutated AF2 domain is shown as SEQ ID NO:7. The amino acid sequences for the wild type RORγt LBD and RORγt LBD with the mutated AF2 domain are shown as SEQ ID NO:8 and SEQ ID NO:9, respectively.

The reporter assay was performed by transiently transfecting HEK293T cells with 5 μg of pBIND-RORγt LBD or pBIND-RORγt LBD-AF2 and 5 μg pGL4.31 (Promega Cat no. C935A) using Fugene 6 (Invitrogen Cat no. E2691) at a 1:6 ratio of DNA:Fugene 6 in a T-75 flask in which cells were at least 80% confluent. Twenty four hours after bulk transfection, cells were plated into 96-well plates at 50,000 cells/well in phenol-red free DMEM containing 5% Lipid Reduced FCS and Pen/Strep. Six hours after plating, cells were treated with compounds for 24 hours. Media was removed and cells were lysed with 50 μL 1× Glo Lysis Buffer (Promega). Dual Glo Luciferase Reagent (50 μL/well) was then added and firefly luciferase luminescence was read on an Envision after a ten minute incubation. Finally, Stop and Glo reagent (50 μL/well) was added and *renilla* luciferase luminescence was read on an Envision after a ten minute incubation. To calculate the effect of compounds on RORγt activity, the ratio of firefly to *renilla* luciferase was determined and plotted against compound concentration. Agonist compounds increase RORγt-driven luciferase expression, and antagonist or inverse agonist compounds decrease luciferase expression.

Human Th17 Assay

The human Th17 assay tests the effect of RORγt modulatory compounds on IL-17 production by CD4 T cells under conditions which favor Th17 differentiation. Total CD4$^+$ T cells were isolated from the peripheral blood mononuclear cells (PBMC) of healthy donors using a CD4$^+$ T cell isolation kit II, following the manufacturer's instructions (Miltenyi Biotec). Cells were resuspended in a medium of RPMI-1640 supplemented with 10% fetal bovine serum, penicillin, streptomycin, glutamate, and β-mercaptoethanol and were added to 96-well plates at 1.5×10$^5$ per 100 μL per well. 50 μL of compound at titrated concentrations in DMSO were added into each well at final DMSO concentration at 0.2%. Cells were incubated for 1 hour, then 50 μL of Th17 cell differentiation medium was added to each well. The final concentrations of antibodies and cytokines (R&D Systems) in differentiation medium were: 3×10$^6$/mL anti-CD3/CD28 beads (prepared using human T cell activation/expansion kit, Miltenyi Biotec), 10 μg/mL anti-IL4, 10 μg/mL anti-IFNγ, 10 ng/mL IL1β, 10 ng/mL IL23, 50 ng/mL IL6, 3 ng/mL TGFβ and 20 U/mL IL2. Cells were cultured at 37° C. and 5% CO$_2$ for 3 days. Supernatants were collected and the accumulated IL-17 in culture was measured by using MULTI-SPOT® Cytokine Plate following manufacture's instruction (Meso Scale Discovery). The plate was read using Sector Imager 6000, and IL-17 concentration was extrapolated from the standard curve. The IC50s were determined by GraphPad.

TABLE 1

| Example Number | ThermoFluor ® Assay, Kd (μM) | RORγt reporter Assay, IC50 (μM) | RORγt reporter Assay, % inhibition @ 6 μM | Human Th17 Assay, IC$_{50}$ (μM) |
| --- | --- | --- | --- | --- |
| 1 | 0.24 | 0.15 | 93 | ~3 |
| 2 | 0.52 | 0.45 | 82 | ~6 |
| 3 | 0.89 | >6 | 56 | ND |
| 4 | 1.1 | 1.5 | 114 | ND |
| 5 | 0.62 | 1.3 | 118 | ND |
| 6 | 1.5 | 1.7 | 76 | ND |
| 7a | 0.3 | 0.23 | 95 | ND |
| 7b | 0.23 | 0.36 | 97 | ND |
| 7c | 0.049 | 0.098 | 94 | 0.32 |
| 8 | 3.1 | 4 | 71 | ND |
| 9a | 0.29 | 0.28 | 98 | ND |
| 9b | 0.54 | 1.3 | 89 | ND |
| 9c | 0.054 | 0.18 | 98 | 0.28 |
| 10a | 0.13 | 0.25 | 101 | ND |
| 10b | 0.14 | 0.26 | 96 | 0.64 |
| 10c | 0.14 | 0.33 | 95 | 0.55 |
| 11a | 0.077 | 0.11 | 102 | ND |
| 11b | 0.29 | 0.21 | 98 | 0.87 |
| 11c | 0.036 | 0.015 | 99 | 0.057 |
| 12a | 0.027 | 0.37 | 99 | ND |
| 12b | 0.47 | 0.5 | 102 | 2.1 |
| 12c | 0.015 | 0.041 | 102 | 0.08 |
| 13a | 0.059 | 0.052 | 103 | ND |
| 13b | 0.071 | 0.2 | 101 | 0.17 |
| 13c | 0.021 | 0.046 | 100 | 0.06 |
| 14a | 0.06 | 0.21 | 81 | ND |
| 14b | 0.059 | 0.066 | 84 | 0.19 |
| 14c | 0.13 | 0.31 | 94 | 0.29 |
| 15 | 0.098 | ~0.5 | 99 | ND |
| 16 | ND | ND | ND | ND |
| 17 | 0.39 | 0.5 | 98 | ND |

All data shown in Table 1 is either the value of one data point ot the average of more than one data point.
ND—data While the foregoing specification teaches the principles of the present invention, with examples provided for the purpose of illustration, it will be understood that the practice of the invention encompasses all of the usual variations, adaptations and/or modifications as come within the scope of the following claims and their equivalents.

All documents cited herein are incorporated by reference.

What is claimed is:

1. A compound of Formula I

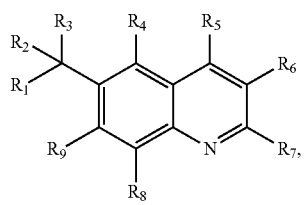

Formula I wherein:
- $R^1$ is azetidinyl, imidazolyl, pyrimidinyl, triazolyl, tetrahydropyranyl, thiazolyl, pyridyl, piperidinyl, phenyl, oxazolyl, or isoxazolyl; wherein said piperidinyl, pyridyl, imidazolyl, and phenyl are optionally substituted with $SO_2CH_3$, $C(O)CH_3$, $CH_3$, $CF_3$, Cl, F, —CN, $OCH_3$, or $N(CH_3)_2$; and optionally substituted with up to one additional group independently selected from Cl, $OCH_3$, and $CH_3$; and wherein said triazolyl, oxazolyl, isoxazolyl, and thiazolyl are optionally substituted with one or two $CH_3$ groups; and wherein said azetidinyl is optionally substituted with $CO_2C(CH_3)_3$, or $C(O)CH_3$;
- $R^2$ is $C_{(1-6)}$alkyl, cyclopropyl, or alkynyl;
- $R^3$ is OH;
- $R^4$ is H;
- $R^5$ is Cl, —CN, $CF_3$, $CH_3$, OH, $N(CH_3)OCH_3$, $N(CH_3)_2$, azetidin-1-yl, or $OCH_3$;
- $R^6$ is pyridyl or phenyl, wherein said phenyl is optionally substituted with Cl, F, $CF_3$, $SO_2CH_3$, or $OCF_3$; or $R^6$ is —O—phenyl, wherein said —O—phenyl is optionally substituted with Cl, F, or —CN; or $R^6$ is —$CH_2R^6$, wherein $R^6$ is pyridyl, or phenyl, wherein said pyridyl or phenyl is optionally substituted with pyrazol-1-yl, 1,2,4-triazol-1-yl, $CF_3$, $OCH_3$, $SO_2CH_3$, Cl, F, or —CN;
- $R^7$ is Cl, —CN, $C_{(1-4)}$alkyl, $OC_{(1-2)}$alkyl, or $NA^1A^2$;
- $A^1$ is $C_{(1-2)}$alkyl;
- $A^2$ is $C_{(1-2)}$alkyl, $CH_2CH_2OCH_3$, or $OCH_3$; or $A^1$ and $A^2$ may be taken together with their attached nitrogen to form a ring selected from the group consisting of:

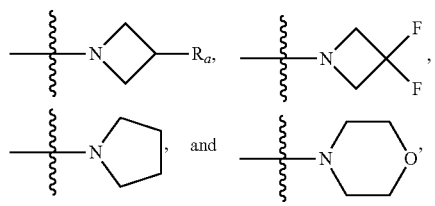

$R_a$ is OH, $OCH_3$, or F;
$R^8$ is H;
$R^9$ is H; and pharmaceutically acceptable salts thereof.

2. A compound of claim 1, wherein
- $R^1$ is azetidin-3-yl, N-acetyl-azetidin-3-yl, N-Boc-azetidin-3-yl, 1-methyl-imidazol-5-yl, 1,2-dimethyl-imidazol-5-yl, 1-methyl-1,2,3-triazol-5-yl, 2,4-dimethyl-oxazol-5-yl, 3-methyl-isoxazol-5-yl, 2,4-dimethyl-thiazol-5-yl, 2,6-dimethyl-pyrid-3-yl;
- $R^2$ is $CH_3$, $CH_2CH_3$, $CH(CH_3)_2$, $CH_2CH_2CH_2CH_3$, alkynyl, or cyclopropyl;
- $R^5$ is Cl;
- $R^6$ is phenyl; or $R^6$ is —$CH_2R^6$, wherein $R^6$ is phenyl; wherein said phenyl is optionally substituted with $SO_2CH_3$, or $CF_3$;
- $R^7$ is Cl, or $OCH_3$; and pharmaceutically acceptable salts thereof.

3. A compound of claim 1 selected from the group consisting of:

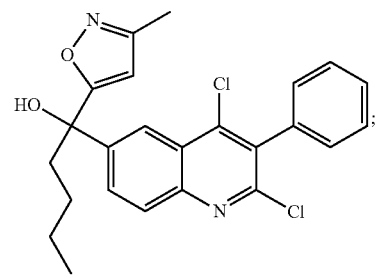

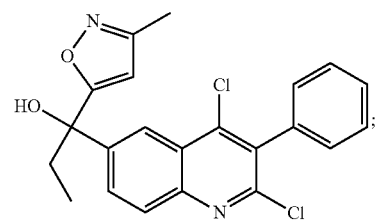

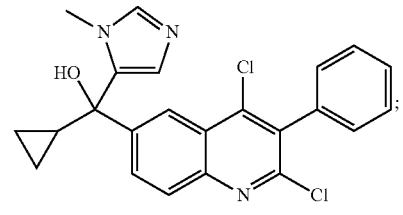

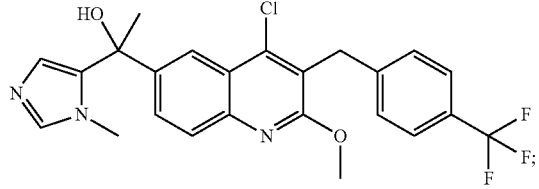

95
-continued
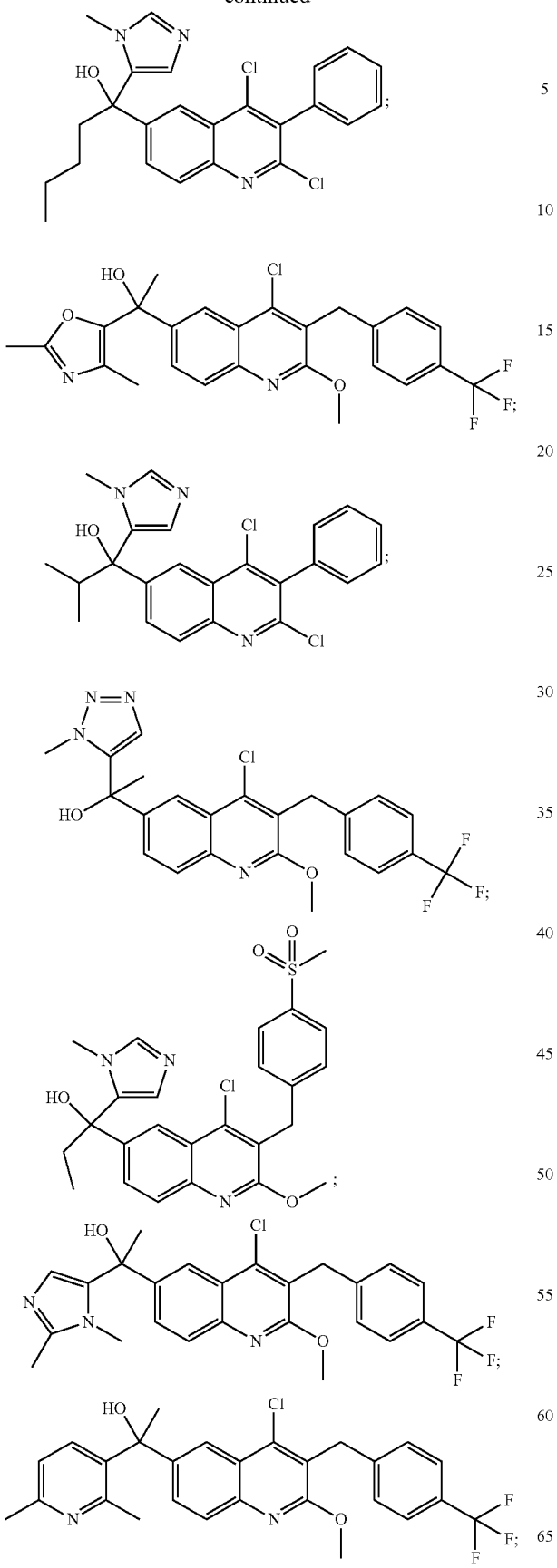
96
-continued
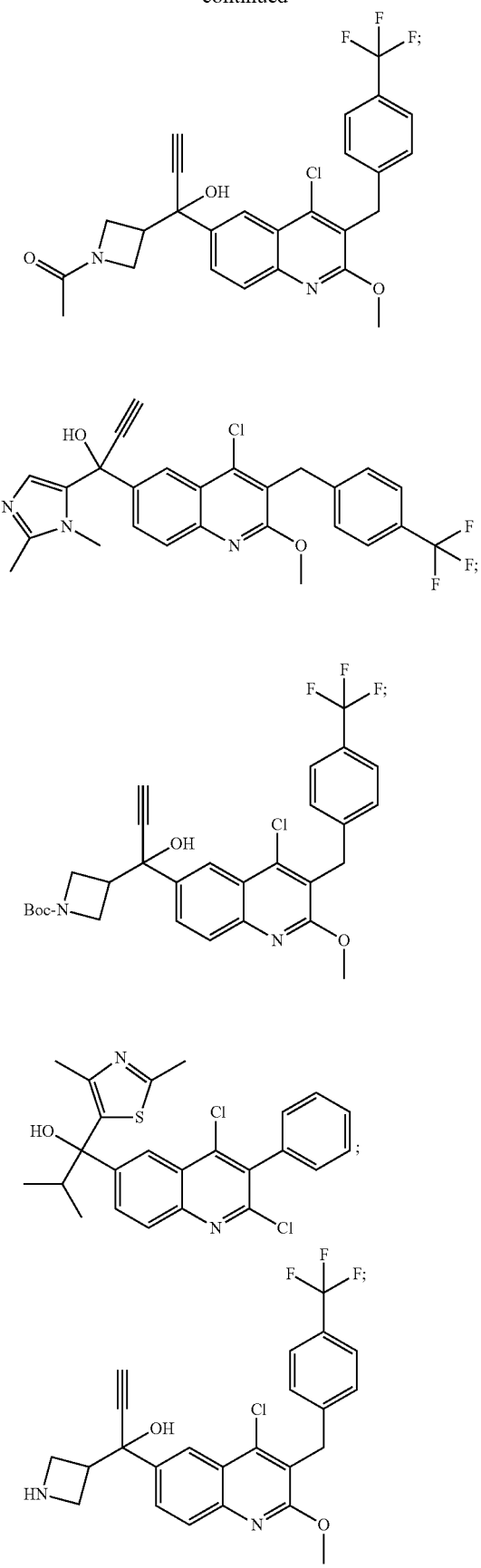

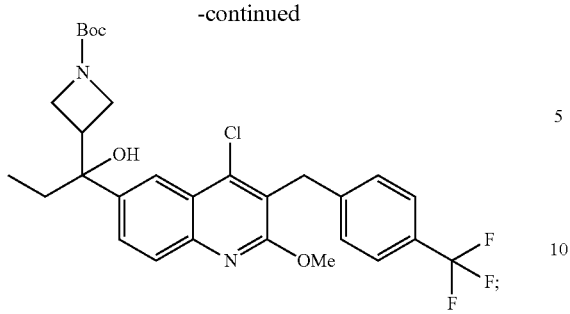

and pharmaceutically acceptable salts thereof.

4. A pharmaceutical composition, comprising a compound of claim 1 and a pharmaceutically acceptable carrier.

5. A pharmaceutical composition made by mixing a compound of claim 1 and a pharmaceutically acceptable carrier.

6. A process for making a pharmaceutical composition comprising mixing a compound of claim 1 and a pharmaceutically acceptable carrier.

* * * * *